US011393358B2

(12) United States Patent
Doherty et al.

(10) Patent No.: US 11,393,358 B2
(45) Date of Patent: Jul. 19, 2022

(54) COACHING AID FOR GOLF

(71) Applicant: SkyHawke Technologies, LLC, Ridgeland, MS (US)

(72) Inventors: Matthew P. Doherty, North Palm Beach, FL (US); James F. Doherty, III, Raleigh, NC (US); William G. Moore, Raleigh, NC (US); Richard L. Root, Ridgeland, MS (US)

(73) Assignee: SKYHAWKE TECHNOLOGIES, LLC, Ridgeland, MS (US)

( * ) Notice: Subject to any disclaimer, the term of this patent is extended or adjusted under 35 U.S.C. 154(b) by 0 days.

(21) Appl. No.: 17/459,520

(22) Filed: Aug. 27, 2021

(65) Prior Publication Data

US 2021/0407317 A1    Dec. 30, 2021

Related U.S. Application Data

(63) Continuation-in-part of application No. 17/354,703, filed on Jun. 22, 2021, which is a continuation of
(Continued)

(51) Int. Cl.
*A63B 69/36* (2006.01)
*G09B 19/00* (2006.01)
(Continued)

(52) U.S. Cl.
CPC ...... *G09B 19/0038* (2013.01); *A63B 24/0021* (2013.01); *A63B 69/36* (2013.01);
(Continued)

(58) Field of Classification Search
CPC ............ A63B 69/36; A63B 2243/0029; A63B 2024/0037; A63B 2024/0056;
(Continued)

(56) References Cited

U.S. PATENT DOCUMENTS 5,507,485 A    4/1996    Fisher
5,810,680 A    9/1998    Lobb et al.
(Continued)

OTHER PUBLICATIONS

Bajek, Dan, "KNR 245," Apr. 29, 2013, downloaded from URL https://www.google.com/url?sa=t&rct=j&q=&esrc=s&source=web&cd=2*cad=rja&uact=8*ved-0CCYQFjABahUKEwi7xujKtj_HAhWMbT4KHWslB2Y&url=http%3A%2F%2Fwww.castonline.ilstu.edu%2Fhenninger%2FDocuments%2FKNS%2520245%2FGroup%2520ResourceSection%25203%2FGolf%FKNR_245_golf.doc&ei=HBHJVbvllozb-QHrkJywBg&US.
(Continued)

*Primary Examiner* — Steven J Hylinski
(74) *Attorney, Agent, or Firm* — Neo IP

(57) ABSTRACT

Systems and methods for golf analysis including a tag coupled to a golf club providing statistical analytics for coaching including text, tabular, graphic, and image-based outputs that include trends information for the golfer, all based upon actual golf play on course situations, wherein the golfer inputs shot data during play, without interrupting the flow of the game, and uploads the shot data for analytics and review online, and wherein all information related to a given user are reviewable by an authorized coach user through a web-based coach access account. The system is further operable to provide the coach user rights for providing corrective or instructive feedback to the user, including visual recommendations such as modified target areas.

5 Claims, 57 Drawing Sheets

Related U.S. Application Data application No. 16/790,273, filed on Feb. 13, 2020, now Pat. No. 11,049,412, which is a continuation of application No. 16/381,712, filed on Apr. 11, 2019, now Pat. No. 10,561,921, which is a continuation of application No. 15/870,359, filed on Jan. 12, 2018, now Pat. No. 10,272,314, which is a continuation of application No. 15/079,086, filed on Mar. 24, 2016, now Pat. No. 9,868,043, which is a continuation of application No. 14/265,218, filed on Apr. 29, 2014, now Pat. No. 9,295,895, which is a continuation-in-part of application No. 12/501,106, filed on Jul. 10, 2009, now abandoned, and a continuation-in-part of application No. 12/012,943, filed on Feb. 6, 2008, now abandoned, and a continuation-in-part of application No. 12/012,942, filed on Feb. 6, 2008, now Pat. No. 8,708,841.

(60) Provisional application No. 61/134,670, filed on Jul. 12, 2008, provisional application No. 60/899,913, filed on Feb. 7, 2007, provisional application No. 60/899,914, filed on Feb. 7, 2007.

(51) Int. Cl.
  *A63B 71/06* (2006.01)
  *A63B 24/00* (2006.01)
  *G01S 19/19* (2010.01)
  *A63B 102/32* (2015.01)
  *G16H 20/30* (2018.01)

(52) U.S. Cl.
  CPC ...... *A63B 71/0622* (2013.01); *A63B 69/3605* (2020.08); *A63B 2024/0056* (2013.01); *A63B 2071/0691* (2013.01); *A63B 2102/32* (2015.10); *A63B 2220/12* (2013.01); *A63B 2220/20* (2013.01); *A63B 2220/70* (2013.01); *A63B 2225/20* (2013.01); *A63B 2225/50* (2013.01); *G01S 19/19* (2013.01); *G16H 20/30* (2018.01)

(58) Field of Classification Search
  CPC ......... A63B 24/0021; A63B 2071/0691; A63F 2300/306
  See application file for complete search history.

(56) References Cited

U.S. PATENT DOCUMENTS

| | | | |
|---|---|---|---|
| 5,816,953 A | 10/1998 | Cleveland | |
| 5,882,269 A | 3/1999 | Lewis | |
| 6,236,360 B1 | 5/2001 | Rudow et al. | |
| 6,322,455 B1 | 11/2001 | Howey | |
| 6,456,938 B1 | 9/2002 | Barnard | |
| 7,010,550 B2 | 3/2006 | Tarlie | |
| 7,118,498 B2 | 10/2006 | Meadows et al. | |
| 8,556,752 B2 | 10/2013 | Meadows et al. | |
| 8,708,841 B2 | 4/2014 | Doherty et al. | |
| 9,295,895 B2 | 3/2016 | Doherty et al. | |
| 9,943,744 B2 | 4/2018 | Meadows et al. | |
| 10,159,885 B2 | 12/2018 | Thornton et al. | |
| 10,427,017 B2 | 10/2019 | Syed et al. | |
| 10,706,273 B2 | 7/2020 | Bose et al. | |
| 2002/0010544 A1 | 1/2002 | Rudow et al. | |
| 2002/0072815 A1 | 6/2002 | McDonough et al. | |
| 2002/0082775 A1 | 6/2002 | Meadows et al. | |
| 2002/0097182 A1* | 7/2002 | Goren | H04N 21/6175 342/357.4 |
| 2002/0107077 A1* | 8/2002 | Buhler | A63B 60/46 473/151 |
| 2003/0103001 A1* | 6/2003 | Huston | G01S 19/19 342/357.25 |
| 2003/0191547 A1 | 10/2003 | Morse | |
| 2004/0147329 A1 | 7/2004 | Meadows et al. | |
| 2004/0172284 A1 | 9/2004 | Sullivan et al. | |
| 2004/0180709 A1 | 9/2004 | Takahashi et al. | |
| 2006/0114363 A1 | 6/2006 | Kang et al. | |
| 2006/0212221 A1 | 9/2006 | Liu | |
| 2007/0026958 A1 | 2/2007 | Barasch et al. | |
| 2008/0108456 A1 | 5/2008 | Bonito | |
| 2008/0201107 A1 | 8/2008 | Doherty et al. | |
| 2008/0259096 A1* | 10/2008 | Huston | G06Q 50/01 345/659 |
| 2009/0233735 A1 | 9/2009 | Savarese et al. | |
| 2010/0009780 A1 | 1/2010 | Doherty et al. | |
| 2010/0093457 A1 | 4/2010 | Ahem et al. | |
| 2010/0099509 A1 | 4/2010 | Ahem et al. | |
| 2012/0007885 A1 | 1/2012 | Huston | |
| 2012/0295739 A1 | 11/2012 | Young | |
| 2013/0095939 A1 | 4/2013 | Meadows et al. | |
| 2014/0244012 A1 | 8/2014 | Doherty et al. | |
| 2015/0126308 A1 | 5/2015 | Penn et al. | |
| 2015/0328523 A1 | 11/2015 | Heling et al. | |
| 2015/0343292 A1 | 12/2015 | Leech | |
| 2016/0199694 A1 | 7/2016 | Doherty et al. | |
| 2017/0274255 A1 | 9/2017 | Meadows et al. | |
| 2018/0133577 A1 | 5/2018 | Doherty et al. | |
| 2019/0051136 A1 | 2/2019 | Savarese et al. | |
| 2019/0232142 A1 | 8/2019 | Doherty et al. | |
| 2020/0179781 A1 | 6/2020 | Doherty et al. | |
| 2021/0166203 A1 | 6/2021 | Code et al. | |

OTHER PUBLICATIONS

Global Positioning System, Wikipedia, http://en.wikipedia.org/wiki/Global_Positioning_System.

Pelz, Dave, "Master Awkward-Distance Pitch Shots," Dec. 1, 2006, retrieved from URL http://www.golf.com/instruction/master-awkward-distance-pitch-shots on Jun. 18, 2014.

Tally, S., New GPS standards won't affect precision farming, Purdue News, http://www.purdue.edu/uns/html4ever/0007.Morgan.GPS.html.

U.S. Appl. No. 60/899,914, filed Feb. 7, 2007 Specification & Drawings.

U.S. Appl. No. 60/899,913, filed Feb. 7, 2007, Specification.

U.S. Appl. No. 61/134,670, filed Jul. 12, 2008, Specification, Claims, Drawings.

\* cited by examiner

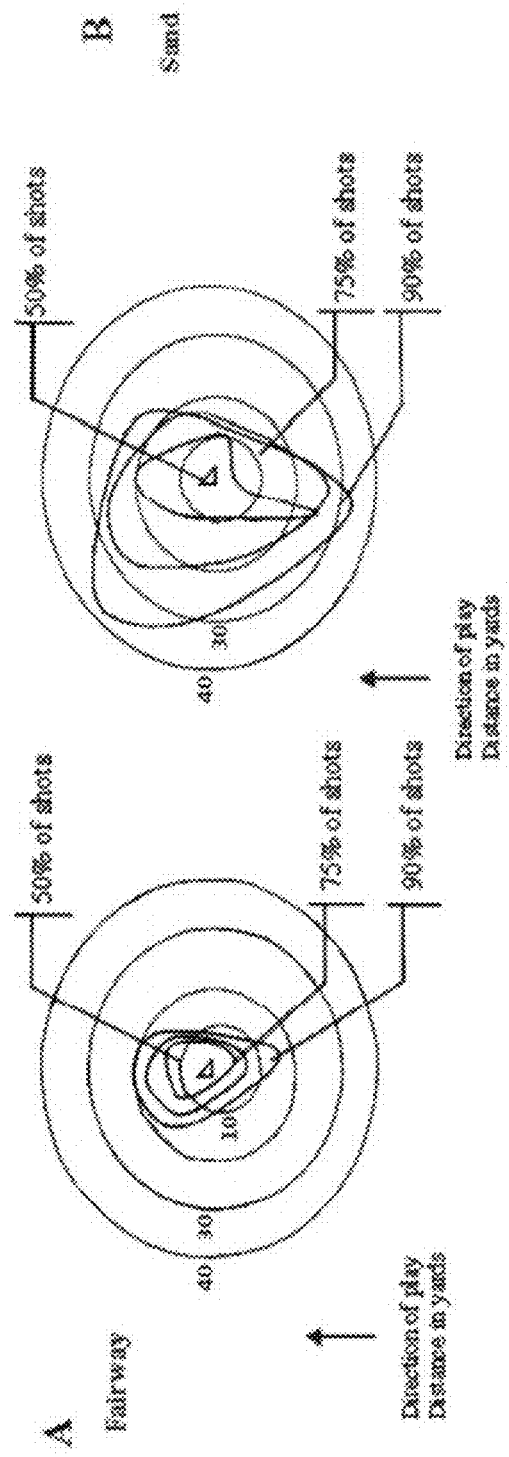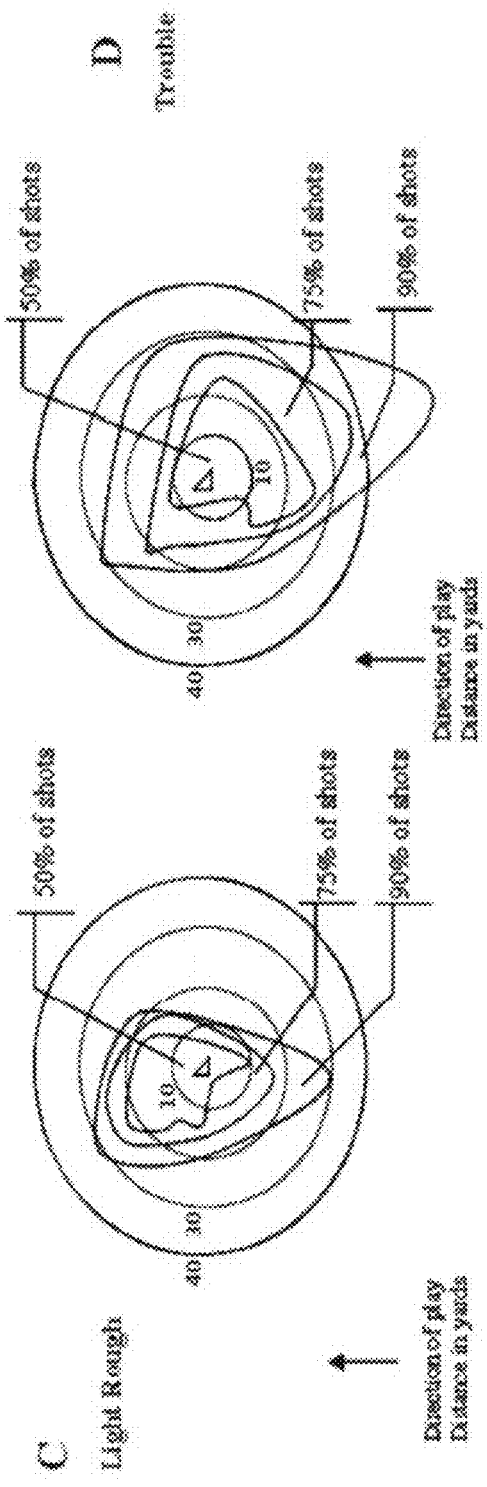
FIG. 33A  FIG. 33B  FIG. 33C  FIG. 33D

COACHING AID FOR GOLF

CROSS-REFERENCE TO RELATED INVENTIONS

This application is related to and claims priority from the following US patents and patent applications. This application is a continuation-in-part of U.S. application Ser. No. 17/354,703, filed Jun. 22, 2021, which is a continuation of U.S. application Ser. No. 16/790,273, filed Feb. 13, 2020, which is a continuation of U.S. application Ser. No. 16/381,712, filed Apr. 11, 2019, which is a continuation of U.S. application Ser. No. 15/870,359, filed Jan. 12, 2018, now U.S. Pat. No. 10,272,314, which is a continuation of U.S. application Ser. No. 15/079,086, filed Mar. 24, 2016, now U.S. Pat. No. 9,868,043, which is a continuation of U.S. application Ser. No. 14/265,218, filed Apr. 29, 2014, now U.S. Pat. No. 9,295,895, which is a continuation-in-part of U.S. application Ser. No. 12/012,942, filed Feb. 6, 2008, now U.S. Pat. No. 8,708,841, which claims the benefit of U.S. Provisional Application No. 60/899,914, filed Feb. 7, 2007, each of which is hereby incorporated by reference in its entirety. U.S. application Ser. No. 14/265,218 is also a continuation-in-part of U.S. application Ser. No. 12/012,943, filed Feb. 6, 2008, which claims the benefit of U.S. Provisional Application No. 60/899,913, filed Feb. 7, 2007, each of which is hereby incorporated by reference in its entirety. U.S. application Ser. No. 14/265,218 is also a continuation-in-part of U.S. application Ser. No. 12/501,106, filed Jul. 10, 2009, which claims the benefit of U.S. Provisional Application No. 61/134,670, filed Jul. 12, 2008, each of which is hereby incorporated by reference in its entirety.

BACKGROUND OF THE INVENTION

1. Field of the Invention

The present invention relates generally to systems and methods for tracking and improving golf performance using statistical analysis of actual performance versus targets.

2. Description of the Prior Art

It is generally known in the prior art to provide a tag for monitoring a golf swing.

Prior art patent documents include the following:

US Patent Pub. No. 2013/0095939 for Golf shot tracking system by inventor Meadows, et al., filed Nov. 6, 2009 and published Apr. 18, 2013, is directed to a golf tracking system including a tag coupled to a golf club. The tag includes a plurality of sensors, each which output a signal based on a detected movement of the golf club, a microcontroller that compares each of the plurality of sensor outputs to stored reference sensor output values, and a transceiver that transmits data corresponding to the sensor outputs to a device remote from the tag based on the comparison performed by the microcontroller. The location-aware device then processes the information received from the tag to determine whether a shot should be registered.

U.S. Pat. No. 9,943,744 for Device and method for calculating golf statistics by inventor Meadows, et al., filed Mar. 15, 2013 and issued Apr. 17, 2018, is directed to a location-aware device including a position determination sensor that determines a position of the location-aware device. A receiver receives, from a tag coupled to a golf club, data corresponding to an output of a sensor included in the tag. A processor associates the data received from the tag with the determined position, and processes the data received from the tag to determine whether to register a golf shot as having occurred at the determined position. A memory stores a golf shot determined to be registered by the processor along with the determined position.

U.S. Pat. No. 10,427,017 for System and method for monitoring performance characteristics associated with user activities involving swinging instruments by inventor Syed, et al., filed May 20, 2015 and issued Oct. 1, 2019, is directed to a system for monitoring and/or tracking a user's performance during an activity involving an instrument that is swung. Exemplary embodiments include a sensor module configured to be secured to the instrument. The sensor module can detect a swing event and/or an impact between the instrument and an object and can implement power management features to limit or manage a power consumption of the sensor module. The sensor module can transmit swing information to an electronic device associated with the user, which can display the swing information, process the swing information, and/or transmit the swing information to a remote system.

U.S. Pat. No. 10,159,885 for Swing analysis system using angular rate and linear acceleration sensors by inventors Thornton et al., filed May 2, 2016 and issued Dec. 25, 2018, is directed to a golf club having a sensor that is removably connected at one or more positions of the golf club where the sensor comprises an inertial measurement unit including an accelerometer capable of measuring linear accelerations in three orthogonal axes and a gyroscope capable of measuring an angular rate of rotation around the same axes. The sensor may further comprise a processor which may perform instructions to detect the impact of the golf club with a golf ball and determine the start of the golf swing without any additional input from the user. The sensor may further have a power management system to extend the life of the power source.

US Patent Publication No. 2017/0274255 for Personal golfing assistant and method and system for graphically displaying golf related information and for collection, processing and distribution of golf related data by inventors Meadows et al., filed Mar. 27, 2017 and published Sep. 28, 2017, is directed to a personal golfing assistant system comprising of software running on a PDA attached directly or remotely to a GPS receiver that enables the user to survey and/or electronically capture geophysical golf data. A handheld device connected to or integrated with a GPS receiver can instead be used. Software allows a golfer to use a handheld PDA/GPS unit during the course of play to mark a ball location automatically and/or determine the distance to golf course targets and/or objects, and to analyze golf related data and generate statistics. The system can send a set of parameters tailored for a specific course to a real time tunable GPS to adjust for optimal performance and can adjust measurements to compensate for environmental condition changes. The system provides an improved graphical method for measuring and displaying distances between a golfer and a golf course object, for displaying multiple measured distances along a line of sight between a golfer and a golf object or target, and for orienting a target or object on a display to coincide with a user's line of sight. There is also provided a method for collecting and uploading golf course geographic information services (GIS) data to an internet accessible server, processing the uploaded data, distributing data upon an authorized user request, and downloading the requested data to an electronic device.

US Patent Publication No. 2019/0051136 for Golf club apparatuses and methods by inventors Savarese et al., filed Aug. 21, 2018 and published Feb. 14, 2019, is directed to methods and systems for managing golf clubs and for collecting golf data, such as golf strokes. In one embodiment, a golf data collection system includes a golf accessory worn on the golfer's wrist, such as a watch, equipped with a GPS receiver, impact sensing and motion sensing means, and a transceiver to communicate with golf club tags (e.g. at 2.4 GHz such as Bluetooth). The golf accessory senses the motion of the golf club being swung by the golf and/or senses the impact of the golf club striking the golf ball. When swinging motion or impact is sensed the device uses the transceiver to communicate with golf club tags. The closest golf club (i.e. the club in the golfer's hand during the swing) is captured as the club used by the swing based on RSSI (Received Signal Strength Indicator).

U.S. Pat. No. 8,556,752 for Personal golfing assistant and method and system for graphically displaying golf related information and for collection, processing and distribution of golf related data by inventors Meadows et al., filed Jul. 2, 2012 and issued Oct. 15, 2013, is directed to a handheld apparatus comprising a computing device; a location measuring device connected to the computing device that generates measured location information corresponding to a location of the handheld apparatus; a display connected to the computing device, wherein the measured location information is used to display a representation of an object on that display, as viewed from above the object, and the representation automatically rotates to orient the representation to coincide with the handheld apparatus' line of sight to the object.

U.S. Pat. No. 5,507,485 for Golf computer and golf replay device by inventor Fisher, filed Apr. 28, 1994 and issued Apr. 16, 1996, is directed to a portable computer to facilitate the game of golf is programmed to record a golfer's score and keep track of various shots and the results of related wagering. Based upon such data and data regarding the layout of the golf course, the computer can provide real time recommendations for club selection as well as providing a summary of the results of a round of golf. Also, the computer can receive global positioning system (GPS) signals to locate a golf ball within a golf course.

US Patent Publication No. 2021/0166203 for System and process for tokenization of digital media by inventor Code, et al., filed Feb. 8, 2021 and published Jun. 3, 2021, is directed to a system and process for converting a digital media file into a digital token. The embodiments modify a digital media file so that a set of rules are attached to the digital media file creating a digital token, which can be used to persist the digital media file through a network. In an exemplary embodiment, the network is a distributed ledger or blockchain based network that securely tracks distribution of the digital media file. The digital token may have a value added to it or value may intrinsically exist as the digital token is persisted through the network. The value associated with distribution of the digital media file may be used to reward the owner of the digital media file, distributors of the token, or as an incentive program for commercial transactions and non-commercial transactions.

U.S. Pat. No. 10,706,273 for Motion capture system that combines sensors with different measurement ranges by inventors Bose et al., filed Nov. 20, 2018 and issued Jul. 7, 2020 is directed to a motion capture system with a motion capture element that uses two or more sensors to measure a single physical quantity, for example to obtain both wide measurement range and high measurement precision. For example, a system may combine a low-range, high precision accelerometer having a range of −24 g to +24 g with a high-range accelerometer having a range of −400 g to +400 g. Data from the multiple sensors is transmitted to a computer that combines the individual sensor estimates into a single estimate for the physical quantity. Various methods may be used to combine individual estimates into a combined estimate, including for example weighting individual estimates by the inverse of the measurement variance of each sensor. Data may be extrapolated beyond the measurement range of a low-range sensor, using polynomial curves for example, and combined with data from a high-range sensor to form a combined estimate.

SUMMARY OF THE INVENTION

The present invention relates to a golfing system for detecting, tracking, and recording a golf shot via a plurality of sensors and providing analysis of the golf shot based on the sensor data.

In a preferred embodiment, the interactive golfing system includes a portable device operable for communication through a network to at least one remote computing device. The at least one remote computing device is configured to receive a user input, during and/or before a round of play, shot, setting and target information. Further, the received inputs include or correlate to GPS information and be stored in a local and/or remote historical database, the inputs and historical information are able to be analyzed locally and/or remotely.

In one embodiment, the present invention includes a method for golf analysis including at least one server with at least one database storing information and providing the information over a network to an application, determining a starting position based on a tag coupled to a golf club, storing the starting position, determining a type of golf club based on the tag coupled to the golf club, and defining a recommended target area based on historical performance data for the type of golf club.

In another embodiment, the present invention includes a system for golf analysis including an application on a computing device configured for network communication with at least one server with at least one database, wherein the at least one server is configured to store information and provide the information to the application, wherein the application is in network communication with a tag coupled to a golf club, wherein the tag includes at least one sensor, wherein the application is configured to receive sensor data from the at least one sensor, and wherein the application is configured to determine when a golf ball was struck by the golf club based on the sensor data.

In yet another embodiment, the present invention includes a golf analysis system including an application on a computing device, at least one server with at least one database, wherein the at least one server is configured to store information and provide the information to the application, and a tag coupled to a golf club, wherein the tag includes at least one sensor, wherein the at least one sensor includes an accelerometer, a gyro sensor, and/or a tilt sensor, wherein the at least one sensor is configured to capture swing data, including motion and position data, during a golf swing, wherein the at least one sensor is configured to transmit the captured swing data to the tag, wherein the tag is configured to analyze the sensor data, and wherein the tag is configured to transmit the analyzed sensor data to the application.

Aspects of the present invention are to provide golf performance analytics, including shot zone diagrams and target analytics, to assist with identification and understanding of golfer errors and trends so that adjustments to form, strategy, and ultimately performance can be made.

Another aspect of the invention is to provide shot zone diagrams in a portable, printed pocket-sized version for individual golfers based upon specific clubs, target, golf course situations and past performance, along with statistical likelihood for present performance under the same or similar conditions.

Another aspect of the present invention is to provide a system for golf performance analytics wherein a user inputs a series of corresponding starting points and targets, wherein the statistical analysis includes text, tabular, diagrammatic, and/or image-based outputs.

Another aspect of the invention, is to provide analytics whereby the directionality of any shot is to be uniformly and consistently oriented to provide a zeroed-out orientation for each shot, and wherein the shot zone diagrams provide information including targets, trends in the user's golf performance over a predetermined period, shot misdirection and corresponding causes related thereto, and/or providing a portable printed version of past or recommended shot performances for any given golf club, golf course, or conditions.

In one aspect of the invention, an interactive system is provided for interaction with a third party, e.g., a coach or teacher, who can provide recommendations, instructive feedback and visual advice such as modified targets, accessible through the interactive device before and/or during golf play. In another aspect of the invention, all information related to a given user can be stored locally on the device or remotely on a server or database, each of which are accessible through a web-based account.

In yet another aspect of the invention, a system configured for golf performance analytics including a golf tag is provided. Advantageously, this provides real-time analytics and club-by-club analysis.

Thus, the present invention provides automatic analytics of golf performance over a period of time, including starting points and targets as a golfer plays a round of golf. Advantageously, compared with prior art, the present invention provides a significant level of detail and customization by the user so that the feedback or statistical output on golf performance and trends provides normalized information that is actionable by the user and/or a third party to correct or improve the user's golf game.

Golf players need accurate distance measurements in relation to a distance from a golf hole. Identifying the distance to a green, the distance from the front and back portions of a green and/or the distance to a hazard can substantially improve a player's game. Additionally, players need the ability to review their shots in real-time and after their round is over. This enables players to learn from their mistakes and adapt their game.

These and other aspects of the present invention will become apparent to those skilled in the art after a reading of the following description of the preferred embodiment when considered with the drawings, as they support the claimed invention.

BRIEF DESCRIPTION OF THE DRAWINGS

Figure 12:
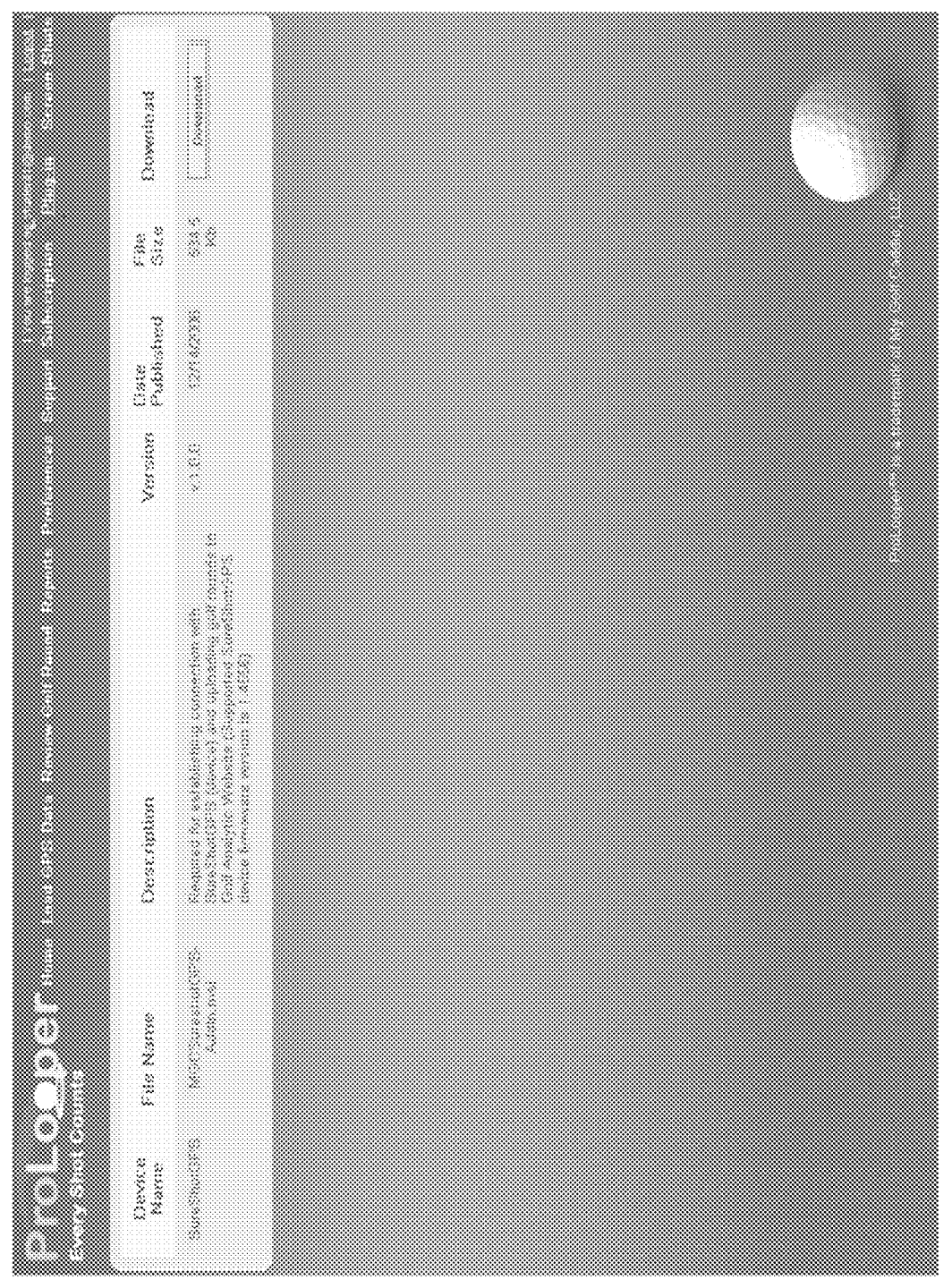

FIG. 12 illustrates a user interface for entering information and viewing analytical outputs according to one embodiment of the present invention.

Figure 15:
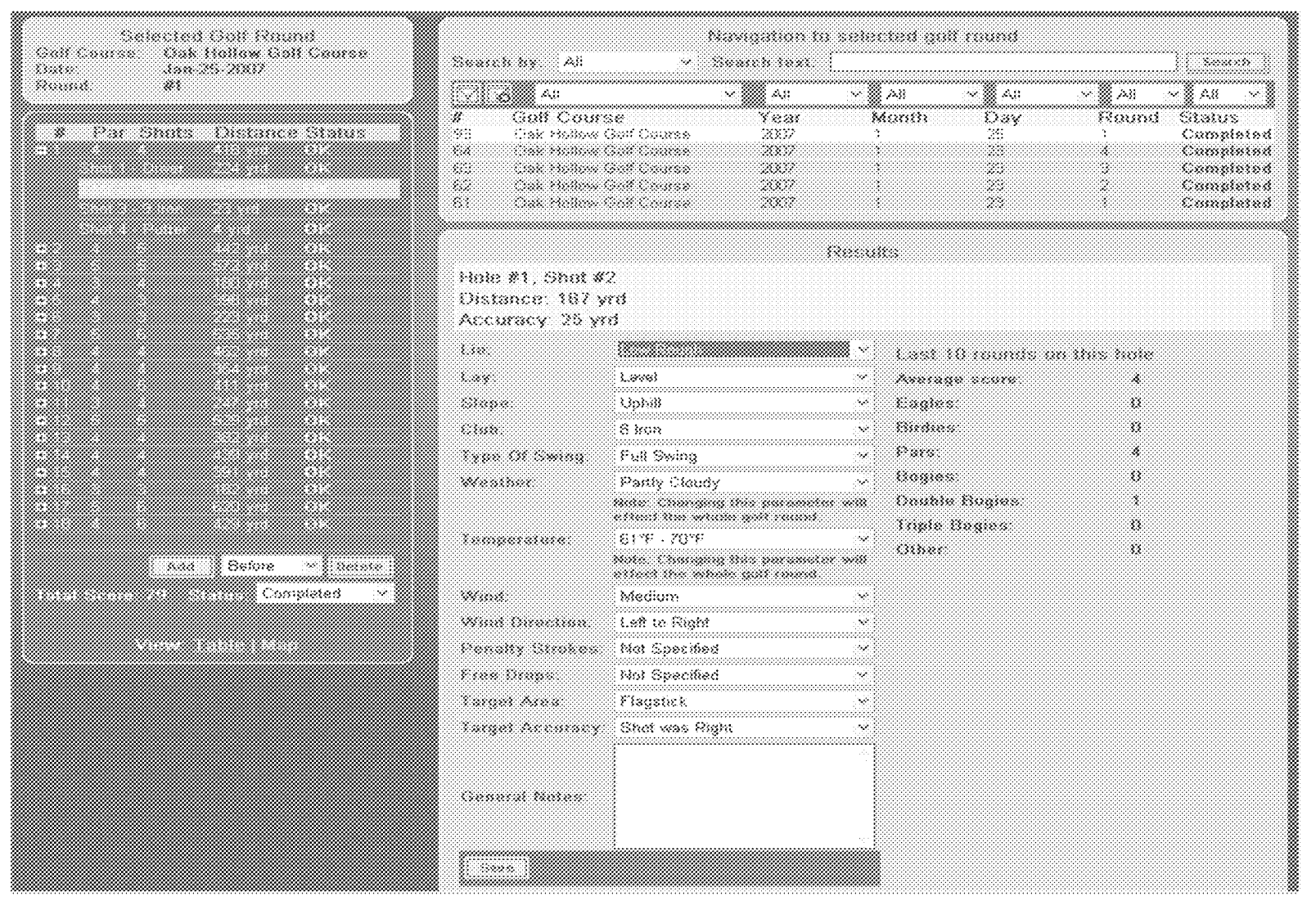

FIG. 15 illustrates a user interface for entering information and viewing analytical outputs according to one embodiment of the present invention.

FIG. 26 illustrates a user interface for entering information and viewing analytical outputs according to one embodiment of the present invention.

FIG. 27 illustrates a user interface for entering information and viewing analytical outputs according to one embodiment of the present invention.

FIG. 33A illustrates a shot zone diagram for a given golf club and a select golf course location and/or condition.

FIG. 33B illustrates a shot zone diagram for a given golf club and a select golf course location and/or condition.

FIG. 33C illustrates a shot zone diagram for a given golf club and a select golf course location and/or condition.

FIG. 33D illustrates a shot zone diagram for a given golf club and a select golf course location and/or condition.

/DETAILED DESCRIPTION

Figure 1:
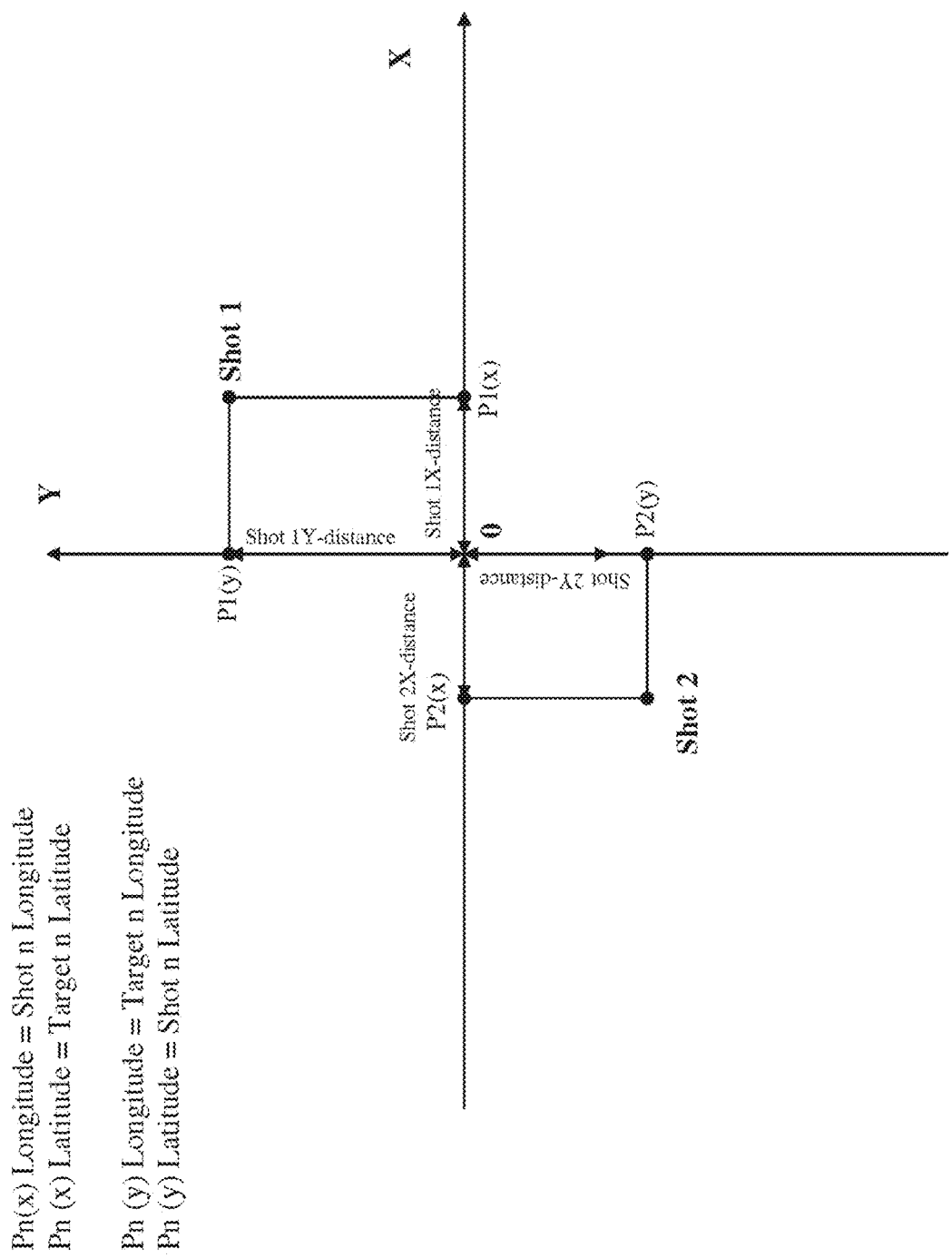
FIG. 1 includes a schematic diagram illustrating a diagrammatic representation of golf performance analytics in accordance with one embodiment of the present invention.

Prior art diagrammatic views of golf performance are known, specifically directional and distance information is known to be generated based upon a golfer's performance on a specific course of play. Also, generally, golf performance statistical programs are known, in particular for using GPS coordinates for tracking shot distances from a starting point, such as a tee, to an end point, such as the hole on the green of a golf course. However, detailed analytics that are specific to course conditions, historical play and trends, targets, and multiple player statuses have not been included. Thus there remains a need for systems and methods that provide for improved statistical analytics of golf performance that includes image-based outputs. Moreover, there remains a need for a portable, printed pocket-sized version of shot performance for an individual golfer based upon a specific club and golf course situations, past performance and targets, along with statistical likelihood for present performance under the same or similar conditions.

Additionally, traditional coaching is typically provided during live sessions in a one-on-one or in a group settings, or through interactive play simulations, wherein a coach can review the live performance of the student(s). There is a lack of capacity to track, monitor, and provide guidance based on play on natural course conditions. Thus there remains a need for systems and methods that provide for improved statistical analytics of golf performance and that include graphic and image-based outputs based on golfer trends upon actual golf play on course situations, wherein the golf play is reviewable by a coach or teacher for third party student(s).

Furthermore, there is a need for real-time data collection, monitoring, and analytics relating to golf performance including a golf tag. A golf tag enables a golf performance system to track the usage of each club and provide analytics related to each swing, hole, round, and/or course.

In one embodiment, the present invention includes a method for golf analysis including at least one server with at least one database storing information and providing the information over a network to an application, determining a starting position based on a tag coupled to a golf club, storing the starting position, determining a type of golf club based on the tag coupled to the golf club, and defining a recommended target area based on historical performance data for the type of golf club.

In one embodiment, the method for golf analysis further includes receiving at least one target modification, wherein the at least one target modification is received from a mobile device. In another embodiment, the at least one target modification includes a change in length, width, shape, perimeter, area, and/or elevation of the recommended target area. In yet another embodiment, the method for golf analysis further includes receiving a resting ball location based on the tag coupled to the golf club and calculating whether the resting ball location is within the recommended target area. In one embodiment, the method for golf analysis further includes receiving wind data, precipitation data, and humidity data, automatically modifying the recommended target area based on the wind data, the precipitation data, the humidity data, and/or the starting position, wherein the starting position further includes lie data. In another embodiment, the method for golf analysis further includes receiving a resting ball location, determining a three-dimensional distance from the resting ball location to the recommended target area, wherein the three-dimensional distance includes a left distance or a right distance, a forward distance or a backward distance, and elevation. In yet another embodiment, the method for golf analysis further includes determining a distance between the recommended target area and the starting position, wherein the distance between the starting position and the recommended target area includes a difference in elevation.

In another embodiment, the present invention includes a system for golf analysis including an application on a computing device configured for network communication with at least one server with at least one database, wherein the at least one server is configured to store information and provide the information to the application, wherein the application is in network communication with a tag coupled to a golf club, wherein the tag includes at least one sensor, wherein the application is configured to receive sensor data from the at least one sensor, and wherein the application is configured to determine when a golf ball was struck by the golf club based on the sensor data.

In one embodiment, the at least one database includes a plurality of golf club types, wherein the tag includes a unique identifier, wherein the application is configured to associate at least one golf club type of the plurality of golf club types with the tag based on the unique identifier. In another embodiment, the sensor data includes geopositioning data, wherein the application is configured to determine a starting position based on the geopositioning data, wherein the tag is associated with at least one golf club type of a plurality of golf club types, wherein the application is configured to determine a recommended target area based on the at least one golf club type of the plurality of golf club types, and wherein the recommended target area is based on at least historical performance data for the at least one golf club type of the plurality of golf club types. In yet another embodiment, the application is configured to receive wind data, precipitation data, and/or humidity data, and wherein the application is configured to automatically calculate a predicted resting position for the golf ball based on the wind data, the precipitation data, the humidity data, and the sensor data. In one embodiment, the application is configured to receive golf course data, wherein the sensor data includes geopositioning data, wherein the application is configured to determine a starting position based on the geopositioning data, wherein the application is configured to generate a recommended target area based on the starting position and the golf course data, wherein the application is configured to determine a distance between the recommended target area and the starting position, wherein the distance between the starting position and the recommended target area includes a difference in elevation, wherein the application is further configured to recommend a golf club based on the distance between the recommended target area and the starting position. In another embodiment, the computing device is configured to receive starting position lie data and golf course data, wherein the starting position lie data includes slope data, wherein the computing device is configured to generate a recommended target area based on the starting position lie data and the golf course data. In yet another embodiment, the tag coupled to the golf club further includes a processor, wherein the processor is configured to analyze the sensor data, wherein the processor is configured to determine whether a golf ball was struck based on the sensor data, and wherein the processor is configured to send an alert to the application when the processor determines that the golf ball was struck.

In yet another embodiment, the present invention includes a golf analysis system including an application on a computing device, at least one server with at least one database, wherein the at least one server is configured to store information and provide the information to the application, and a tag coupled to a golf club, wherein the tag includes at least one sensor, wherein the at least one sensor includes an accelerometer, a gyro sensor, and/or a tilt sensor, wherein the at least one sensor is configured to capture swing data, including motion and position data, during a golf swing, wherein the at least one sensor is configured to transmit the captured swing data to the tag, wherein the tag is configured to analyze the sensor data, and wherein the tag is configured to transmit the analyzed sensor data to the application.

In one embodiment, the application is configured to determine whether a golf ball was struck based on whether the analyzed sensor data is above at least one threshold. In another embodiment, the application is further configured to generate an alert based on the analyzed sensor data, wherein the analyzed sensor data includes club positioning data, acceleration data, and angular velocity data, wherein the alert indicates a quality of a golf ball strike based on the club positioning data, the acceleration data, and the angular velocity data. In yet another embodiment, wherein the tag includes a unique identifier, wherein the application is configured to associate a golf club type with the tag coupled to the golf club based on the unique identifier, wherein the application is configured to determine a golf club type based on the tag coupled to the golf club. In one embodiment, the at least one server is configured to determine a golf club type of the golf club based on the tag coupled to the golf club, wherein the at least one server includes past performance data, wherein the past performance data includes previous shot data, wherein the at least one server is configured to transmit the previous shot data to the computing device, wherein the computing device is configured to display the previous shot data, wherein the displayed previous shot data is related to the golf club type. In another embodiment, the application is configured to determine a starting position, wherein the starting position is based on a location of the tag coupled to the golf club, wherein the application is further configured to receive a resting position via a graphical user interface on the computing device, wherein the application is configured to determine a three-dimensional distance from the starting position to the resting position, wherein the three-dimensional distance includes a left distance or a right distance, a forward distance or a backward distance, and elevation.

In the following description, like reference characters designate like or corresponding parts throughout the several views. Also in the following description, it is to be understood that such terms as "forward," "rearward," "front," "back," "right," "left," "upwardly," "downwardly," and the like are words of convenience and are not to be construed as limiting terms. Referring to the drawings in general, the illustrations are provided for the purpose of describing a preferred embodiment of the invention and are not intended to limit the invention thereto.

The present invention provides a system for golf performance analytics using a computer system including a mobile computing device for receiving inputs from a user during golf play. Golf play includes playing golf, whether a single shot or a series of shots, on the holes of a golf course, a practice tee, or any other location where a golfer makes at least one golf shot. Golf shots include taking a shot from a starting point towards an optionally designated target, the golf shot resting at a ball location. Typically, in a series of golf shots, the ball location becomes the starting point of the subsequent golf shot. Various configurations of the computer system and mobile computing device are described infra.

Input Mechanisms

Users, including golfers, coaches, teachers or another third party, input information related to golf play into a computing or remote device using at least one input mechanism, including, but not limited to, a touchscreen incorporated into a graphical user interface (GUI) or a display and operable with a human hand or stylus, functional and activatable components such as keys, buttons or joysticks, on screen keyboards, voice or movement recognition technology, or any other input mechanisms known to one skilled in the art. In one embodiment, the GUI or display is a touchscreen is configured to receive user input via a user's finger or a stylus, whether by points, lines, drag-and-drop motions or other styles or uses known in the art. In another embodiment, the input mechanism is external to the device but connected, either wired or wirelessly, to the device through an input/output controller.

During golf play, at least one mobile device is configured to receive user input information via the at least one input mechanism. Input information includes information relating to making at least one golf shot and course, weather and/or user conditions. Golf shot information includes at least one starting point and, optionally, at least one target, which includes pinpoint locations, multi-dimensional areas, or zones on the fairway, green or other features of a golf play landscape. Each starting point and target are represented by at least one visual representation on the GUI or display. Furthermore, the GUI or display is operable to include additional visual representations such as golf play landscape features and analytics indicators. In one embodiment, the GUI or display is configured provide interactive features and advertisements, either through the network or from instructions stored on the mobile device.

Preferably, the mobile device includes global positioning satellite (GPS) functionality, enabling user inputs, through the at least one input mechanism, to be combined with at least one GPS coordinate and stored with, or in replacement of, the user input. For example, and not limitation, the mobile device is configured to receive a starting point through the touch of a golf hole visual representation on a touch-interactive screen (e.g. GUI) and display the starting point on the touch-interactive screen and store the starting point in memory in combination with a GPS coordinate representing the location of the starting point. While GPS coordinates are not absolutely precise in their representation of a ball's starting point position on Earth, the GPS coordinate stored in memory is itself an absolute and infinitely precise representation of a location within the mobile device's virtual system, as coordinates that are zero-dimension, geometric point, locational representations. In one embodiment of the present invention, the GPS coordinates are generated using an ASP.NET library for the GPS calculations, for example as with Geo Frameworks. For calculation of distances between two GPS coordinates using the ASP.NET library, the Position class is used. Two instances of Position class are initiated with longitude and latitude that they get from the handheld GPS device, those positions are the start and result coordinates. The Position.DistanceTo (Position destination) method is used to obtain the distance between two points. Alternatively, the present invention systems and methods are adaptable to be used or retrofitted to use on existing GPS mobile devices.

User Inputs

During or before a first golf play, according to one embodiment of the present invention, a user enters a unique user identification and secure login, such as by password, via the device interface, thereby creating a user account. The system and methods of the present invention also provide for options that permit a golfer to set up pre-game settings including starting points, targets, and default targets for a particular golf course. For example, a mobile device is configured for user selection of the tees that a user is playing from (e.g. white tees), thereby defining the starting point on each hole of a golf course. Additionally, the mobile device is operable to receive user selection for applying default targets to some holes and new targets to other holes, to account for the weather or golfer conditions. In another embodiment, the system is configured to record favorite clubs, which prevents users from having to scroll through the entire list of clubs when reviewing shots on the user interface. Secondary shot information is also stored and saved in the pregame settings. All pre-game settings, once inputted, are easily retrievable and allow the user to save time when playing a game. In addition, pre-game settings are modifiable as needed via the device interface during the course of play.

Shot Information

Before making a first shot during golf play, the system is configured to receive primary shot information from a user, including at least one starting point representing the location of the golf ball before a golf shot. In another embodiment, the system is further operable to receive a target via user selection. Each primary shot input is associated with GPS coordinate data or relational data, whether in a GPS virtual system or a stored relational location system, respectfully. In another embodiment, during the golf play of a hole on a golf course, the system is configured to receive a series of starting points and targets, including an initial start point and target for a first golf shot, an intermediate start point and target for a second golf shot, and at least another start point and target for a third golf shot, until the golfer successfully reaches the golf hole. In one embodiment, the starting point and target relate to a golf course, and more particularly to a hole playable on a golf course. In another embodiment, the starting point and target relate to a landscape used for practice, and the user is a third party entering information relating to a golfer's shot. Additional combinations are apparent to those skilled in the art upon a reading of the foregoing description.

In another embodiment of the present invention, the device prompts the user to mark the starting point by either recording the user's position or permitting the user to input the starting point via the interface using an input mechanism. The device is further configured to prompt the user to input a target, such as by prompting whether the pin that marks the hole is to be used, whether the default target is to be used or modified, and/or whether a new target is to be inputted. In one embodiment, the system is configured to use the default target if it does not receive a selection by the user. In another embodiment, if the system receives YES, and the pin location or default target is to be the target, then the user proceeds with the shot to hit the target; if the system receives a NO, then the system is configured to modify the default target or create a new target either automatically or via user input. The system is also operable to receive user input for refusal to use a target.

Once a shot is completed and the ball lands in a next location or position, the ball location is inputted by the user and is typically used as the starting point for the next shot, except in circumstances described infra, such as shots out of bounds and shots in hazards, such as water. The system is operable to receive a user selection to choose to continue until the target is reached or new target(s) corresponding to any additional starting point(s). For a hole on a golf course, the user continues until the hole is played out, and the ball is placed in the hole. The user continues to mark the pin or next start location and a series of start-to-target entries are made until the hole is played out, including putts.

A starting position or resting ball location is inputted by a user via the input mechanisms to mark the user's ball location as a pinpoint position, the resting ball position being the resting position of the previous shot and the starting position of the upcoming shot. The starting position is configured to be inputted by capturing the device's location, when a user is standing near or over the ball location, or is operable to be inputted through selection of a point on the GUI or display, which, in one embodiment, is related and stored with associated GPS coordinates or relational position information.

Additionally, the system is operable to receive secondary shot information inputted by a user, including a club selection, golf course conditions, weather conditions, golfer conditions, equipment specifics, shot corrections, penalty shot positions, and combinations thereof. The system is configured to receive secondary shot information for each shot or at least one shot. Further, the system is configured to receive secondary information for one golf shot and to have the secondary information serve as default secondary information, wherein the default secondary information is automatically entered for each consecutive shot unless otherwise directed by the user. One, some or all of the secondary information is operable to be set as default when the user inputs the pre-game settings or sets the pre-game settings as default during golf play, such that the secondary information is configured to be modified from its default setting at any point during golf play.

Targets

The system is configured to receive at least one target as a pinpoint coordinate location, a multi-dimensional area, a zone on the fairway, a green, or another feature of a golf play landscape via at least one input mechanism. The system is configured to receive target information before, during or after golf play. Advantageously, target information include intermediate targets en route to a final target. Final targets include pinpoint locations, such as a pin location.

Target points are zero-dimensional, single pinpoint coordinate locations on the golf play landscape and are inputted by a user. Target points are entered using an input mechanism via the device interface and correspond to a GPS or relational position. An exemplar target point is a golf course hole coordinate location.

Target areas are areas located on the golf play landscape. In one embodiment, a target area is defined by its position, dimensions and shape, as inputted by the user via an input mechanism; the target position defines the center of a target shape, and the target dimensions define the dimensions of the target shape. For example, and not limitation, a target area is defined by choosing a target position, then selecting a predetermined target area shape from a drop-down list, wherein the device automatically retrieves target dimensions from the default pre-game settings or from historical data from a user account. Historical data from a user account includes any inputted primary or secondary data, and any corresponding analytics or averages over periods of time, courses, or conditions, such that a target area's position, dimension and/or shape is uniquely related to a user's golf history. For example, and not as a limitation, an automatically created target area is created wherein the target position is equal to the average of the inputted club's average distance for the user under the current course conditions (high winds, sunny, healthy golfer), the target dimensions correspond to the percent error indicator (PEI) for the selected club, and the target shape corresponds to the average distance and direction when a target is missed by the selected club.

Notably, any target, whether a point, area or zone, is automatically recommended based on an account's historical data and pre-game or default settings. For example, and not limitation, all historical data associated with a selected club is combined with a default setting that all targets are points or zones in order to automatically calculate the position of the point or the area of the zone. The graphical user interface is configured to display an automatically calculated target on the graphical user interface for viewing by the user, and is further configured to modify the target or save the target as a default target, if so desired via user selection. In one embodiment, a target area is calculated using historical club data for an account, wherein the target position is equal to distance from the starting point, centered on a fairway or green, equal to a club average for the account over a particular time range. Alternatively, the position distance from the starting point is equal to the club average plus or minus a percentage of the club average. The target shape is operable to be set during pre-game settings using a default and calculated using statistical analysis similar to FIGS. 32-33, or the target shape is operable to be set by user input. For example, and not limitation, the target dimension(s) are equal to a percentage of a club average for the account over a particular range, the percentage either being inputted during play or before play as a default in the pre-game settings. For example, and not limitation, the system is configured to receive user input indicating the target position to be 5% above the club average, the target dimension range to be within 15% of the club average, the target dimension width to be within 25% of the club average, and the target shape to be an oval. Advantageously, any averages are configured to account for other primary or secondary shot inputs, such that the target calculation is operable to be limited to historical information for the account, or multiple accounts, matching the course condition, lie, shot type, starting position, etc.

Alternatively, the target area is defined by selecting a target point, selecting a predetermined target shape, then inputting at least one dimension for the predetermined target shape. The system is configured to automatically calculate other dimensions if only one dimension is inputted, and automatically draw the target area with the target point as the center of the target area. To speed the play of golf, the system is operable to receive user input pertaining to any of a target, a target position, at least one target dimension, a target shape, and/or a target outline before play during the pre-game settings, during play, during play and set as a default, or after play for future use or account modification.

In another embodiment, a target area is defined by customized outline created using the input mechanism, such that the outline consists of a series of GPS or relational position points defining the border of the target area. In such an embodiment, the system is operable to receive an outline of the target via a touchscreen, either point-by-point, segment-by-segment continuous lines, or by a single continuous line. In another embodiment, the system is operable to customize target areas by receiving user selection to limit the target's outline within the fairway, the result being for a target square of 50 yards in length being placed on a fairway of 40 yards in width to be automatically modified such that the width of the square is 40 yards up to the fairway's borders, yet the length remains 50 yards. Advantageously, the system is operable to receive similar customizations with respect to a green, practice area, or other golf play landscape feature.

An example, but not a limitation, includes the system, before golf play, receiving target information via user selection, the user selection defining all targets as being an oval having a width of 25 yards and a depth of 15 yards, such that, during golf play, the system receiving user inputs including a target area position on the GUI or display. The device is configured to automatically defining an 25 yard by 15 yard oval with the inputted position as the oval's center-point. As another example, the system is configured to set pre-game defaults as including a custom outline as the default target for hole 1, an oval with dimensions of 25 yards by 15 yards for hole 2, a circle with a radius dimension of 20 yards up to the fairway border for hole 3, etc.

In one embodiment, target zones are areas defined by a range of distances as a length and a width that stretches to the edges of a feature, such as a fairway, green, landscape border or golf course border. In one embodiment, the system is configured to receive user input defining the target zone's length as being a range of distances from the starting point (e.g., input of 200-230 yards creates a target zone of 30 yards in length, the zone starting at 200 yards from the starting point and ending at 230 yards from the starting point), and the target zone's width as being a landscape feature (e.g., the feature being a fairway, thereby creating a target zone stretching between the borders of the fairway, with a 200 and 230 yard arch as the distance dimension borders). In another embodiment, the system is configured to highlight a portion of the fairway that is the desired target zone via a user input mechanism, thereby allowing the device to define a range of distances and feature by estimation, either by the width of the digit being applied or by calculating a swipe center and applying a default range of distances thereto. For example, if the interface receives an input averaging between 280 and 300 yards around the fairway center, the device is configured to prompt the user to confirm such estimation, although the device is operable to receive user input to accept such estimation, or receive a modification of the estimation.

The present invention is configured to receive target information before, during, or after golf play, in relation to a starting position, golf course hole, and/or landscape. In one embodiment, when targets are entered before golf play, at least one target is provided, which is saved in the system's pre-game settings. In such an embodiment, when inputting primary shot information, the system is configured to automatically display and/or input the pre-game target settings. The system is configured to modify and/or replace the pre-game target settings based on user input. In one embodiment, after a target is inputted through at least one input mechanism, the target is displayed on the graphical user interface of the device and is operable to receive a command to save the default target. The system is operable to automatically display the default target based on when the system detects that a user's position is at, or near, the same starting position, depending on the pre-game settings.

After the first shot, and in relation to each new starting position, the system is further operable to receive new targets as desired. In one embodiment, for each target being inputted, the system is configured to prompt the user to select a club from a club list or automatically display and/or input a default club previously identified by the user, either in the pre-game settings or during previous golf play. In another embodiment, once a club is selected, the system prompts the user with a target recommendation based on the golfer's history using the selected club; subsequently the system is configured to receive an approve target recommendation, modify the target recommendation, or replace the target modification with a new target based on user input. In one embodiment, if the system receives a selection relating to a lie of "green", then the next shots on that hole will automatically default to green, and the club will automatically change to putter; such a feature, as with most features of the invention, are designed to save the user time when playing and/or reviewing a round.

Notably, the analytics based on target areas and zones includes any number of distance measurements, whether it be to the nearest point on a target outline, the point where the outline intersects with a line connecting the starting position and the target center, the target center, or another target point. Additionally, the system is configured to receive a target selection through an input mechanism with a single click, wherein the single click, without any further inputs, is registered by the device to record the current GPS location as the starting position and to calculate the target using the default or pre-game settings. Such functionality minimizes the device's intrusion into game play by merely allowing a user to slide their hand in their pocket and make a single input before or after making a shot. Alternatively, the device includes motion sensing technology (e.g. a golf tag) such that the swing of a golfer is detected, thereby marking the starting location and inputting a target automatically, with no effort during game play on the part of the golfer or user.

Modifications

In one embodiment of the invention, once a target has been created or selected, the system is configured to receive a target modification. Target modifications include adjusting the position, dimensions and/or shape of the target. For example, and not limitation, the target modification includes confining a target zone to a different course feature, or changing whether a target is identified as a default target for a starting point. In one embodiment, the device is operable to receive target modifications via at least one input mechanism and further include modifications made by a coach or third party after golf play, modifications made by a coach during golf play, modifications made by a golfer or user before golf play, or, more generically, modifications made by any user at any time after a target has been created or modified. For example, and not limitation, the system is operable to receive target modifications in the same, or similar, way that a target is first created via user input.

By way of example and not limitation, one embodiment of the invention permits a user to modify a target area location during golf play. Before a user hits the first shot on a par 4, the device is configured to receive a target modification due to high winds. The device is configured to receive new dimensions, a new position, a new shape, or even change a target area to a target zone or target point via a GUI or display. In one embodiment, the GUI or display include click and drag functionality. The click and drag functionality enables the device to receive user input including dragging the displayed default target to a new position on the GUI or display, thereby modifying the target but not modifying the default target itself.

In another embodiment of the invention, resting ball locations are configured to be modified via user input. This feature can be used when a golfer's shot lands in a body of water, out of bounds, or in a hazard area, wherein a ball location will differ from the subsequent shot starting point. According to typical golf rules, landing in one of these areas requires the golfer to either retake the shot from the previous starting point or drop the ball in a certain location away from the ball location. In such a case, the system is operable to receive input for the ball location, even though it is not playable, in order to allow the ball location to be included in the statistical analysis. Additionally, the system is further operable to receive a starting point that differs from the ball location so that the statistical analysis and other features, such as feedback and default target areas, remain properly applied to the shot location as well. For example, this enables the system to consider the actual location or area where the ball hit the water and not that the shot it merely landed at that drop point. As with inputting target information, the system is configured to receive ball locations through the interface using any one of the input mechanisms. In one embodiment, the ball location, which differs from a starting point, will be indicated with an X to indicate that this is an estimate rather than an actual pinpoint location of the ball at the end of that shot.

Once a target is finally inputted, the golfer proceeds with the shot and inputs the resulting ball location position. By observing the ball location after a shot, and depending on whether the target was accurate or beneficial to the user, the system is operable save the target as a default target for future use when making a shot from the starting point. The system is further configured to receive user input indicating whether the default target should be used only at that starting point, typically in the case of a tee box, or be used within a certain distance of that starting point, such as a second fairway shot on a par 5. The default target is saved to the course settings user for future play or review by a coach or third party, such as being saved to the course map for review during future play when deciding where to play a target.

Analytics

In one embodiment, the GPS-captured and/or received inputs are stored locally on the device or transferred between devices before, during or after golf play through a wired or wireless network. For example, the device is configured to continuously upload data to another device during golf play via a wireless network, upload data to a mobile device through a wired connection during golf play, or upload data after golf play to a server device. Various computer system embodiments allow for a plurality of information sharing scenarios over wired and/or wireless networks, as is described supra. These inputs can be associated with one or more user accounts, the user account being that of the golfer, coach, third party, or user inputting the information, such as a caddie.

The system is configured to download GPS data from or uploaded to another device, preferably directly from the user device without requiring additional software or data to be saved or otherwise stored on an intermediate computer. While the user is logged online from any connected device, the system is configured to display any presently loaded or prior-loaded inputs from golf play for modification or manipulation, including providing inputs for additional information that provide more detail on the conditions of play. In one embodiment, the device within the system includes software for performing statistical analysis on the inputs and for providing output in the form of text, tables, diagrams, images and combinations thereof. In one embodiment, the data and analytics is stored and categorized by user, golfer, coach, course, hole, primary shot information, secondary shot information and/or course conditions.

In one embodiment, the present invention provides for situational golf shot data and analytics. Significantly, the golf shot data and analytics of the systems and methods of the present invention are provided in a relative mode, i.e., each shot is directionally compared to a starting point and a target, wherein that direction is zeroed out to a (0,0) coordinate starting point and the direction is consistently oriented for each shot such that when all shots are considered collectively, regardless of actual GPS or relational direction or positioning, trends information is quickly identifiable because all shots are aligned in the same direction for the purposes of the analytics on the remote server computer. Thus, while the actual shots are taken during play on a golf course, the situation-neutral based system eliminates the actual GPS directionality of any shot from start point to target and uses a zeroed directionality instead to facilitate comparison of shots and their deviation from target direction.

The systems and methods of such an embodiment are thus particularly useful in a practice mode. Since the directionality is zeroed by the software running on the server computer, the inputs from the application user and GPS data provide accuracy of the actual shot versus target comparisons, but the data is also useful for practice apart from the context of a course. The situational shot data, or situation-neutral shot data, is based upon the initial start point and first target; the second start point and second target, etc., until the final shot from final start point to final target (and final actual shot) are completed, wherein each respective start point and target are considered out of context of a course of play or golf course location. Each shot start point is zeroed out and its location established as the zero point with direction of play oriented to a consistent, predetermined direction, such as true north. Statistical analytics relating to the shot data are provided including outputs having scattergraph diagrams that include information relating to the directionality of any shot to be uniformly and consistently oriented to provide a zeroed-out orientation for each shot, thereby assisting the user/golfer with identification and understanding of errors and trends related to shot misdirection and the corresponding causes related thereto. In this way, adjustments to form, strategy, and ultimately performance, can be made by the user.

The system is configured to create at least one graphical visual representation of the starting point and target based on the inputs, or a selection thereof, captured during golf play. The system further includes analytics indicators for shot accuracy based upon user inputs for the target for a multiplicity of shots. Other options include saving inputs based on the visual representation itself, operating a report function to generate basic feedback about a golfer's play inputs compared to targets, clubs, conditions, and combinations thereof. For example, and not limitation, reports include average score, breakdown by par/hole, scrambling percentage, sand saves, driving accuracy, and other standard metrics and combinations thereof, as well as trends information. Additionally, information is available for review by club, by conditions or situations such as represented by the secondary inputs. A percent error index (PEI) is also available. The PEI is a calculation of how close the actual user shots were from start to targets for each series within the play period, which include the golf course, a series of holes on a golf course, a practice session, a golf school or lessons by professional instruction over a predetermined period of time.

FIGS. 1-11 are schematic drawings illustrating diagrammatic representation of golf performance analytics in accordance with an embodiment of the present invention.

FIGS. 12-31 illustrate screen shot images of user interfaces for user input of information and coordinate data and for viewing statistical and analytical outputs.

Figure 16:
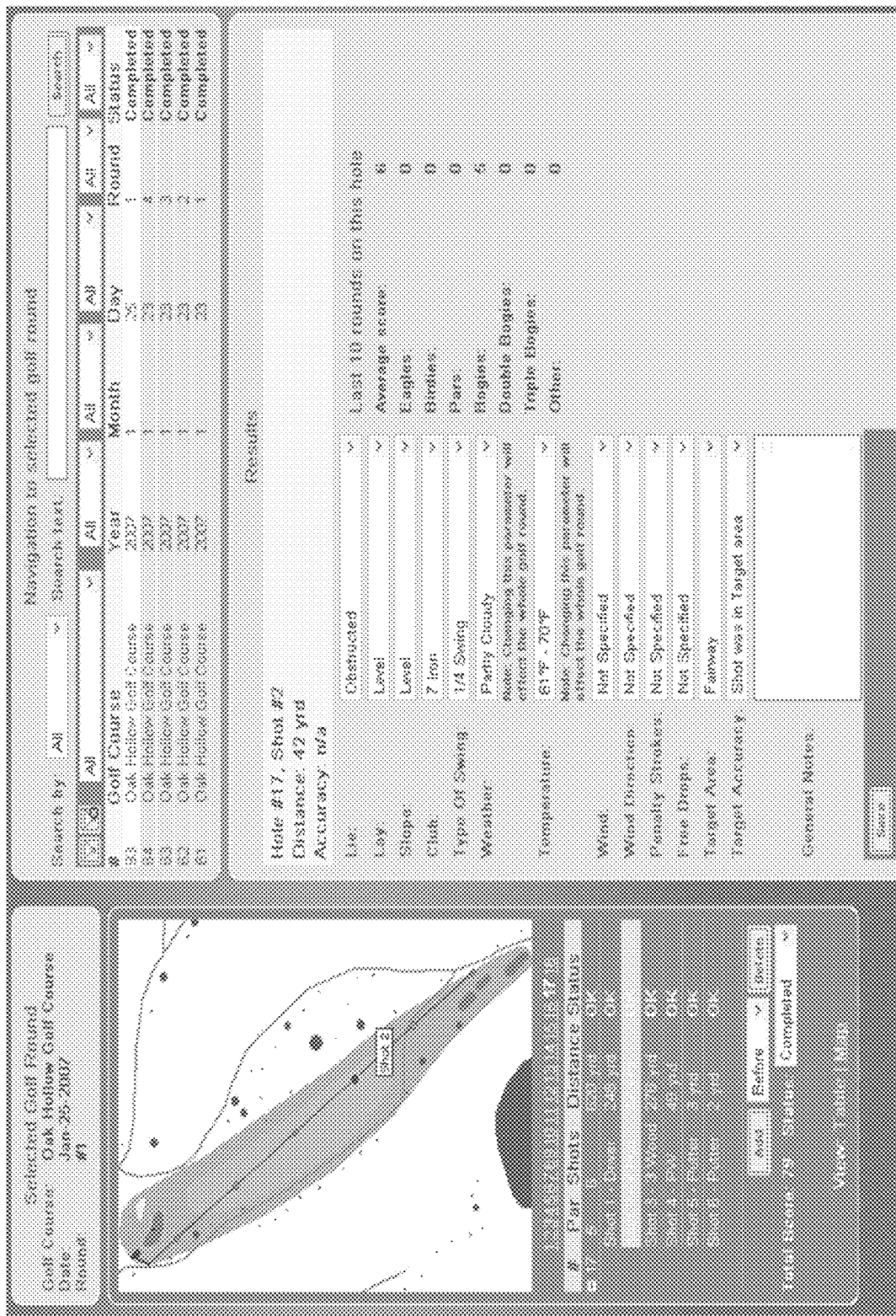
FIG. 16 illustrates a user interface for entering information and viewing analytical outputs according to one embodiment of the present invention.

In one embodiment of the present invention, the systems and methods provide for at least two different ways to look at or review a round with visual representations via the website interface, specifically "Table" and "Map" views, as illustrated in the figures. Table view is an easy to view screen that just lists each shot, along with the distance, as illustrated by the website screen shot in FIG. 15. A Map view is illustrated in FIG. 16. To edit the properties of a particular shot, the system is configured to receive a click-selection or selection via user input for a given shot represented on the user interface. The system is operable to receive secondary shot and other situational information through the user interface. The use of defaults during pre-game settings is preferable so as not to interrupt or slow the flow of the golf game while it is in progress. However, if a device is being used by a third party, such as a caddie, then additional inputs are made easily without interrupting the flow of the game.

Another option for reviewing a golf round is with the Map view user interface, as shown in FIG. 16. This graphical representation of a golf course is provided for golf course play where those courses have been mapped by a GPS coordinate system, aerially, or otherwise depicted approximately to scale or at least representative of the course layout and distances with respect to each hole. If the course the user is reviewing does not have a map available for any reason, then a blank screen is provided that indicates that the course is not mapped or that a map is not yet available.

The system is configured to review shots at any time by receiving a shot selection of the shots below the map, the interface indicating the resting ball location and target for each shot selected. The graphical representation of the shot itself is configured to be displayed in multiple variations. For example, and not limitation, the graphical representation includes a straight line between the starting point and resting ball location or a curved line to best depict the shot type. Preferably, the system is configured to display the actual line that a golfer's shots have taken, from the tee to the hole, and/or intermediate shots therebetween.

In the contingency for penalty shots, if a golfer hits their shot into the water, then the system cannot receive the ball's location based on the golfer's location. The system is configured to receive user selection on the map to show where a particular shot landed. Alternatively, if no map exists, the system is configured to estimate the distance. When finished the round changes to "Completed" status, and is now part of the statistics in the Reports section (see FIG. 16).

Reports

Figure 17:
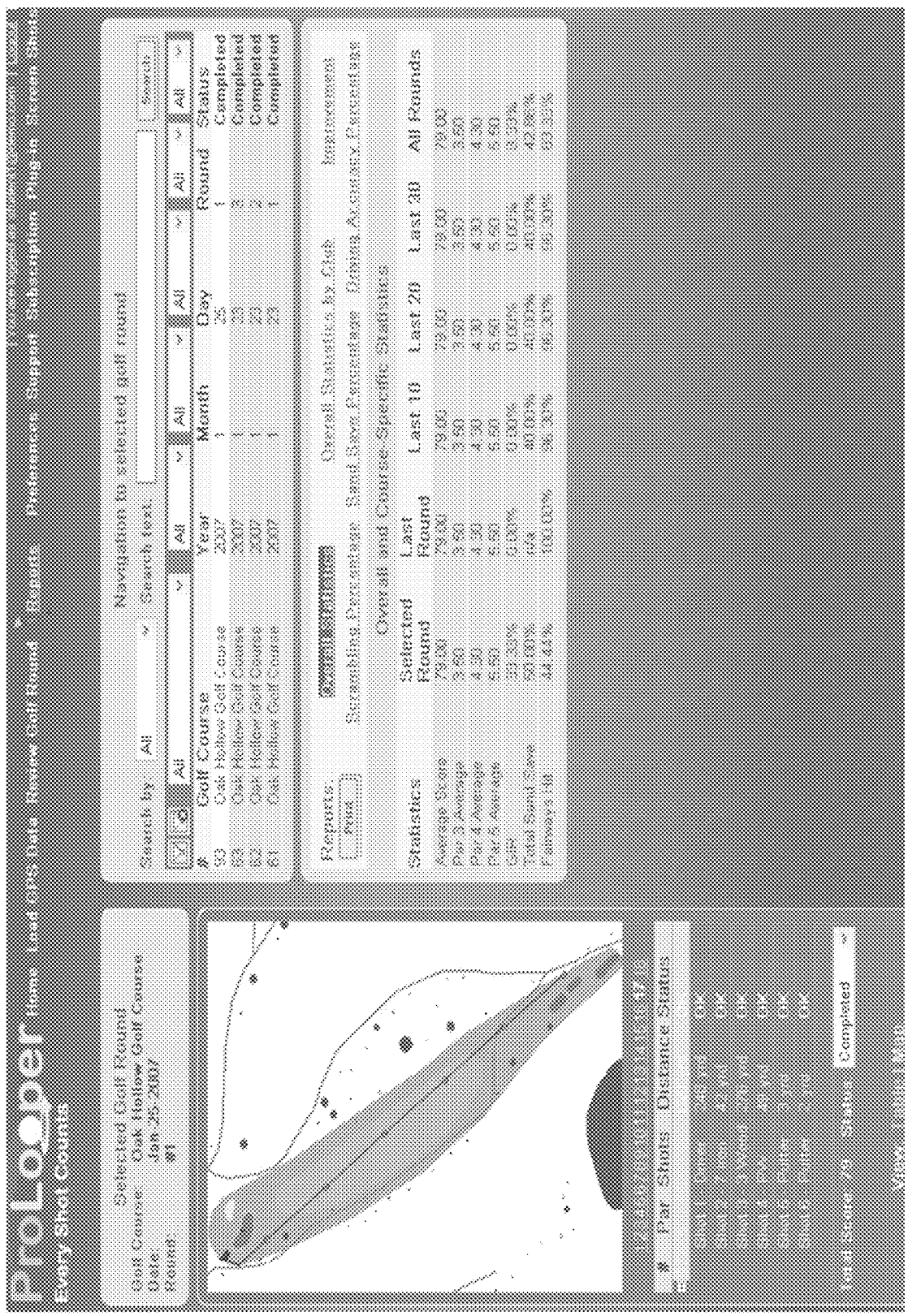
FIG. 17 illustrates a user interface for entering information and viewing analytical outputs according to one embodiment of the present invention.

The first report is the Overall Statistics mode. It shows the selected round (the system is configured to display any one round from a golfer's entire history), the last round, then the past 10, 20, 30, and all rounds to the right. The Overall Statistics mode includes stats for score, average score on the various pars, greens in regulation (GIR), sand save percentage, and driving accuracy percentage. The Reports section, as illustrated in FIG. 17, also is configured to filter rounds so only certain rounds are displayed. Additionally, the Reports section is further operable to filer rounds based on course, year, month, and day.

Figure 18:
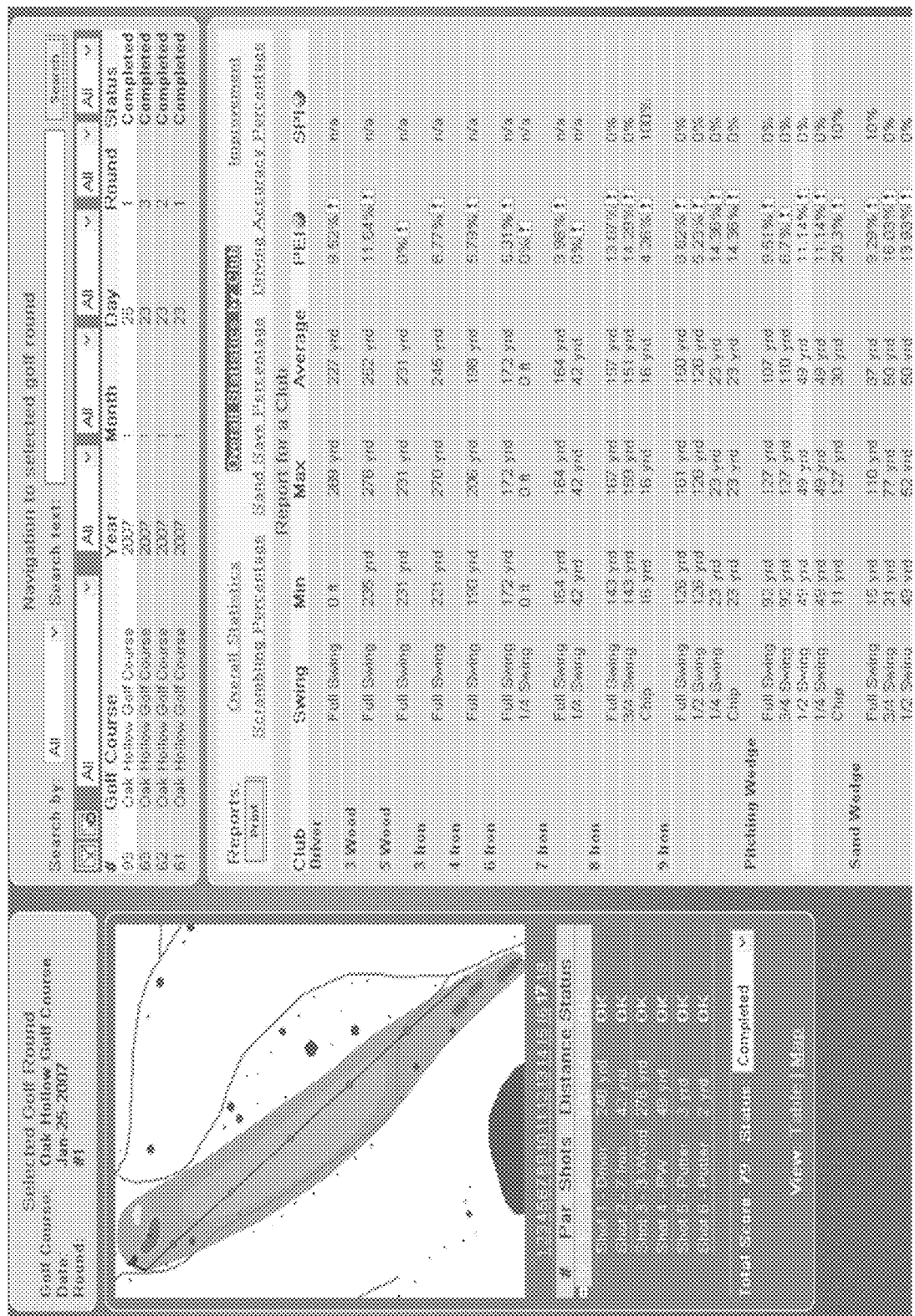
FIG. 18 illustrates a user interface for entering information and viewing analytical outputs according to one embodiment of the present invention.

FIG. 18 provides a screen shot view showing an Overall Statistics by Club report. The Overall Statistics by Club report includes the minimum, maximum, and average distances for each club (and type of swing) that a golfer used. The PEI (Percentage Error Index) shows how far a golfer missed a target. For example, if a golfer had 100 yards to the pin, and hits a shot 10 yards away, the PEI is 10%. SPI (Scoring Percentage Index) is a percentage of how often a golfer hits a shot to within 6 feet of the hole.

Figure 19:
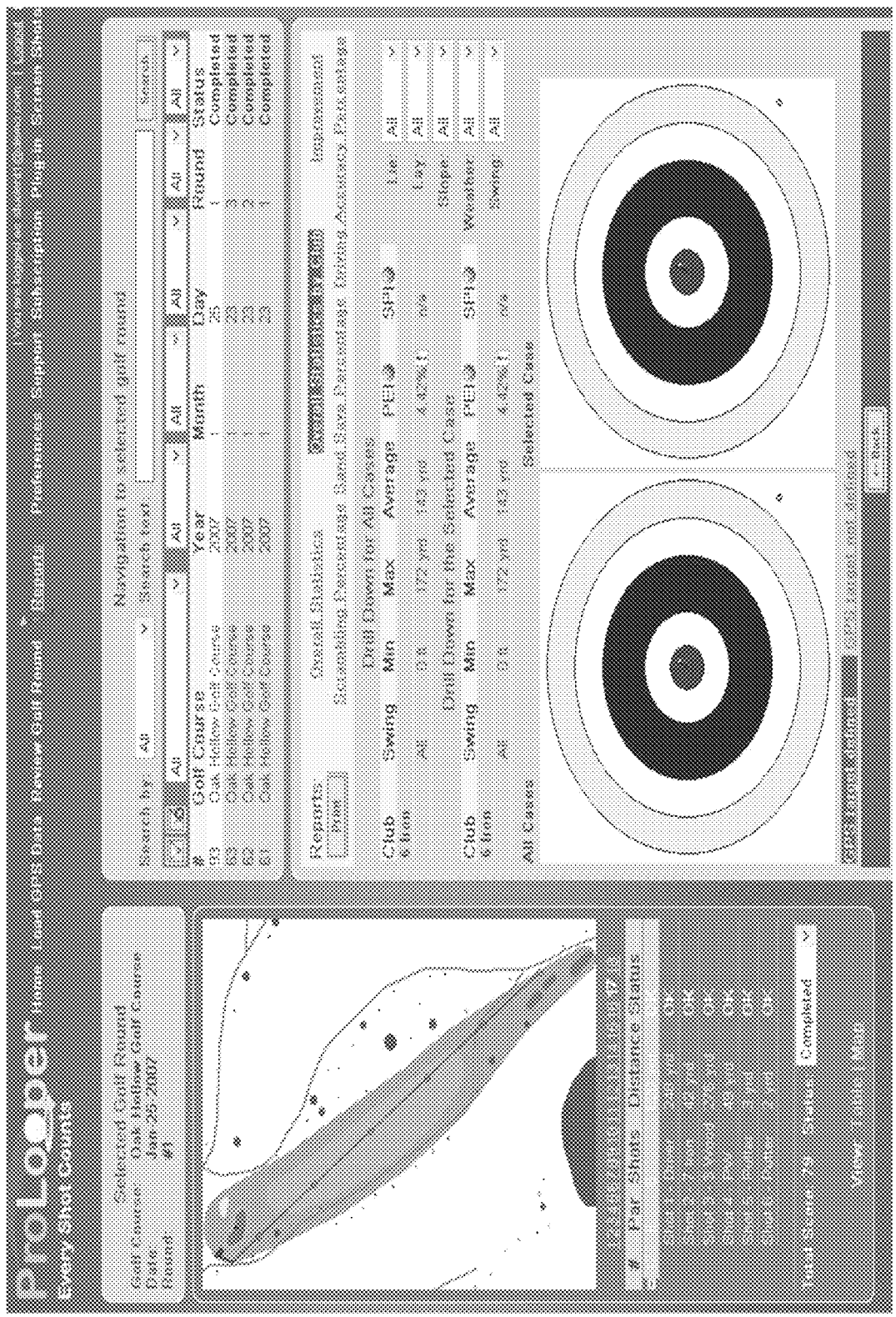
FIG. 19 illustrates a user interface for entering information and viewing analytical outputs according to one embodiment of the present invention.

From the same report, as illustrated in FIG. 19, the interface is operable to receive a selection of a club. The system is operable to display data relating to the accuracy of each club. The system is configured to display club accuracy in relation to a flagstick. Only shots that have a target of "Flagstick" will be displayed. The system is further operable to display a chart that includes all shots with that club. The system is further operable to filter the displayed club information based on course location, starting position, lie position, and other similar information. For example, and not limitation, the right chart is configured further dialed down by clicking the drop-down boxes on the right side of the screen. The system is configured to only display shots out of a fairway bunker, off an uphill lie, out of heavy rough, etc. based on user input.

Figure 20:
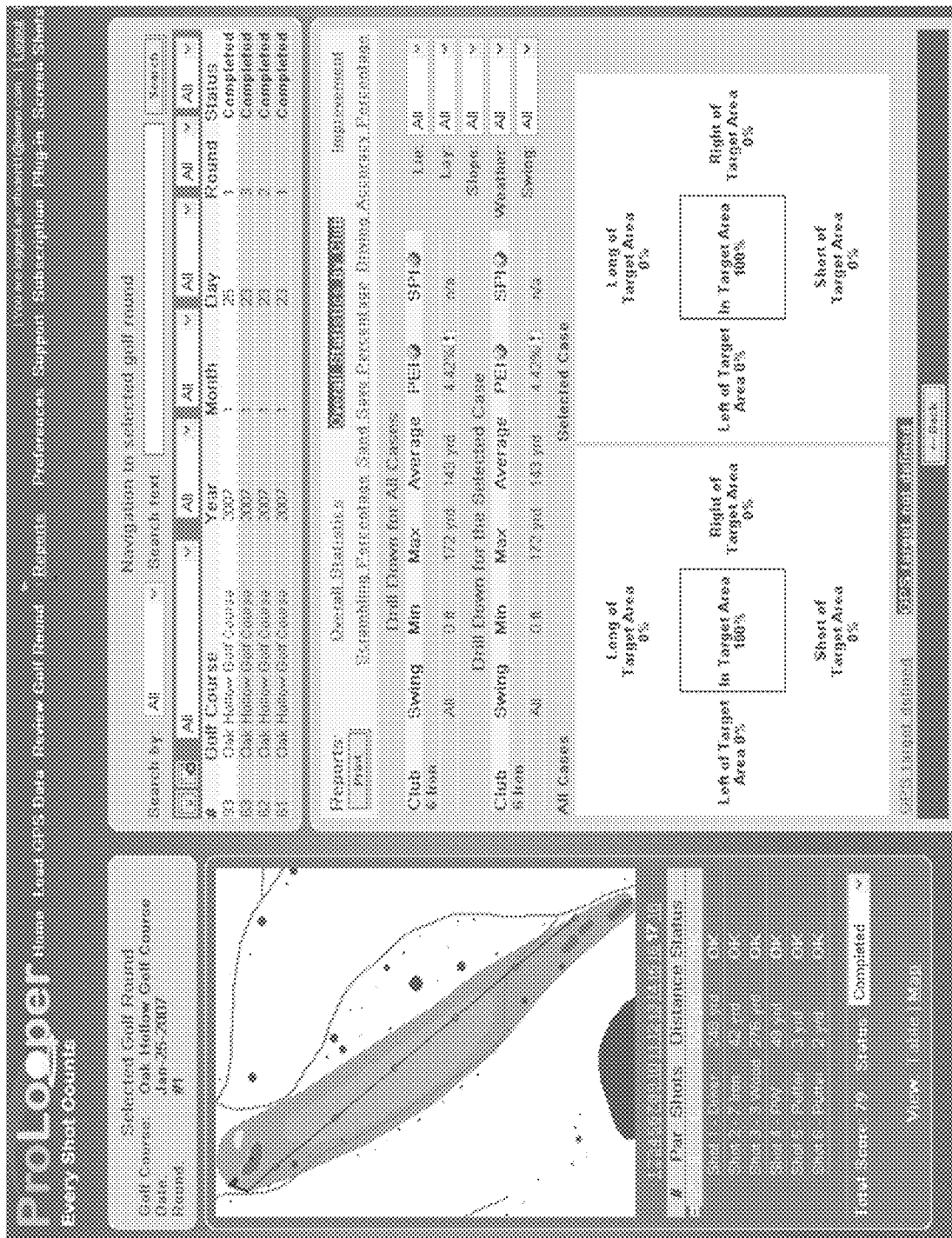
FIG. 20 illustrates a user interface for entering information and viewing analytical outputs according to one embodiment of the present invention.

For those shots that are not targeted at a point, the present invention includes a label for indicating a "Target Area" or "Target Zone." By receiving a user selection for the link below the charts as illustrated in FIG. 20 that is labeled "GPS target not defined," the system is configured to display the indicated user interface and graphics. Target are configured to be defined as described supra. Same goes for the left chart showing all shots for that club, and the right being selectable. Shot information with a particular club is stored and the system is operable to use the club shot information when providing target recommendations when the same club on the same course is selected in the future.

Figure 21:
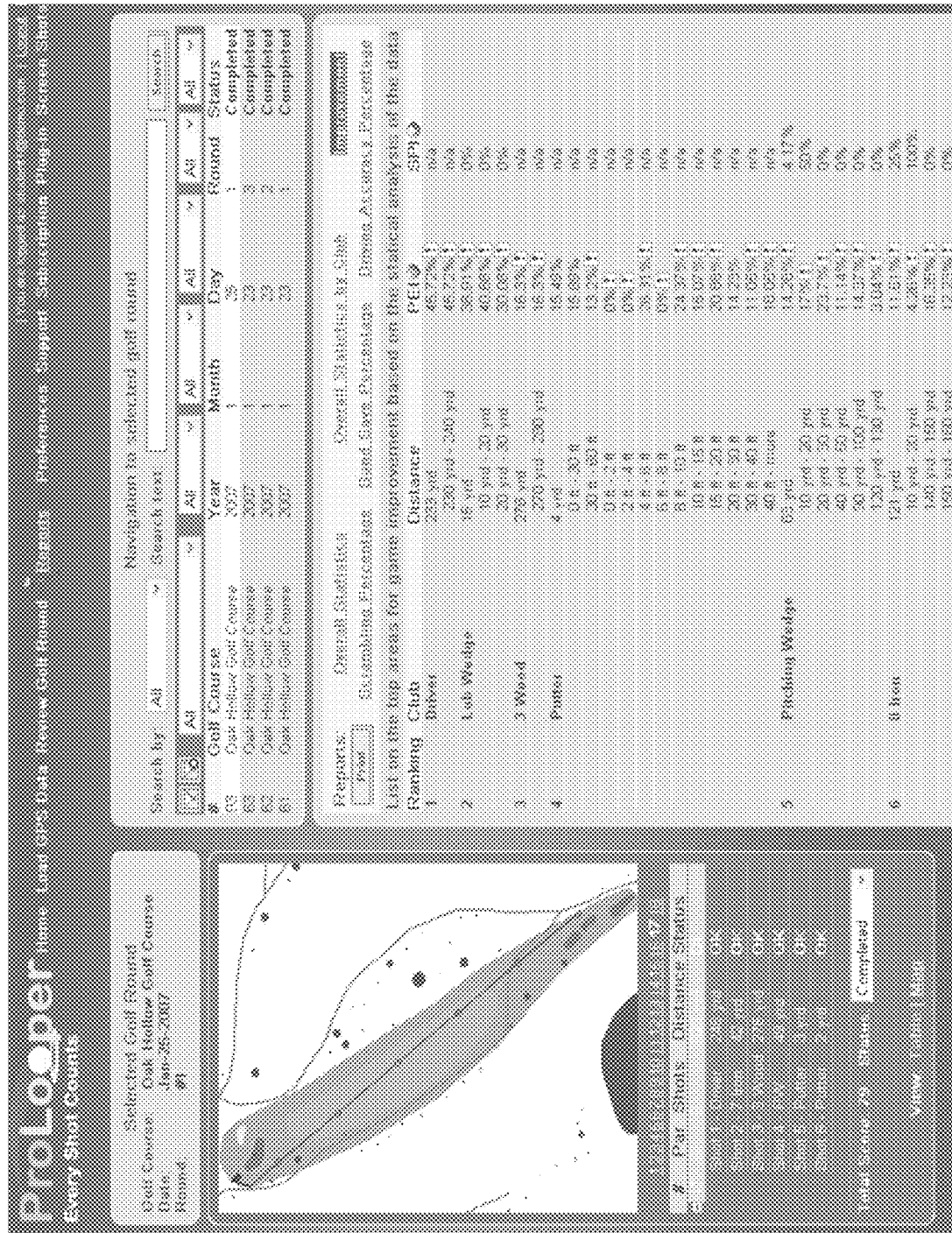
FIG. 21 illustrates a user interface for entering information and viewing analytical outputs according to one embodiment of the present invention.

The next report shown in FIG. 21 is the Improvement report. The Improvement report includes a list of clubs, with the clubs that have the highest error percentage at the top. The higher the PEI, the worse a golfer is with that particular club. The higher PEI clubs indicate the clubs that need the most improvement.

Figure 22:
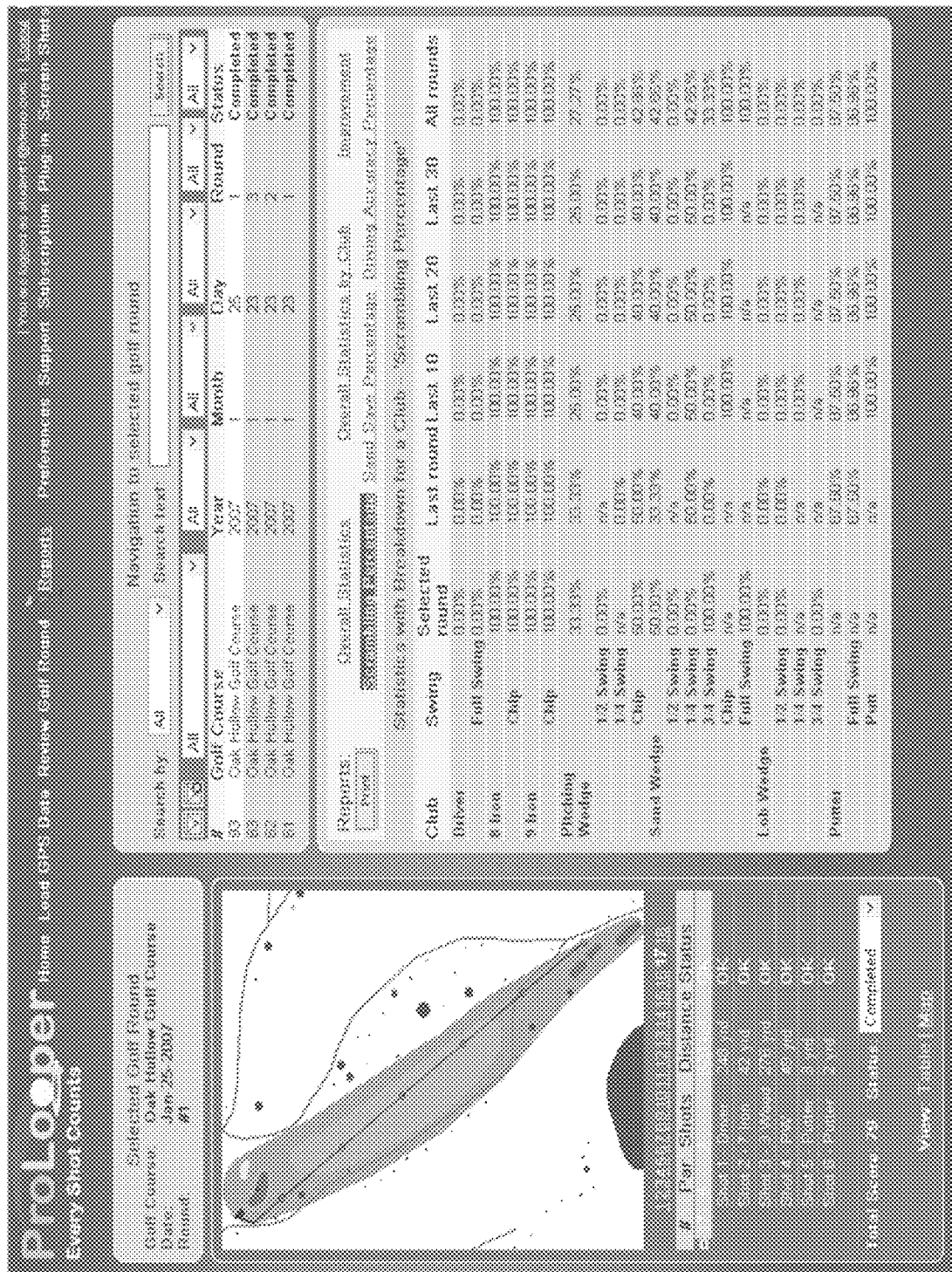
FIG. 22 illustrates a user interface for entering information and viewing analytical outputs according to one embodiment of the present invention.
Figure 23:
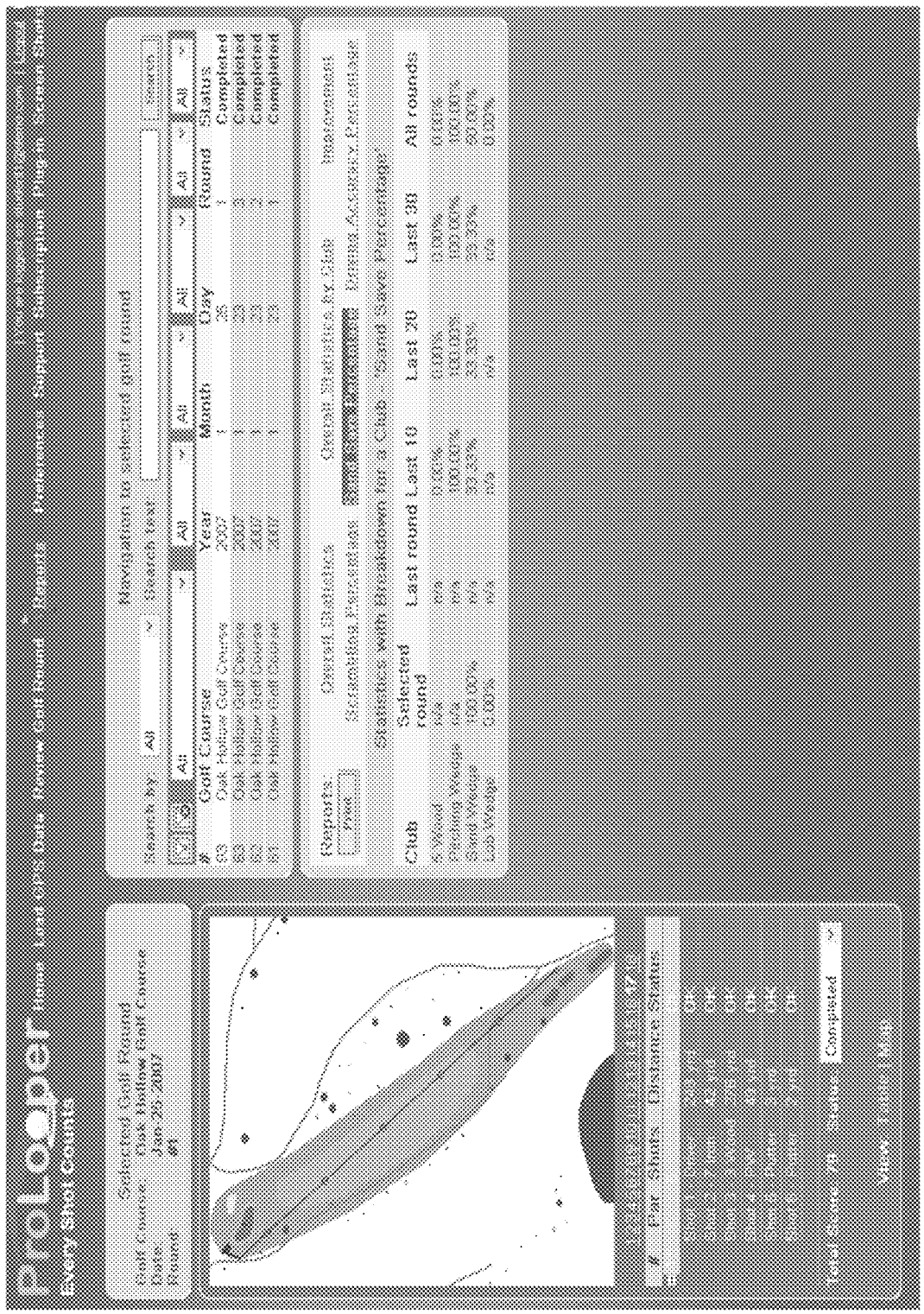
FIG. 23 illustrates a user interface for entering information and viewing analytical outputs according to one embodiment of the present invention.
Figure 24:
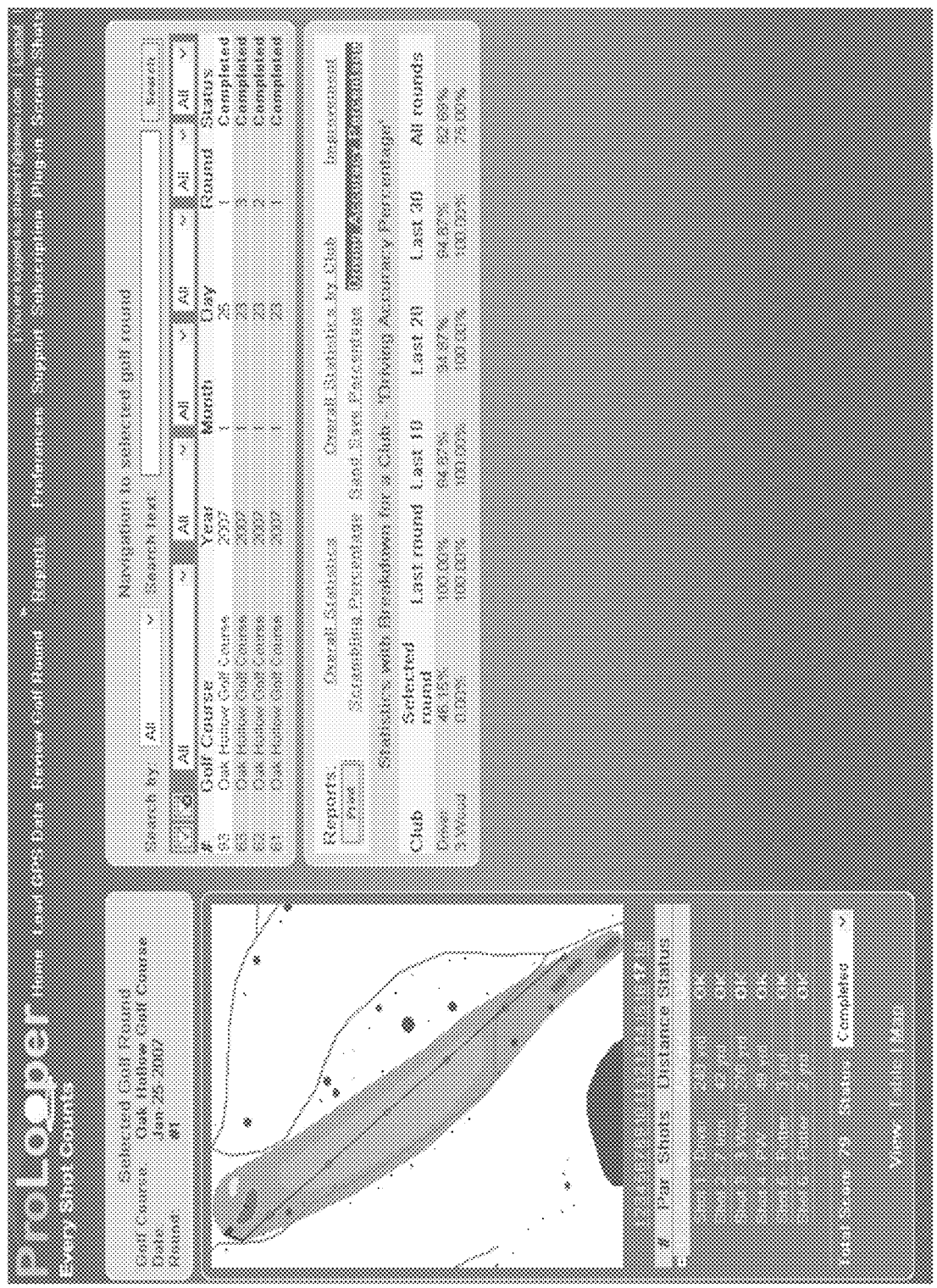
FIG. 24 illustrates a user interface for entering information and viewing analytical outputs according to one embodiment of the present invention.

The next report illustrated in FIG. 22 shows a Scrambling Percentage report. This shows how often a golfer makes par when the golfers misses a green in regulation. Sand save reports show how often a golfers gets up and down out of a green-side sand bunker, as illustrated in FIG. 23. Driving Accuracy shows how often a golfer hits the fairway from the tee, as illustrated in the screen shot from the web-based user interface for FIG. 24.

Figure 25:
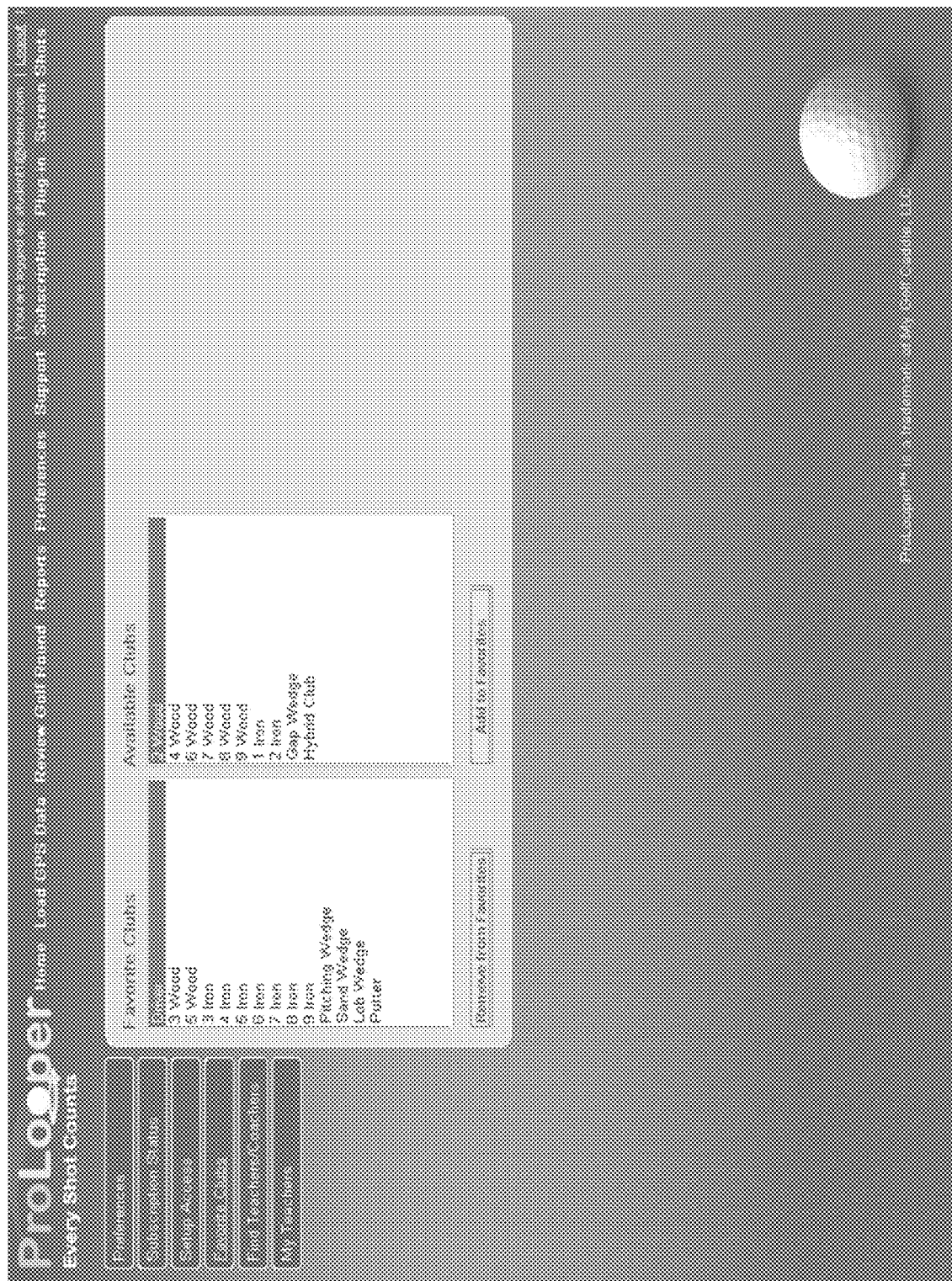
FIG. 25 illustrates a user interface for entering information and viewing analytical outputs according to one embodiment of the present invention.

The system and methods of the present invention also provide for options that permit a golfer to set up favorite clubs, which prevents the golfer from having to scroll through the entire list of clubs when reviewing shots on the user interface; this is illustrated in FIG. 25. To edit the properties of a particular shot, the system is configured to receive user input. The system is configured to receive situational data such as lie, lay, slope, club, type of swing, weather information, etc.

Visualizations

The present invention provides diagrammatic visualization of a target zone or area versus pinpoint target for a user providing inputs to the device, preferably the inputs being made during the course of play on a golf. The systems and methods of the present invention further provide access to statistical analytics and graphical user interfaces provided by software running on a remote server computer in communication with the user's computer via a network, preferably the web (WWW).

The present invention is configured to provide detailed diagrammatic representations of golf performance analytics, such as scattergraph diagrams, that provide information including area and zone targets rather than merely pinpoint targets, and wherein the directionality of each shot is zeroed to facilitate identification of direction-based errors. Therefore, the present invention provides for situation-neutral golf metrics that are useful regardless of whether the application user is playing on a course or in a practice setting.

Preferably, the graphical visual representation(s) includes scattergraph diagrams and/or shot zone diagrams that identify errors and trends based upon the inputs for the at least one golf shot. Preferably, in one embodiment, the diagrams are interactive via the GUI or display. Also, the system is configured to display the diagrams in a portable, printed pocket-sized version of the diagrams viewable on the GUI or display. In any format, the diagrams include shot accuracy based upon the at least one golf shot inputs for indicating performance for an individual golfer based upon a specific club and golf course situations, and past performance, along with statistical likelihood for present performance under similar conditions. The inputs include coordinates of a series of corresponding starting points and targets, recordation of actual shot locations from those starting points, and wherein the outputs include statistical analysis having text, tabular, diagrammatic, and/or image-based outputs that are converted from the inputs. The handheld device includes a purpose-built golf GPS device or a mobile communication device, including but not limited to smart phones or mobile phones.

Regarding visualization of data, different visualization options of the shot data and related analytics are available, including tabular and map-type views, that are selectively reviewable via the device, or on a remote computer connected to the server via the network, connected to the web. Additional shot-by-shot views and statistics are optionally reviewable via the device by the user and/or a third party with permission for such review. In addition to the primary information, the system is configured to receive secondary information, including but not limited to slope of the landscape between the ball and the inputted target, ball position on that landscape, wind direction, wind strength, precipitation, humidity, penalty strokes, altitude, player status (such as injury, sickness, etc.), three-dimensional ball position, and combinations thereof.

For scatter graph generation as shown in FIG. 1, the present invention systems and methods select shots made by a user using a specific golf club and for which flagstick is the target (in this case, a pinpoint target). Then the coordinates of the flagstick are projected for each shot in 0 point and find the distance from 0 point to: Pn(x)—distance in X-direction, Pn(y)—distance in Y-direction.

X-Direction Distance Calculation. The distance from target to shot in X-direction is calculated as follows: The reference point is taken as the coordinates of flagstick, to which the shot was targeted. The end point is Pn(x), which is calculated as: Pn(x)Longitude=Shot n Longitude Pn(x) Latitude=Target n Latitude Y-Direction Distance Calculation. For calculating distance from target to shot in Y-direction the similar method is used. The reference point is taken as the coordinates of flagstick, to which the shot was targeted. The end point is Pn(y), which is calculated as: Pn(y)Longitude=Target n Longitude Pn(y)Latitude=Shot n Latitude Positioning Shot by X, Y Coordinates. After the coordinates of Pn(x), Pn(y) have been found, the system is configured to calculate the distances from Pn(x), Pn(y) points to the Target, which are the distances of n-shot in X, Y directions. The distances are calculated with the help of GeoFrameworks library. Next, the system is operable to find the position of Pn(x), Pn(y) point relative to 0 point. The system is configured to determine the hemisphere of GPS coordinates. If hemisphere is South or West then the system gives those coordinates a negative sign.

If Longitude of Pn(x) point is larger than Longitude of 0 point, it means that the point is located on the right (to the east).

If Latitude of Pn(y) point is larger than Latitude of 0 point, it means that the point is located higher (to the north).

For instance, the following GPS Coordinates are received: End shot point latitude (2649.4087,N); End shot point longitude (08006.9080,W); Hole point latitude (2649.4087, S) Hole point longitude (08006.9100,W). To determine the position of the shot point relative to the hole by Y axe, the system is configured to use a shot point latitude with a positive sign (because it's North hemisphere) and compare it with hole point latitude with negative sign (because it's South hemisphere). 2649.4087 is greater than (−2649.4087). So point is located higher (to the north). The same algorithm for determining the position by X axe. But in this case the West hemisphere is negative and the East is positive.

Updates to Support Direction of Play on Scatter Graph

Figure 2:
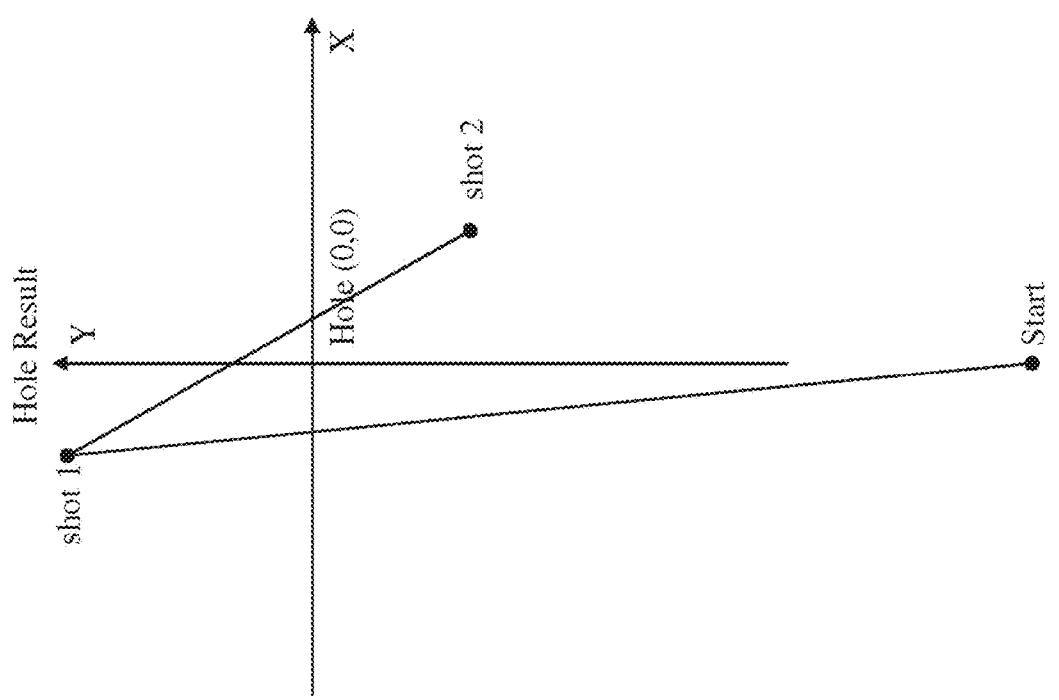
FIG. 2 includes a schematic diagram illustrating a diagrammatic representation of golf performance analytics in accordance with one embodiment of the present invention.
Figure 3:
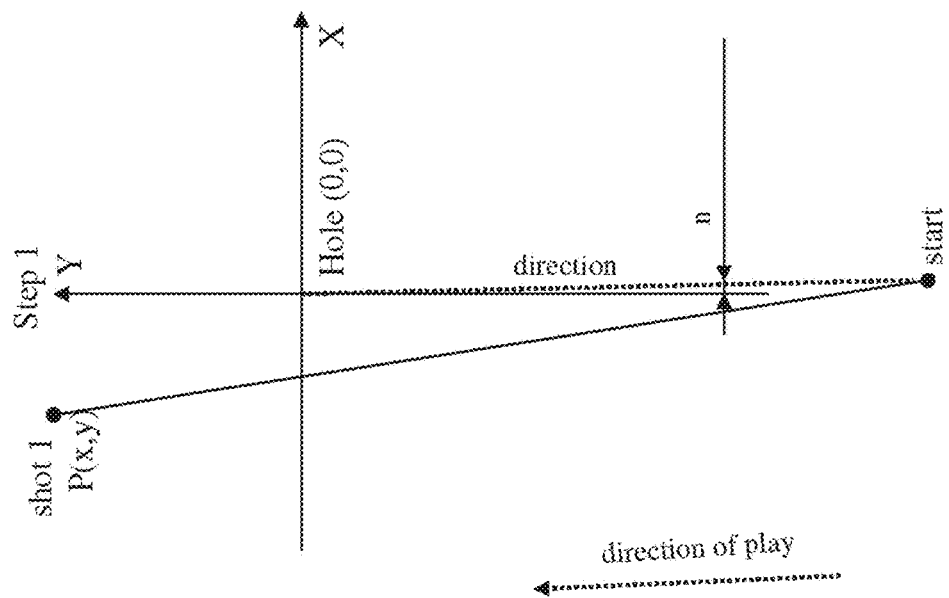
FIG. 3 includes a schematic diagram illustrating a diagrammatic representation of golf performance analytics in accordance with one embodiment of the present invention.
Figure 4:
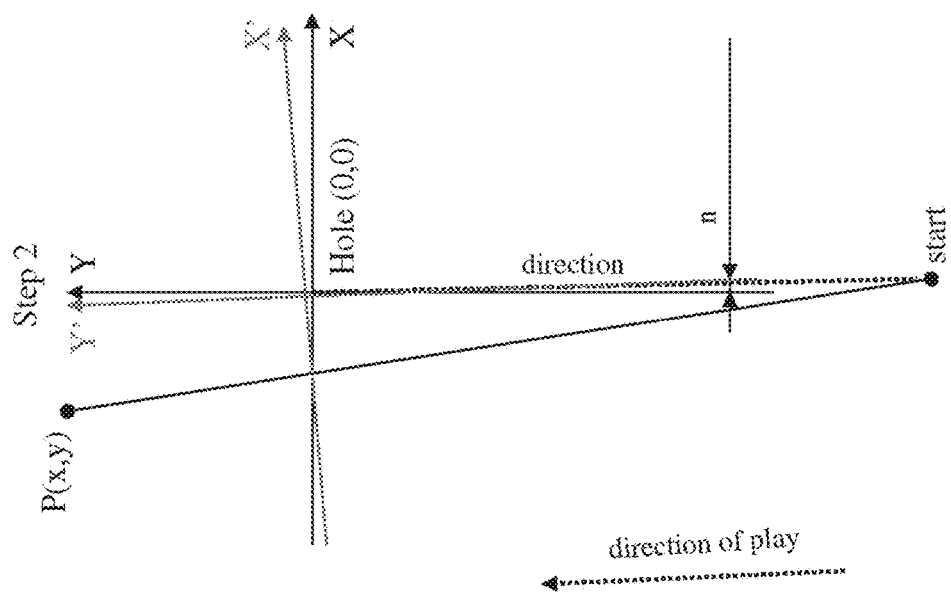
FIG. 4 includes a schematic diagram illustrating a diagrammatic representation of golf performance analytics in accordance with one embodiment of the present invention.
Figure 5:
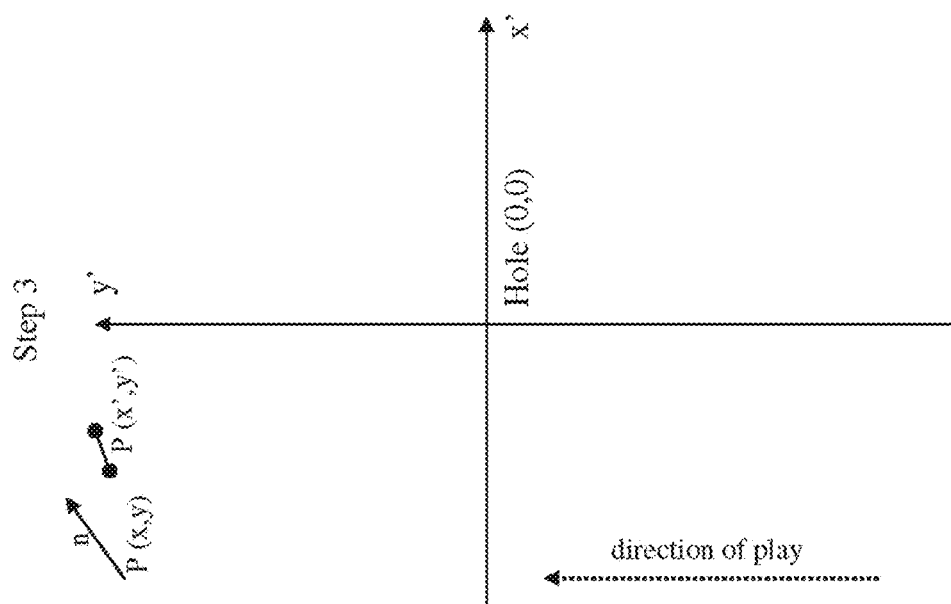
FIG. 5 includes a schematic diagram illustrating a diagrammatic representation of golf performance analytics in accordance with one embodiment of the present invention.
Figure 6:
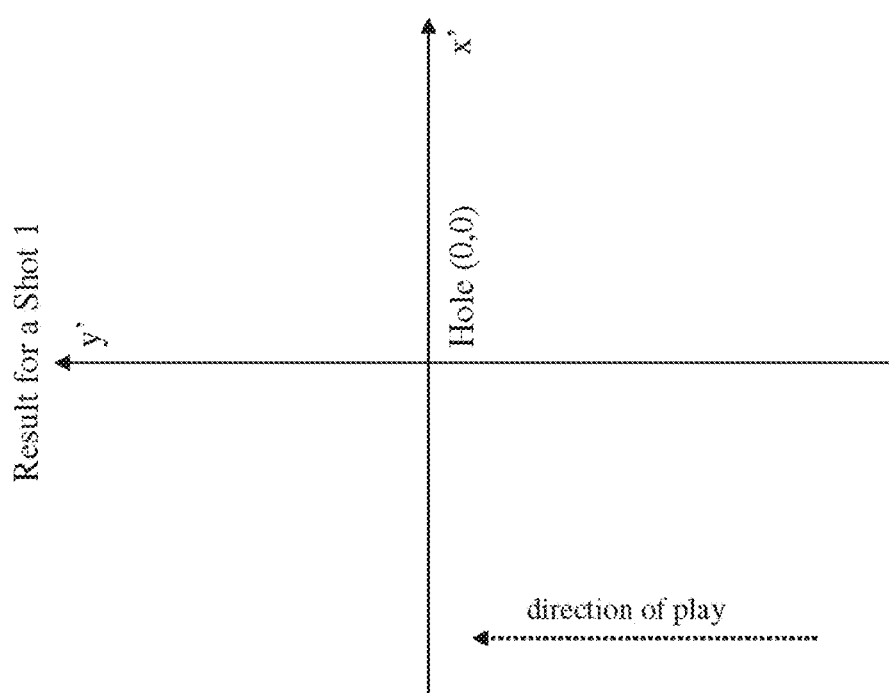
FIG. 6 includes a schematic diagram illustrating a diagrammatic representation of golf performance analytics in accordance with one embodiment of the present invention.
Figure 7:
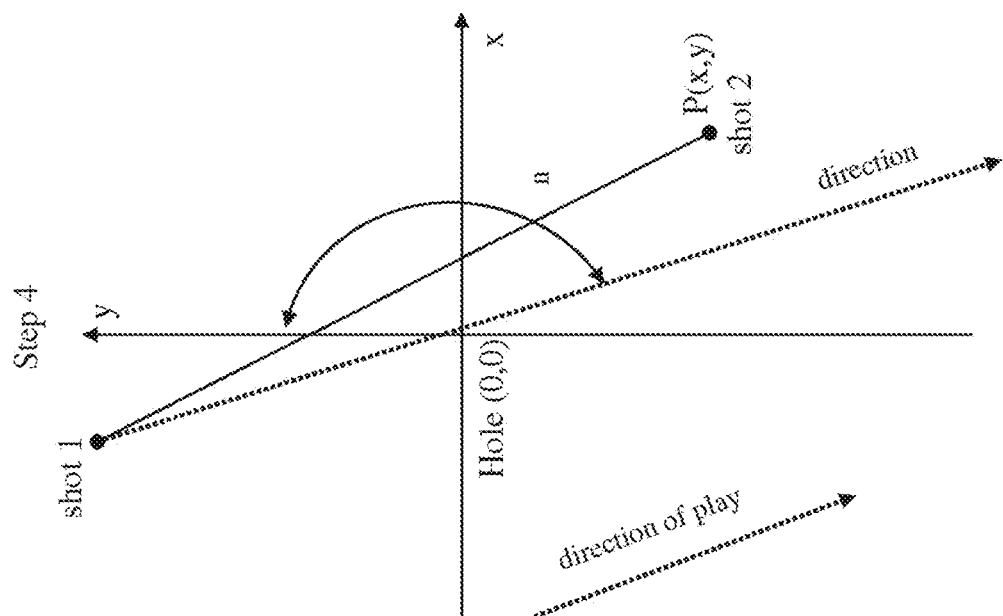
FIG. 7 includes a schematic diagram illustrating a diagrammatic representation of golf performance analytics in accordance with one embodiment of the present invention.
Figure 8:
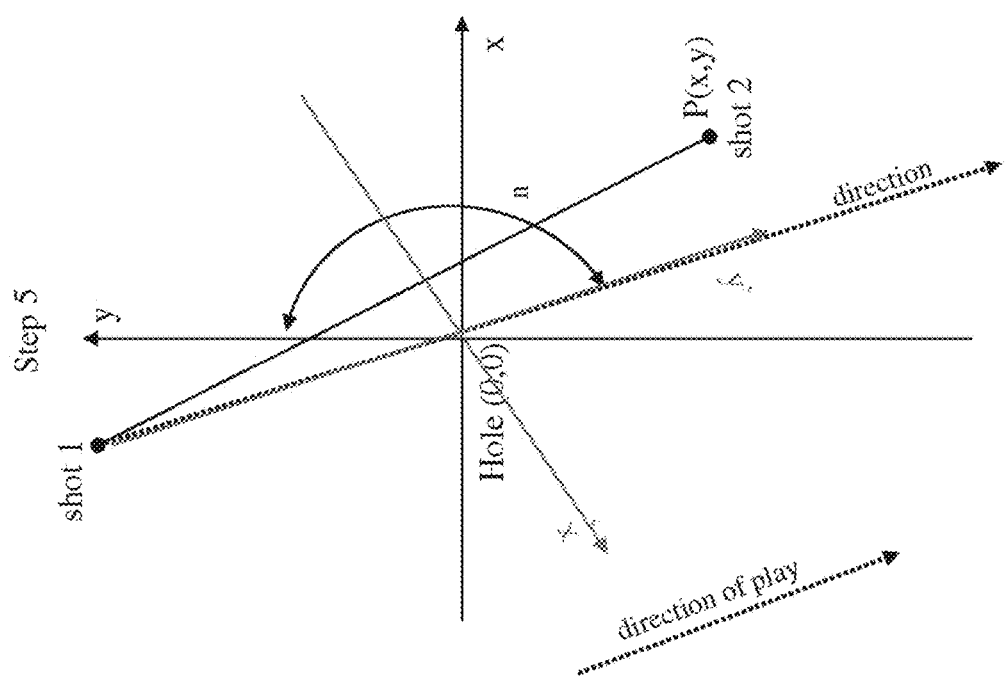
FIG. 8 includes a schematic diagram illustrating a diagrammatic representation of golf performance analytics in accordance with one embodiment of the present invention.
Figure 9:
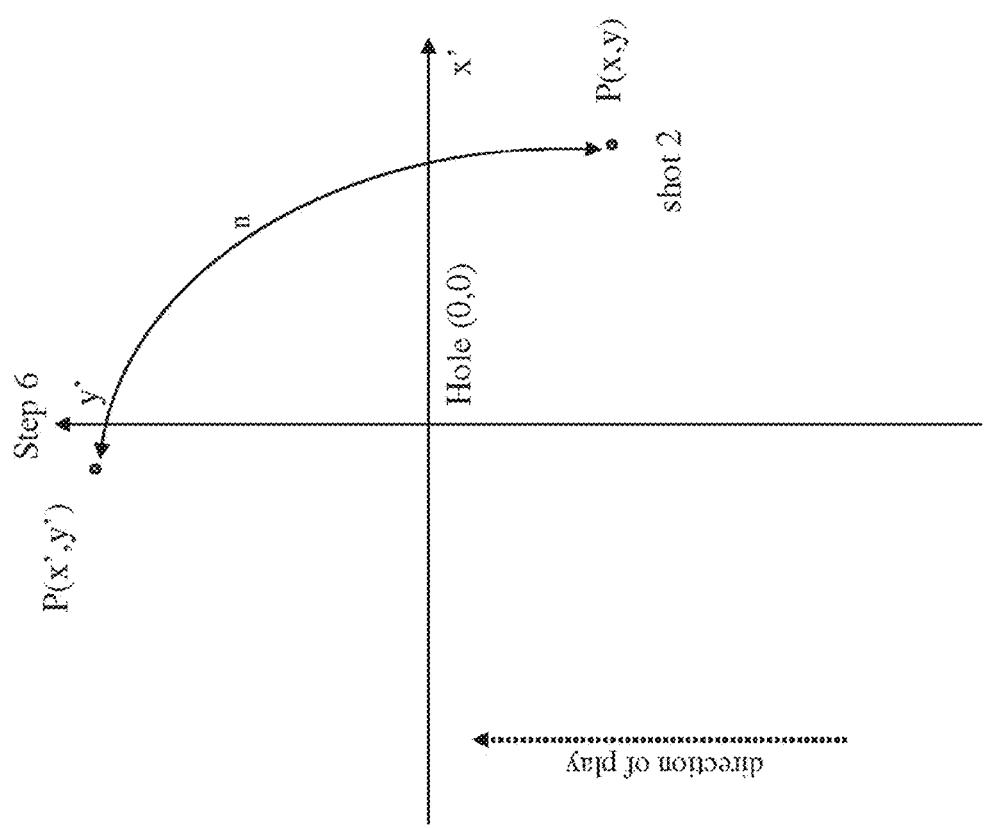
FIG. 9 includes a schematic diagram illustrating a diagrammatic representation of golf performance analytics in accordance with one embodiment of the present invention.
Figure 10:
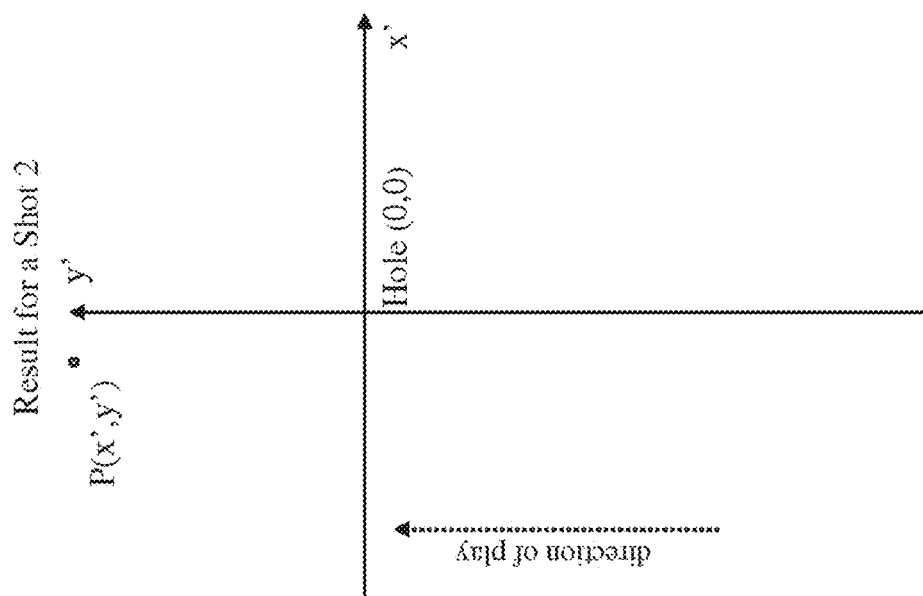
FIG. 10 includes a schematic diagram illustrating a diagrammatic representation of golf performance analytics in accordance with one embodiment of the present invention.
Figure 11:
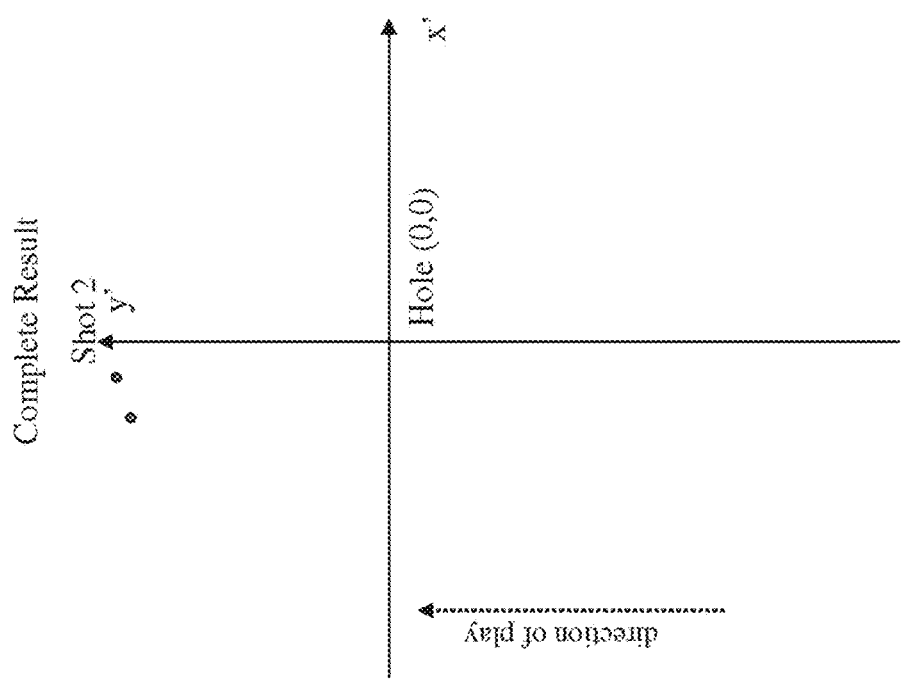
FIG. 11 includes a schematic diagram illustrating a diagrammatic representation of golf performance analytics in accordance with one embodiment of the present invention.
Figure 13:
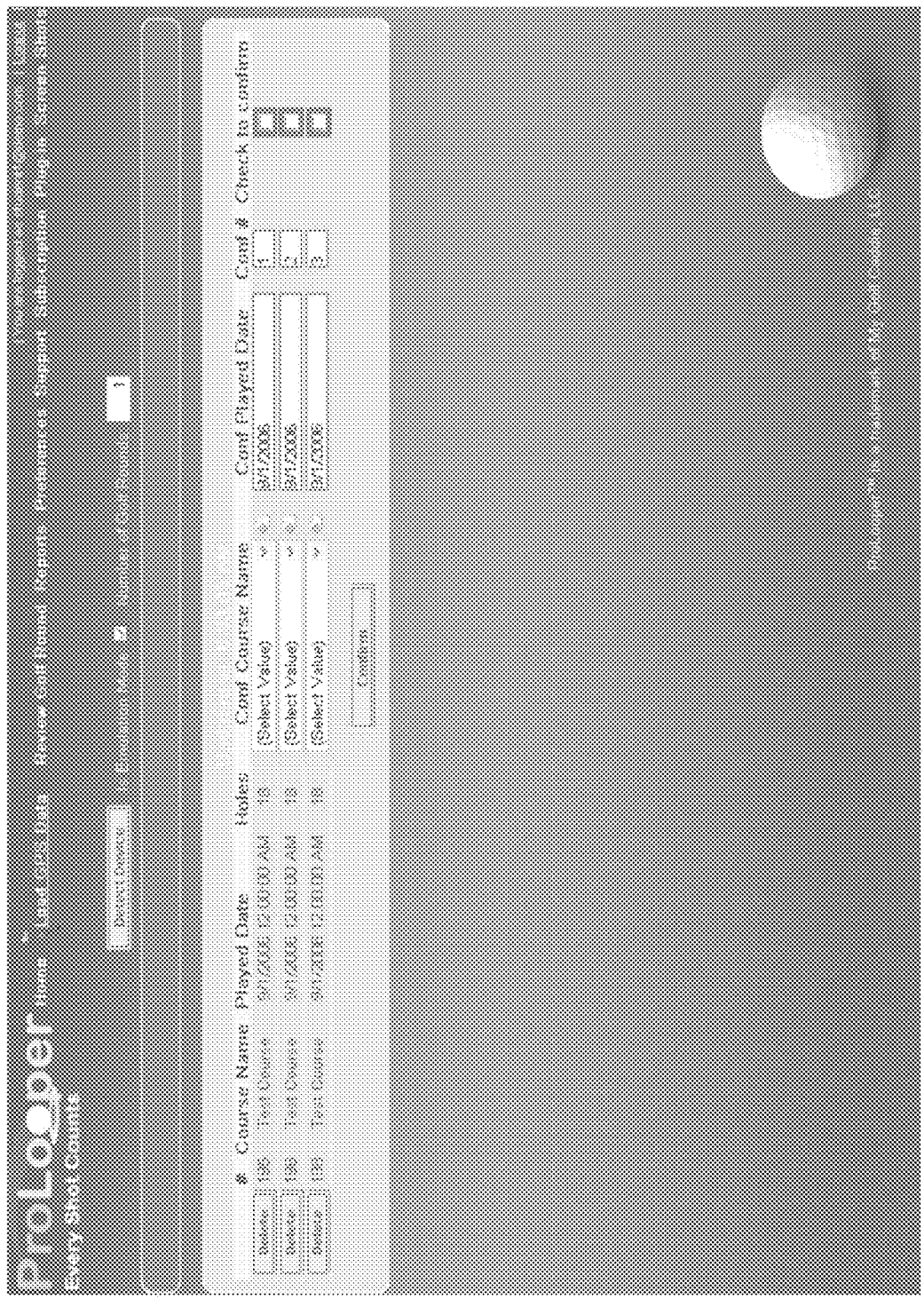
FIG. 13 illustrates a user interface for entering information and viewing analytical outputs according to one embodiment of the present invention.
Figure 14:
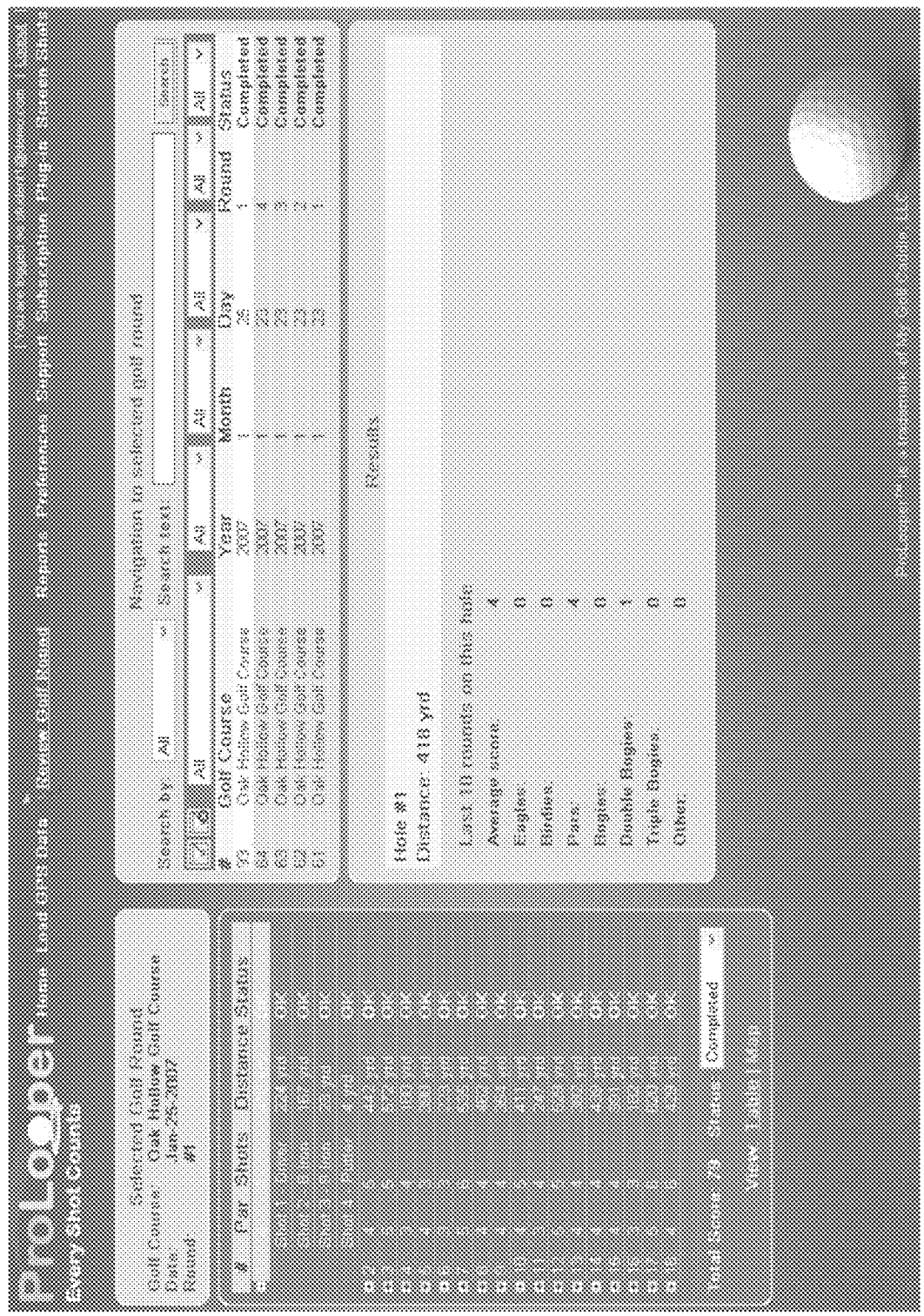
FIG. 14 illustrates a user interface for entering information and viewing analytical outputs according to one embodiment of the present invention.

On FIG. 2, hole result is depicted. For graph calculation and diagram generation, the target for each shot is projected in point (0, 0). Then, by algorithm described in FIG. 2, the coordinates of point for each shot are calculated. FIG. 3 illustrates how the direction of the shot is found, as in Step 1. FIG. 4 shows the turning angle being found relative to the initial axes of reference, as in Step 2. FIG. 5 provides illustration of a Step 3, wherein the axes X', Y' and shot point are turned through angle n.degree, resulting in a graph illustrated in FIG. 6, showing a result for a shot 1 or a first shot. A similar method is used for generating the point of a second shot or subsequent shot, as shown in Step 4, Step 5, Step 6, Results for a shot 2 in FIGS. 7, 8, and 9, respectively, with the FIG. 10 showing a result for shot 2. Then, the graphs for each separate shot are merged together resulting in the complete Hole Result, illustrated in FIG. 11.

Printable Cards

In addition, the present invention provides a portable and preferably pocket-sized printed version of shot performance and/or statistical likelihood of present or future performance based upon past performance for any given golf club, golf course conditions, etc. Preferably, the shot zone diagrams provide a visual representation of statistical likelihood for any given shot based upon past performance. The shot zones preferably include a range of probability, such as 90%, 70%, and 50% likelihood. The shot zones are created based upon the actual past performance and/or based upon actual past performance plus a factor for variation and projection of likelihood of shot accuracy for the instant shot, depending upon conditions, etc. The past performance data is preferably selected from a predetermined range of time to include more than one past performance for an individual golfer. The shot zones are selected for play only on a given course (such as the same course being played at that time), or the shot zones are selected from all past play on any course. The data is updatable and can be stored on the device and printed from an electronic dataset that is preferably generated as set forth in the description infra. In any case, the shot zones are the best manner for the golfer to estimate how and where the golfer should take the shot, with which club, for the conditions present at that time. Thus, the pocket-sized, printed version of these diagrams provides a personalized shot book for an individual golfer that can be used during play on any course, even during tournament play.

It will be appreciated by one of ordinary skill that the current rules of golf do not allow for electronic devices to be used on the golf course during play. Therefore, the preferred embodiments provide for printed versions. However, it is included within the scope of the present invention that the shot zone diagrams are viewable and provided on electronic, handheld devices such as purpose-built GPS devices, mobile phones with graphical user interface screens, PDAs, and the like. These are currently available but are also currently not allowed during tournament play. Thus the "shot book" is intended to include electronic views not in printed, book or booklet form, but in screen shot or GUI viewable form.

In one embodiment, the shot zone of the present invention set forth hereinabove is supplemented with scattergraph diagrams as set forth herein. The system and methods of a preferred embodiment for determining the past performance of an individual golfer are set forth herein. It will be understood and appreciated by one of ordinary skill in the art that other methods, including manual recordation of past performance, can be used to generate the data from which the shot zone and the corresponding diagrams for a shot book are developed. The present best mode, however, provides that these are generated automatically, based upon data input during the golf round(s) using a hand-held GPS device and a software for inputting and analyzing the golf game data.

Coaching

Additionally, the golfer has review options provided on a GUI or display for reviewing, editing, modifying, and adding data to the uploaded shot data. In another embodiment, a method for providing statistical analytics of golf performance includes the steps of providing a GPS-operable device for receiving golf shot data during play on a course; uploading the golf shot data including GPS data to a computer having software for providing analysis of the data; and providing outputs including analytics of the data, wherein the outputs are viewable by the user via a GUI or display via text, tabular, graphic, and image-based outputs that include trends information for the golfer, all based upon actual golf play on course situations, wherein the golfer inputs shot data during play, without interrupting the flow of the game, and uploads the shot data for analytics via the GPS-operable device and review online. In such an embodiment, the analytics preferably include text, tabular, graphic, and image-based outputs that include trends information based upon the shot data input received via user input, wherein the shot data is based upon actual golf play on course situations, and the shot data is inputted during play.

Figure 26:
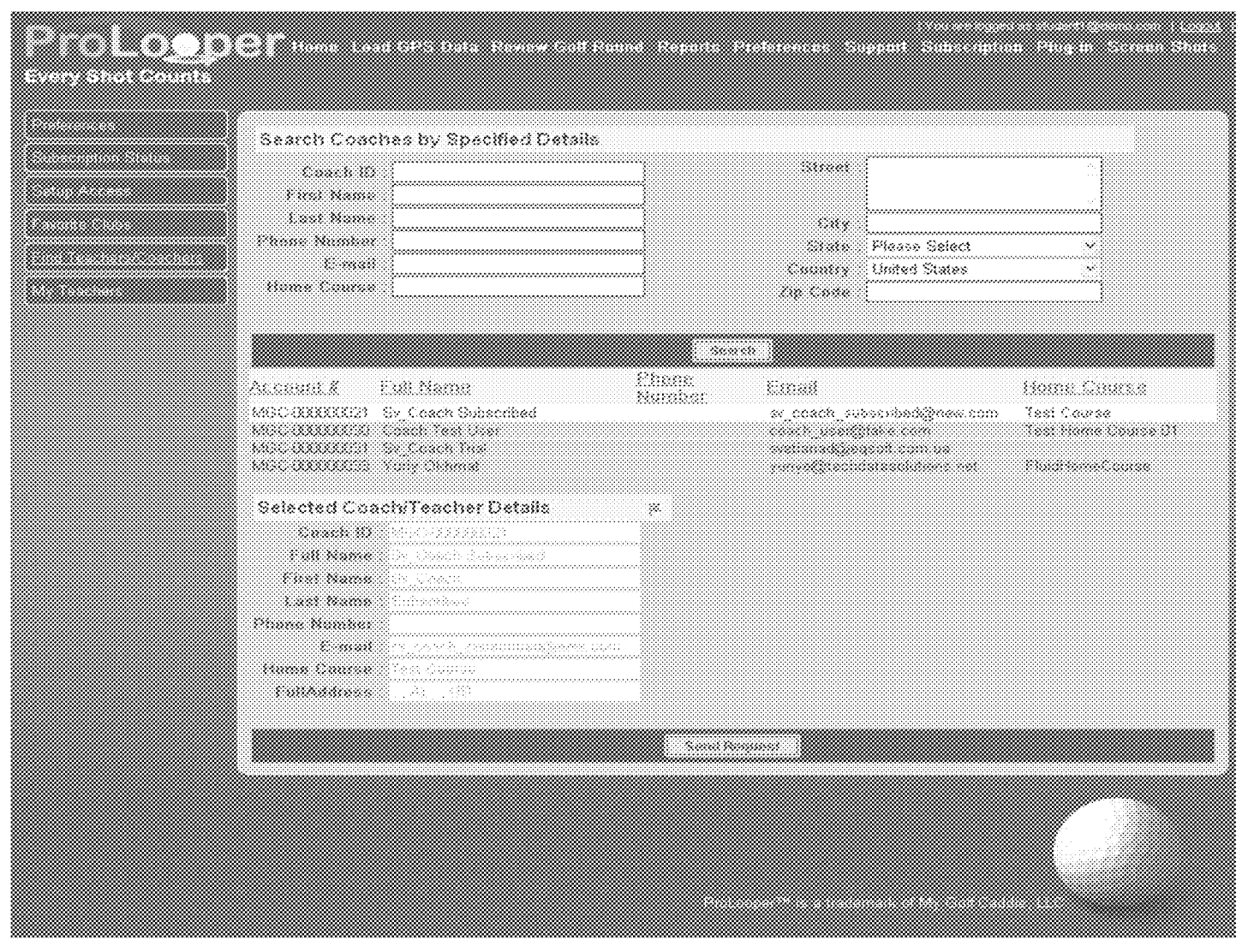

The system and methods of the present invention also provide functionality that permits a user to allow or provide access to another user such as their coach or a PGA professional. In one embodiment of the present invention, the system is configured to receive user input via a click-selection of the "Find Teachers/Coaches" link in the Preferences section (the system is configured to receive input from coaches and PGA Pros that identifies them as a coach/teacher). The system is configured for a golfer to search for a coach/trainer and send a request to the coach/trainer via the GUI, display or other input mechanism, as illustrated in FIG. 26.

Figure 27:
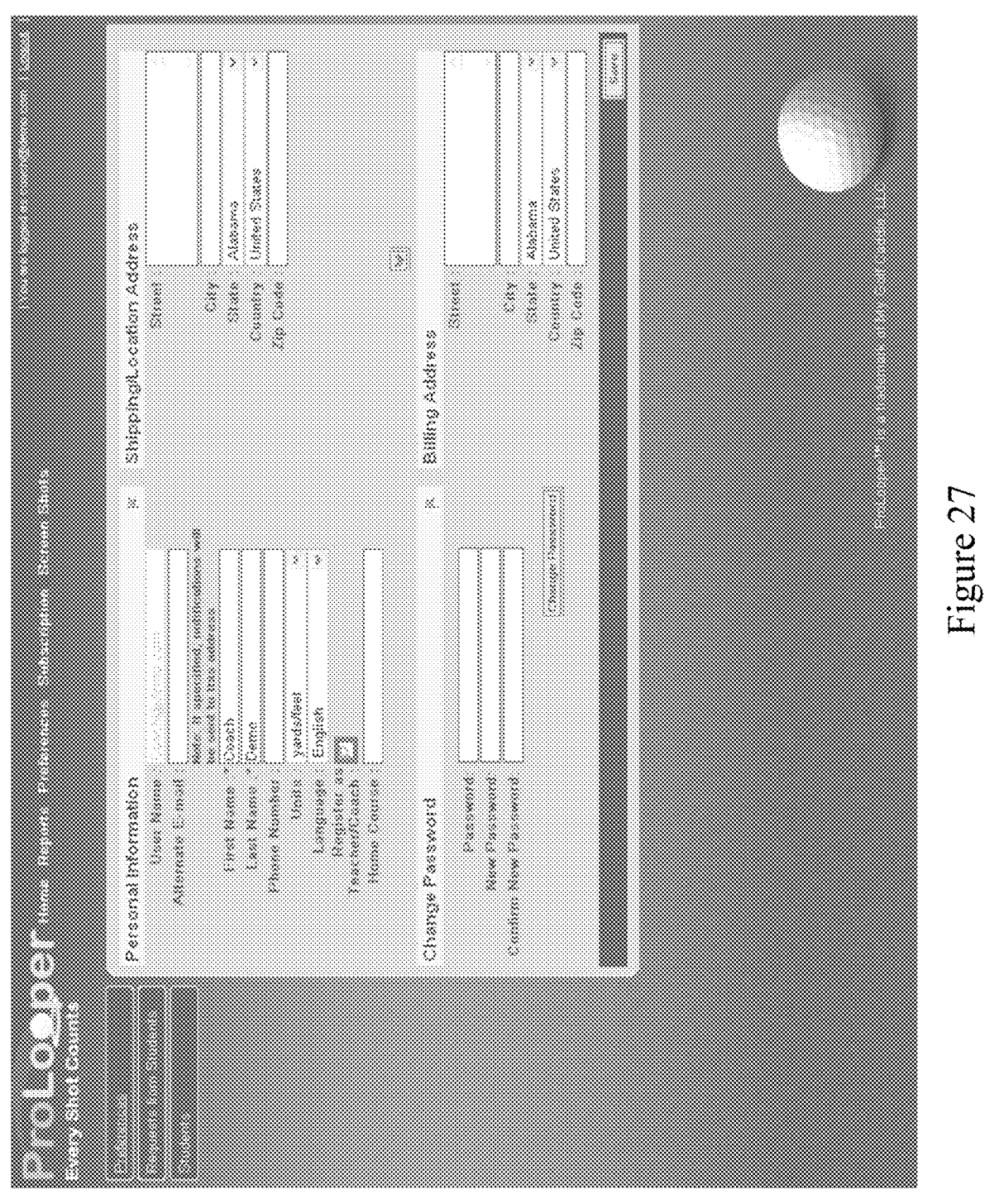
Figure 28:
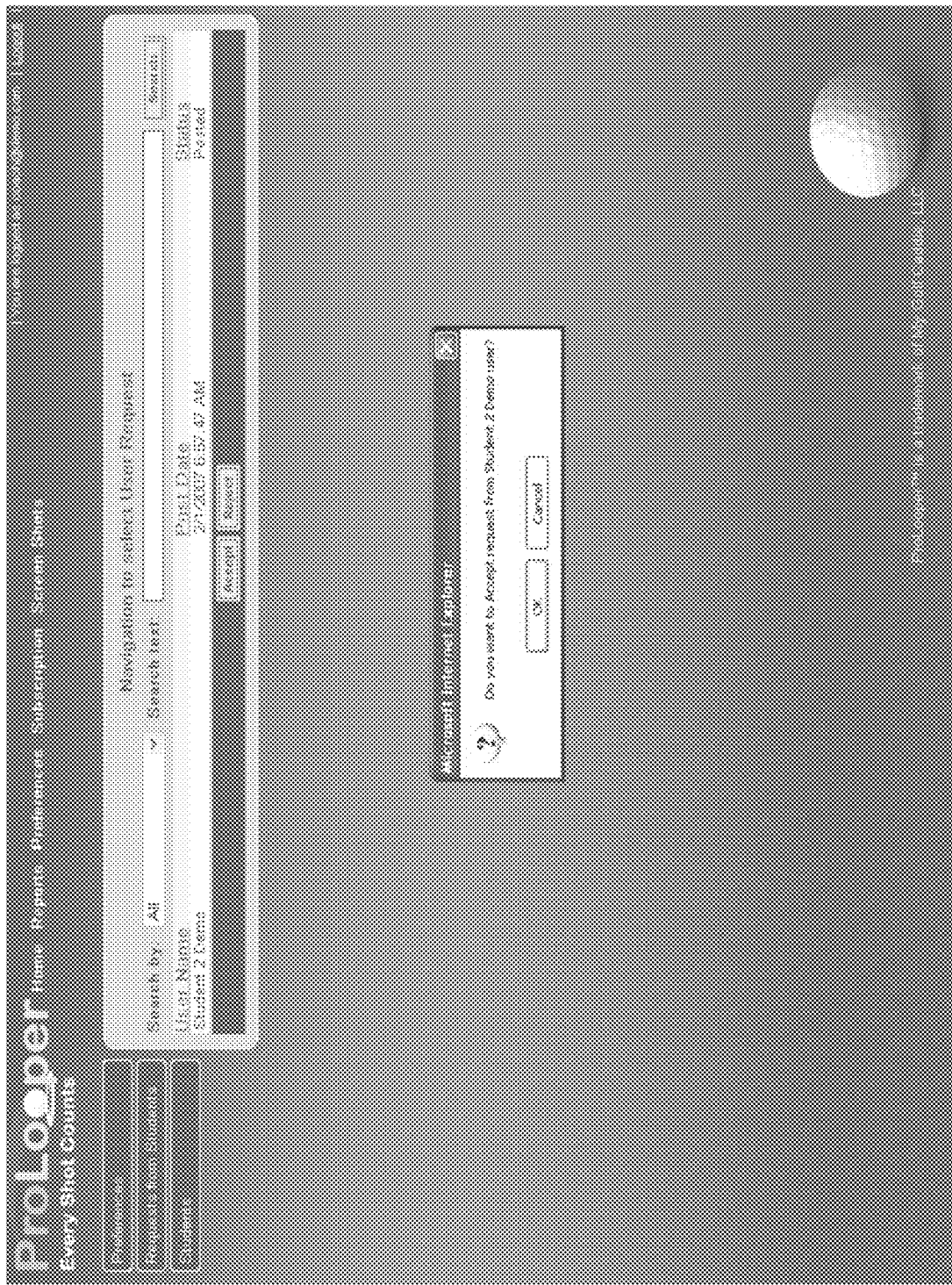
FIG. 28 illustrates a user interface for entering information and viewing analytical outputs according to one embodiment of the present invention.
Figure 29:
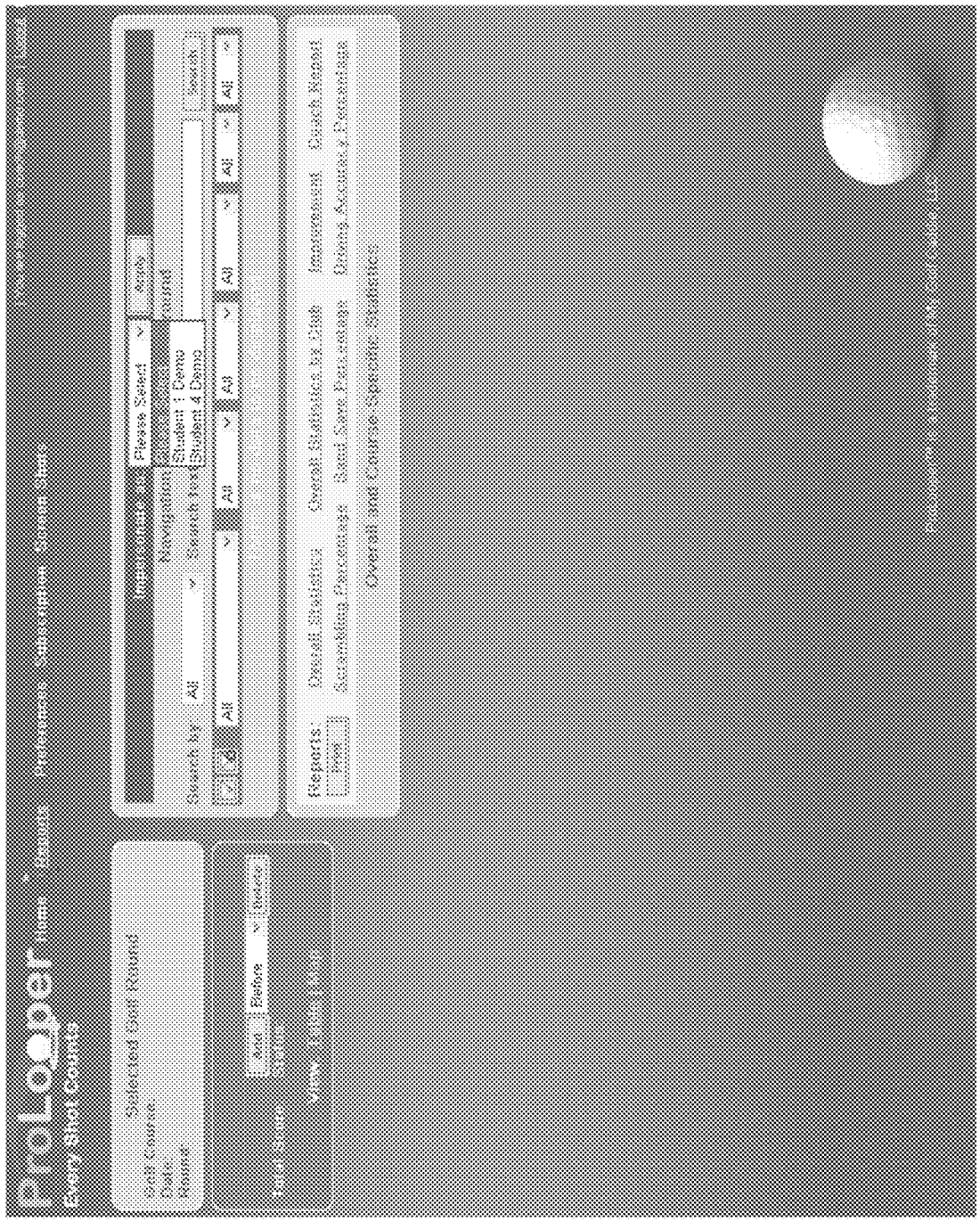
FIG. 29 illustrates a user interface for entering information and viewing analytical outputs according to one embodiment of the present invention.

FIG. 27 illustrates a graphical user interface that provides options for coaches and teachers to sign up to receive notices and review rounds actually made by their students who have extended access to the data to them. After a student sends a request to a coach/teacher, the system is configured to prompt the coach/teacher to log in for viewing an interface as illustrated by FIG. 28. Once accepted, the system is operable to display reports pertaining to a golfer, however, the system is configured so the coach/teacher cannot modify the reports. The system is further configured to receive user input from the coach/teacher via a click-selection or similar functionality that indicates the desired golfer from a listing such as the "Impersonate as" drop-down menu, and all of that golfer's reports are available, as shown in the FIG. 29.

Figure 30:
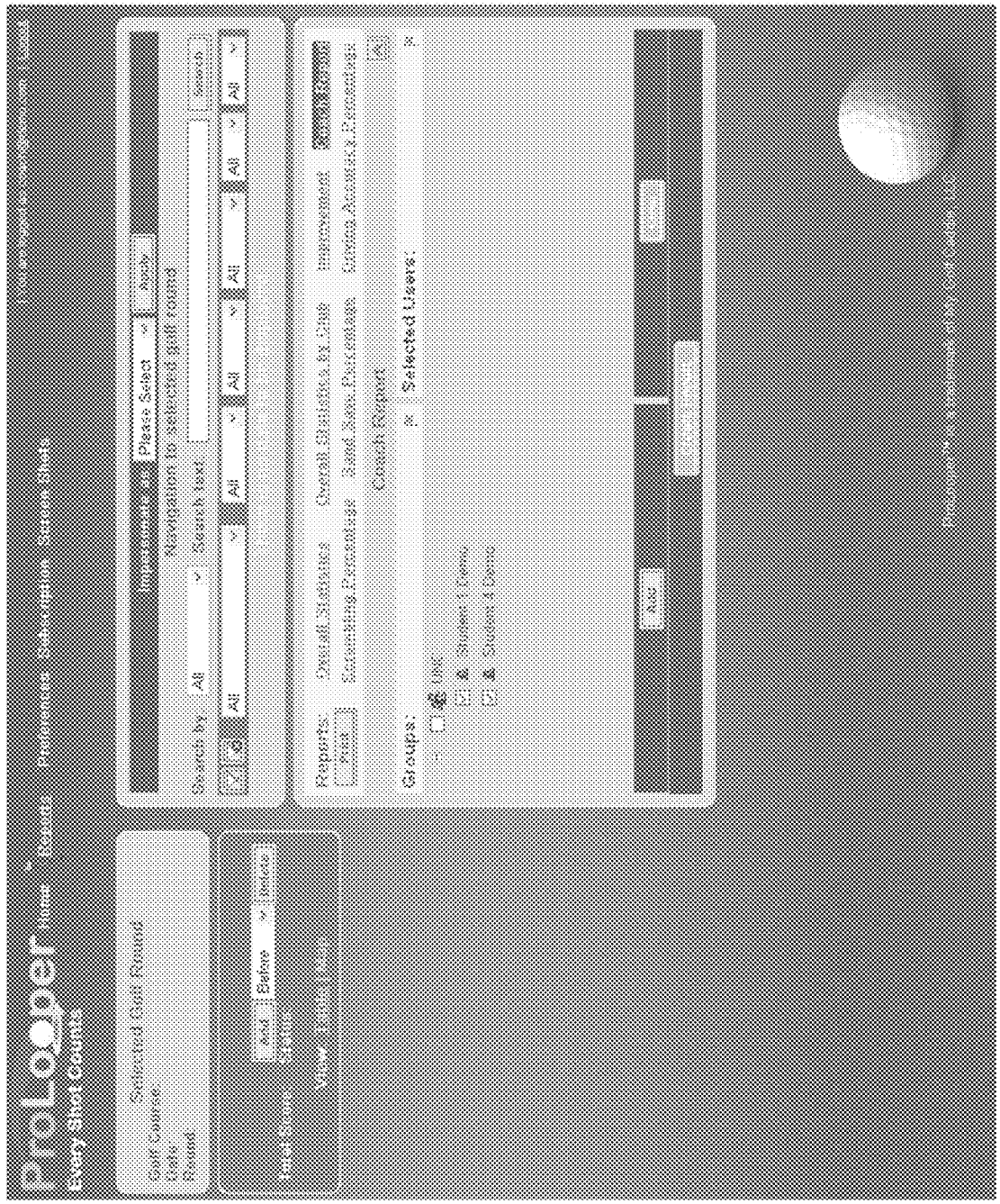
FIG. 30 illustrates a user interface for entering information and viewing analytical outputs according to one embodiment of the present invention.

As illustrated in FIG. 30, the systems and methods of the present invention provide a coach/teacher with the option to create a report that compares multiple golfers or users, preferably side by side. By click-selecting another option, such as "Coach Report", the system is configured to display a list of all golfers that a coach/trainer has access to. The system is configured to display a comparison of golfers. For example, and not limitation, the system is configure to add golfers for comparison when it receives a user click selection for a golfer and a click-selection "Add." Preferably a multiplicity of golfers or users' data is available for review and comparison by the third party coach/teacher.

Figure 31:
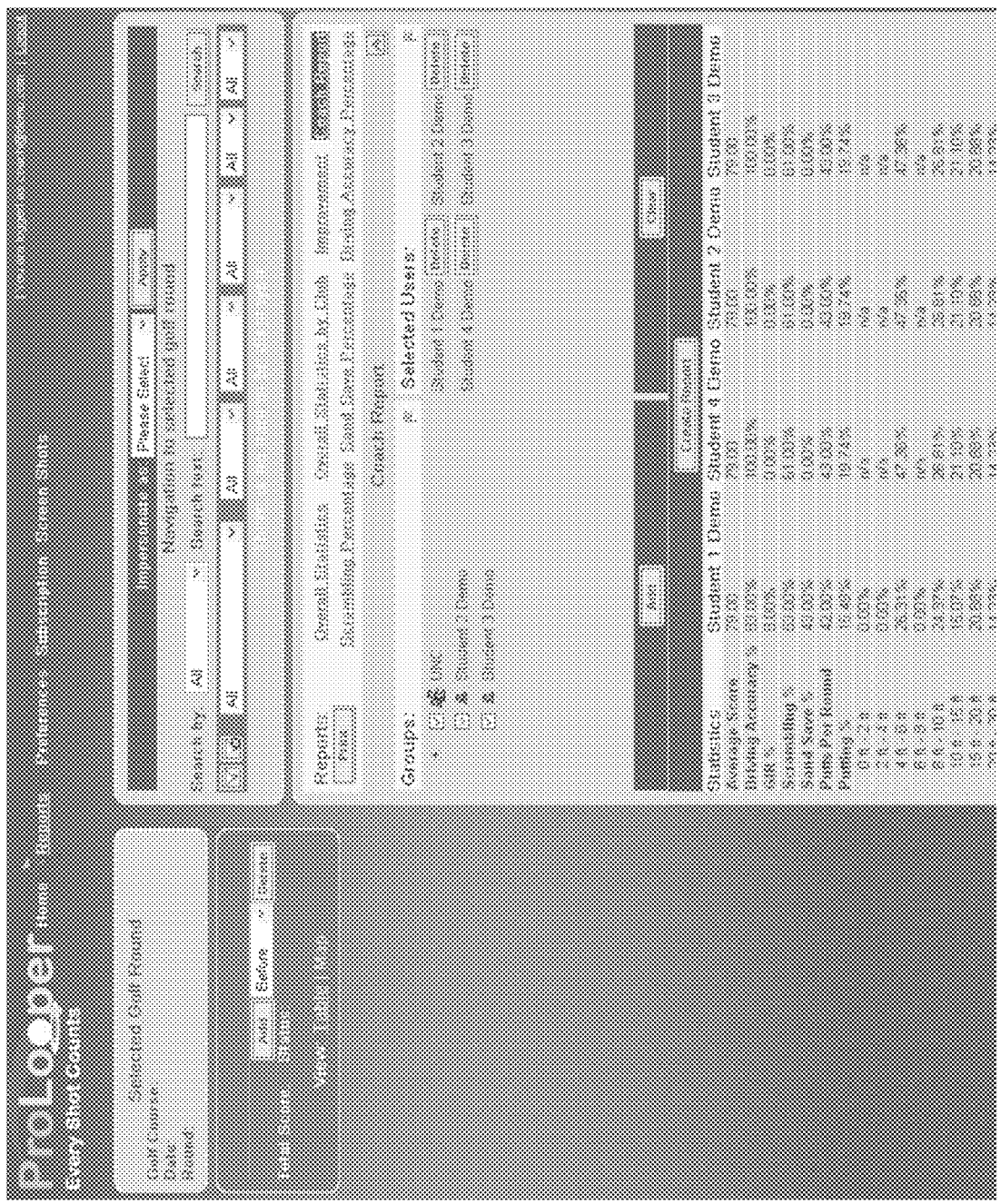
FIG. 31 illustrates a user interface for entering information and viewing analytical outputs according to one embodiment of the present invention.

As illustrated by the screen shot in FIG. 31, the the system is configured to display a report when the system receives user input for a "Create Report" button. The report includes all selected users or golfers data in a comparative manner, preferably with data in tabular format side by side, but optionally in an overlay graphic of shots or other visualization that facilitates comparison or analysis.

The present invention provides visual diagrammatic views including scattergraph diagrams that provide for the directionality of any shot to be uniformly and consistently oriented to provide a zeroed-out orientation for each shot thereby assisting the user/golfer with identification and understanding of errors and trends related to shot misdirection and the corresponding causes related thereto, so that adjustments to form, strategy, and ultimately performance can be made by the user and to which the coach user has access through a web-based account for reviewing the data and providing feedback to the user regarding corrective action or recommendations for improvements.

The system further provides for a unique login for each user, including both application users (students) and coaches/instructors/teachers to access the remote server computer for making data and informational inputs, and for modifying and adding information, including secondary information that includes more detail about play conditions, user status, etc. and coaching-specific information such as corrective actions or recommendations for improvement.

Another aspect of the present invention is to provide methods for statistical analysis of golf performance of a user including the steps of the user inputting information and corresponding coordinates for a series of shots including a start point and a target area, as well as actual shot location throughout a course of play; uploading the shot information and data to a remote server computer, where software is operable to perform statistical analysis and provide outputs via a display or GUI relating to trends in the user's performance over a predetermined period; wherein the scattergraph diagrams include information relating to the directionality of any shot to be uniformly and consistently oriented to provide a zeroed-out orientation for each shot, thereby assisting the user/golfer with identification and understanding of errors and trends related to shot misdirection and the corresponding causes related thereto, so that adjustments to form, strategy, and ultimately performance can be made by the user and for an authorized coach user accessing user information and data, including analytics thereon and providing tracking of coaching recommendations and successful implementation thereof.

The present invention provides a system for providing statistical analysis for golf performance of a user including a portable input device, preferably a handheld device with GPS-functionality, operable for capturing shot data during the golf play of a golfer, the device being further operable to transmit the shot data and related GPS data to a computer for reviewing the shot data and analysis of the shot data through a graphical user interface viewable on a GUI or display; the computer further including software operable for providing statistical analysis of the shot data; wherein the system is configured to receive inputs and coordinates of a series of corresponding starting points and target areas, and recordation of actual shot locations from those starting points during the golf play via the device; and wherein the statistical analysis includes outputs relating to the golfer's golf performance over a predetermined period, and wherein the outputs include scattergraph diagrams having information relating to the directionality of any shot to be uniformly and consistently oriented to provide a zeroed-out orientation for each shot, thereby assisting the user/golfer with identification and understanding of errors and trends related to shot misdirection and the corresponding causes related thereto, so that adjustments to form, strategy, and ultimately performance can be made by the user; the user uploading the shot data to a remote server computer; software operable on the computer performs statistical analysis of the shot data associated with the golfer; and the software providing analytics outputs to the user via a GUI or display having a graphical user interface, including trends in the golfer's performance over a predetermined period.

Figure 32B:
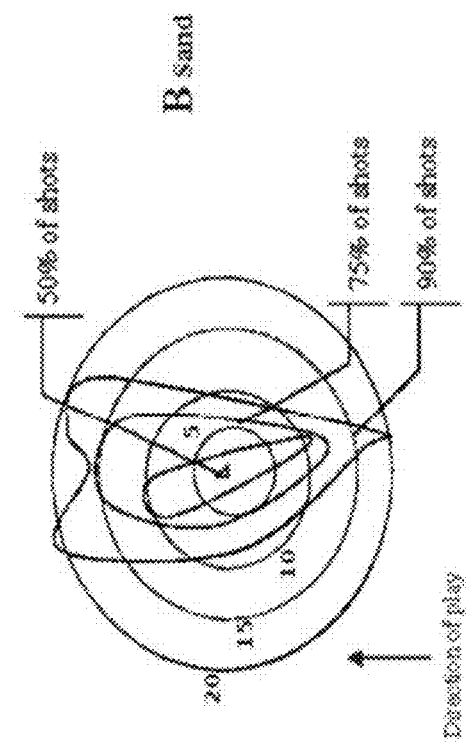
FIG. 32B illustrates a shot zone diagram for a given golf club and a select golf course location and/or condition.
Figure 32D:
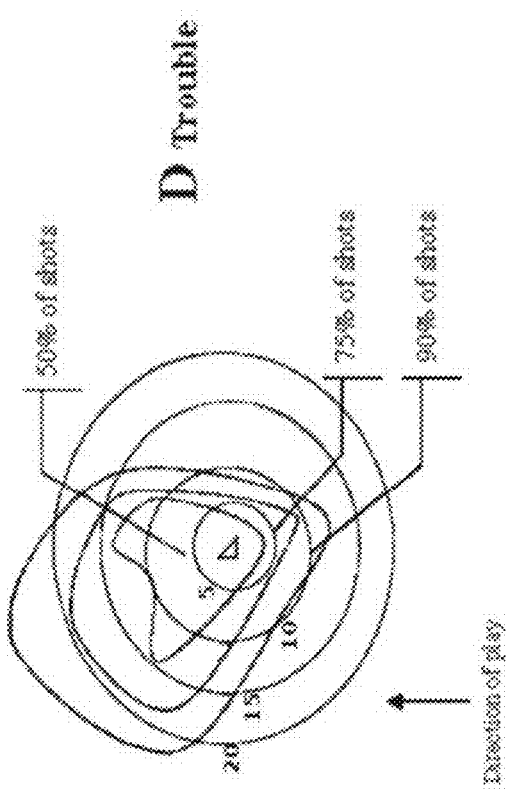
FIG. 32D illustrates a shot zone diagram for a given golf club and a select golf course location and/or condition.
Figure 32A:
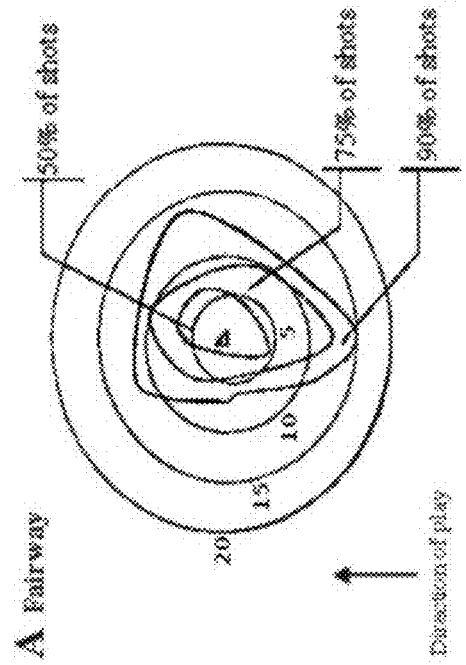
FIG. 32A illustrates a shot zone diagram for a given golf club and a select golf course location and/or condition.
Figure 32C:
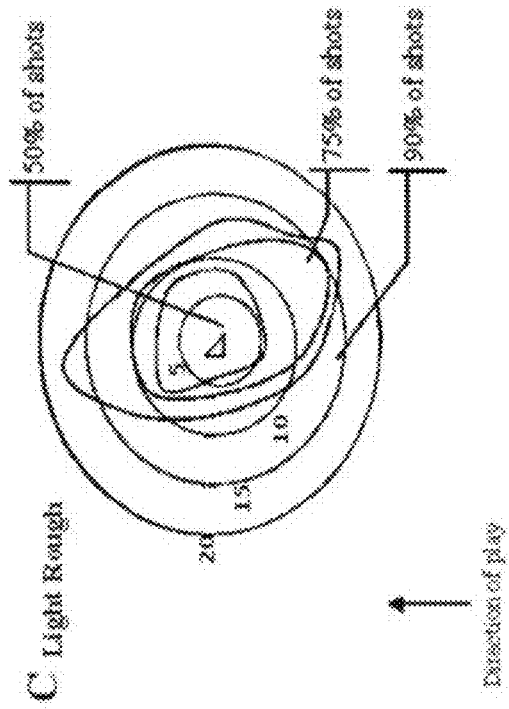
FIG. 32C illustrates a shot zone diagram for a given golf club and a select golf course location and/or condition.

FIGS. 32A-D and 33A-D show shot zone diagrams for a given golf club and select golf course locations and/or conditions. FIG. 32A illustrates a shot zone diagram for a given golf club and a select golf course location and/or condition. FIG. 32B illustrates a shot zone diagram for a given golf club and a select golf course location and/or condition. FIG. 32C illustrates a shot zone diagram for a given golf club and a select golf course location and/or condition. FIG. 32D illustrates a shot zone diagram for a given golf club and a select golf course location and/or condition. FIG. 33A illustrates a shot zone diagram for a given golf club and a select golf course location and/or condition. FIG. 33B illustrates a shot zone diagram for a given golf club and a select golf course location and/or condition. FIG. 33C illustrates a shot zone diagram for a given golf club and a select golf course location and/or condition. FIG. 33D illustrates a shot zone diagram for a given golf club and a select golf course location and/or condition.

FIGS. 32A-D show variations for a pitching wedge. Direction of play is indicated by an arrow at the lower left hand corner of the diagram for each condition. Golf course locations and/or conditions are illustrated here for fairway, sand, light rough, and trouble. Other locations and/or conditions are provided in substitute or addition to any of these. FIGS. 33A-D show variations for a 6 iron. Note also that for each of the illustrated golf clubs, the dates for which the statistical likelihood are illustrated are listed below each golf club. The present invention is operable for short and/or long period of time and the time frame is provided for illustration only. Depending upon the amount of golf played by an individual golfer, the statistical significance and likelihood algorithms are adjusted and/or simply have fewer or greater data points from which to make the projections.

Figure 34:
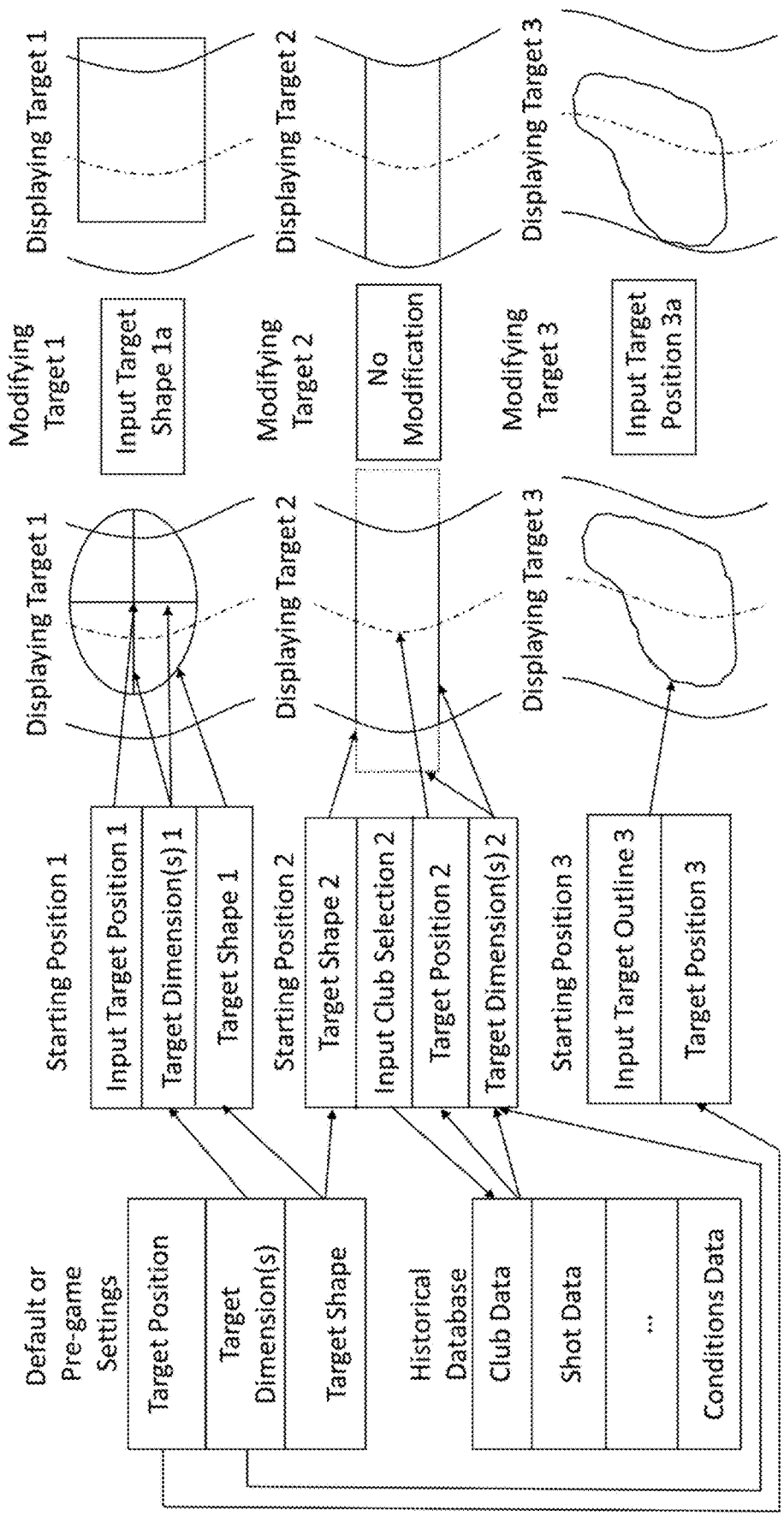
FIG. 34 is a flow diagram illustrating several embodiments of a device receiving a target for statistical analysis according to one embodiment of the present invention.

FIG. 34 is a flow diagram illustrating several embodiments of a device receiving a target for statistical analysis. In one embodiment, from starting position 1, the device receives a target position input and displays a target by using the default target dimensions and target shape previously inputted. In this embodiment, an oval was inputted as the default target shape, with a width dimension slightly larger than the height dimension (e.g., 25 yards by 20 yards), and with the center of the oval equal to the inputted target position. Upon viewing the displayed target, the user decides to modify the shape by selecting a new target shape—a rectangle. Therefore, the device is configured to modify a target based on user input. The device is operable to modify the display such that the center of the shape remains equal to the inputted target position, the dimensions of the shape remain equal to the default target dimensions, and the shape outline is changed from an oval to a rectangle. In alternative embodiments, the system is configured to receive additional modification inputs following the second target display.

FIG. 34 illustrates another embodiment of the invention in starting position 2. The devices receives an inputted club selection, retrieves data from the historical database and pre-game settings and displays the resultant target. In this example, the default target shape is a rectangle including the setting to be confined to a fairway or green. The target position is calculated using the club data, such that the average club shot for the account is used to calculate the target position, centered in the fairway. The target dimensions are calculated using the club data, such that the default target dimension setting is used to determine what percentage the length and width of the rectangle is to be. Although not explicitly illustrated, in another embodiment, the target position is calculated using shot data and default or pregame settings such that the target position is equal the average club shot for a group of accounts less 5% of the average club shot yardage. In the embodiment of starting position 2, the calculated target extends beyond the fairway (shown by the dotted lines) so the device modifies the target to be confined to the fairway (shown by the solid lines).

FIG. 34 additionally illustrates an embodiment for starting position 3. The device receives an inputted target outline and receives a target position from the default settings. Alternatively, the target position could be calculated based on an inputted club selection or combination of an inputted club selection and default position settings. The device then displays the inputted target area centered on the default target position. The center of a custom inputted target area can be calculated in a number of ways know to those skilled in performing such calculations, but one method includes using the center of a largest inner circle to fit within the shape and an alternative method includes calculating an average width and height to use as the center. Referring back to the illustration, the system is operable to receive a new target position by dragging and dropping the target to a new position or using another input mechanism.

For example, in one embodiment, the computer system includes a remote server computer (RSC), wherein the shot data is uploaded from a mobile device to the RSC through the network and the course data is downloaded from the RSC to the device through the network. The RSC stores and analyzes the data for user access and review, the data being accessible via the Internet or worldwide web network. Alternatively, RSC data can be downloaded to and stored on the device for use when the Internet is not available. The system is configured to provide a unique user identification associated with each golfer that is usable by the golfer to access a remote server computer for uploading or downloading user data, and for modifying and adding shot, course and golf play information.

The system is operable to download any rounds that are currently captured on, or inputted into, the device during golf play from remote device to the mobile device, either directly to the device itself or through a docketing or charging station. The software is operable to allow the user to verify the course and date, and then checks to confirm. When the system receives a click-selection of the "Confirm" button, the rounds are then available in the "Review Golf Round" screen, which is viewable on a display on a computer. On this screen view or graphical user interface, the software is operable to receive user input to select or indicate the round a user wishes to review. The status of a round that has not been reviewed yet is preferably marked or noted as having the status of "Uploaded." A partially reviewed round will be indicated as "Changed," and a completely reviewed round is indicated as "Completed" on the user interface. In one embodiment of the present invention, the rounds will not be included in reports unless the round is completed.

In one embodiment, all inputs, analytics, settings and other information is stored locally on the memory of the mobile device. In another embodiment, some or all inputs, analytics, settings and other information is stored on another computing device of the computer system, such as a remote computer, server or database. The mobile device is connected to and the information stored therein accessible through a network during golf play, or, alternatively, is connected to and the information stored therein accessible through a network when connected to the internet before and/or after golf play.

Figure 35:
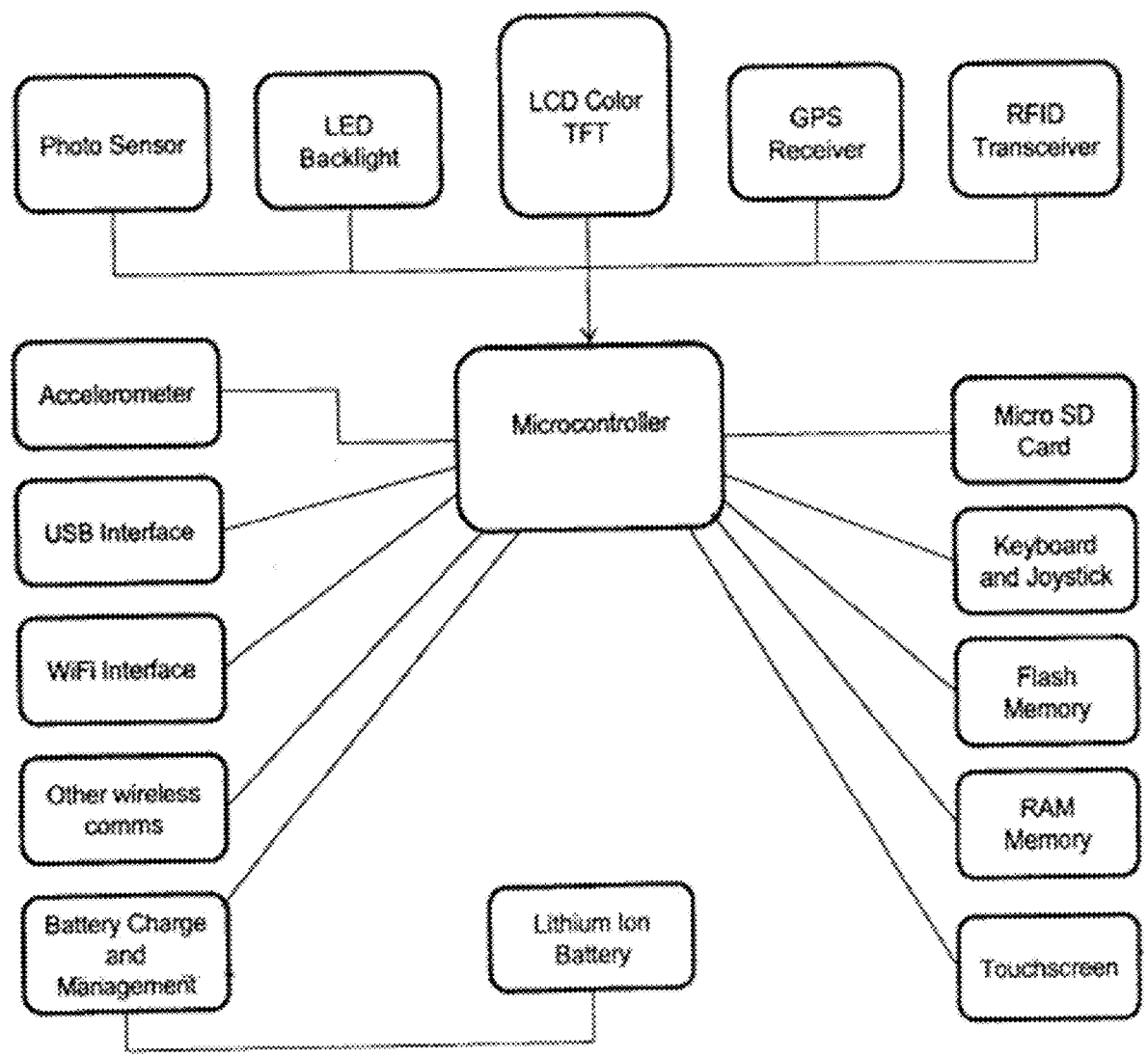
FIG. 35 is a block diagram illustrating a golfing system according to one embodiment of the present invention.

FIG. 35 is a block diagram showing an exemplary configuration of a location-aware portable device that is used by a player to obtain golf course related distance information. In one embodiment, the location-aware device includes a handheld device including multiple components that are managed by microcontroller running software stored in a flash memory or random-access memory, for example. The microcontroller serves as an interface and controller for a plurality of hardware systems and device application systems of the location-aware device. In an exemplary embodiment, the primary purpose of the portable location-aware device is to provide a golfer with distance information to various points on a green, to various targets and hazards on the golf course.

The distance information is provided by referencing mapped data stored in the flash memory. For example, and not limitation, the mapped data includes real time Global Positioning System (GPS) position data acquired by an onboard GPS receiver. The microcontroller is configured to process the GPS data and determine calculations to the mapped points and various areas on the course. The analyzed information is then displayed via the location aware device through a graphical user interface that includes, for example, a sunlight readable color thin-film transistor (TFT) liquid crystal display (LCD) display having a light-emitting diode (LED) backlight. The LED backlight is controlled by a photosensor that measures ambient light and adjusts the brightness of the backlight accordingly. The LCD is transflective so the backlight brightness is reduced when the unit is in sunlight and the brightness is increased when the unit is in low light conditions.

The microcontroller also is configured to receive user input via a keypad and/or joystick. For example, and not limitation, the user input corresponds to a command to move a cursor on the graphical user interface, a command to enter data, a command to select a particular course for display, etc. In yet another embodiment, the location-aware device also includes a touch screen that is configured to receive user input, wherein the user input includes golfer data and/or commands for the location-aware device.

As noted above, the mapped course data is stored in an onboard flash memory, which is configured to be updated via connection of a Universal Serial Bus (USB) port, microSecure Digital (micro-SD) card, WiFi radio or other wireless communications device. An operating system of the microcontroller and various applications executed by the microcontroller also utilize the onboard RAM for storage of temporary data.

An onboard accelerometer determines an orientation of the unit and measures acceleration along a vector. In one exemplary embodiment, the axis orientation and acceleration information is used by the microcontroller to rotate the course data displayed via the graphical user interface to align with the player's orientation on a particular hole, for example.

The location-aware device is powered by a battery that is managed by a charging circuit and power management circuit to provide power to the various components of the location-aware device.

The location-aware device also includes a radio-frequency (RF) transceiver that receives signals transmitted from the tags, described in detail below, which are configured to transmit a club tag ID, tag battery status and other sensor data if the tag is in an operational state. The more specific details regarding the various states of the tags and the data transmitted from the tags are discussed in detail below.

Data transmitted from the tags is received by the RFID transceiver of the location-aware device, and is processed by the microcontroller to record an ID of the club being used, the current position of the location-aware device, club swing data and/or whether there is an indication of a ball strike with the golf club to which the tag is attached. This data is stored in a memory (e.g., flash memory and/or RAM memory) and is used by the microcontroller to automate the scoring process, remind the golfer if a club has been left behind, display the round and shot data graphically on the device, and to be available to upload the data to a computer and/or website for post-round analysis and graphical tracking of the player's golf shots over the course of a round.

Figure 36:
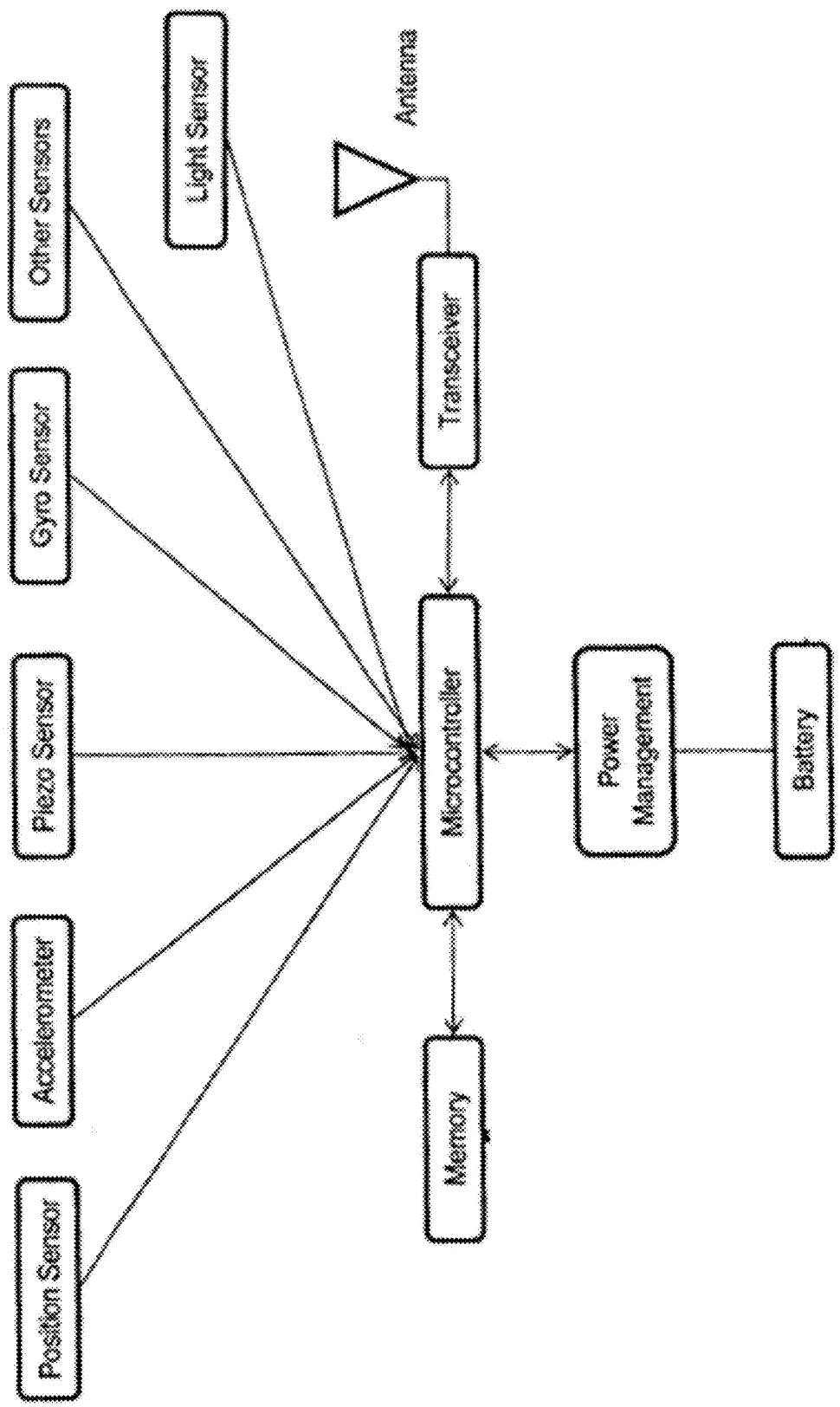
FIG. 36 is a block diagram of a golf tag according to one embodiment of the present invention.

FIG. 36 is a block diagram showing an exemplary configuration of the hardware of an RFID tag that is attached to a golf club, and is used to sense various forces applied to the club. The tag includes a microcontroller that executes applications stored in a memory to process outputs from various sensors of the tag to either detect that a shot has been taken with the club, or relay raw data to the location-aware device which then determines, based on the received data, that a shot has been taken with the club.

The tag includes an RF transceiver that communicates with the RF transceiver of the location-aware device. In one exemplary embodiment, the RF transceiver in the location-aware device and the RF transceiver in the tag are 2.4 GHz transceivers. However, while not described herein, various other short-range wireless transceiver arrangements can be implemented without departing from the scope of the present invention. Another function enabled with a transceiver on the tags is allowing the tags to communicate with each other as an ad-hoc network and relay status and information through other tags to the receiving device.

The tag also includes a plurality of solid state or micro-electro-mechanical (MEM) sensors that are used in the process of detecting whether a ball is struck by the golf club. Examples of these sensors will be described in more detail below.

In one exemplary embodiment, the tag includes an accelerometer that senses vector motion pertaining to the club swing. The tag also includes a position sensor (e.g. tilt sensor), for example, that detects a vertical or horizontal orientation of the club. In another embodiment, a piezo sensor is also provided in the tag, and detects a rapid vibration event, such as the golf club making contact with a golf ball. In yet another embodiment, the tag includes a gyro-sensor that detects a rotational velocity and/or direction of the golf club to which the tag is attached. In one embodiment, the tag includes a light sensor. The light sensor is configured to detect an amount of light on the tag. As discussed in more detail below, light sensor is used to determine whether the club has be removed from, or returned to, a player's golf bag.

Certain electronic components can have functions that are combinable on one chip and sensor package and serve multiple purposes. For example, and not limitation, the accelerometer is configured to provide a degree of tilt data in addition to acceleration data via software. The electronic component is also configured to include a gyro sensor and a "tap" sensor, thereby effectively reducing the number of components needed on the tag circuit board. Optionally, the sensor components can be designed into a custom electronic chip that integrates all of the sensor functions of individual components. Advantageously, this simplifies the circuitry on the tag and improves the power management and battery life on the tag.

The onboard microcontroller is configured to process and analyze analog waveform or digital signal profile outputs from the sensors to determine if the output matches a pattern of data indicating a club swing and a ball strike. As discussed in further detail below, in one embodiment, the system is configured to compare the outputs from each of the sensors against certain signal "signatures" and/or thresholds stored in the memory to determine whether a ball strike event has occurred. These signatures, or pattern data, are updated as the system learns what data indicates a ball strike and what data does not indicate a ball strike. In this manner, the tag is operable to self-learn over a period of time so as to increase the accuracy of detecting when a ball strike even occurs. The thresholds and parameters are updated in the tag's memory via input through the tag transceiver. The data is configured and sent by the location-aware device to optimize the tag sensor processing parameters.

In another embodiment, the system is configured to use additional sensor data to determine club position and/or state and/or verify a ball strike and/or aid in the refinement of signal patterns indicating a ball strike. This additional sensor data includes sensor data provided from additional sensors, such as a solid state accelerometer and/or shock sensors that output an indication of a shock event (ball strike) without the use of piezo sensors, and/or solid state or position sensors that indicate an orientation of the club. This additional sensor data could also be incorporated into the profile data patterns.

The components of the tag are powered by a battery, which is controlled by a power management circuit. The power management circuit manages the power output from the battery to the components of the tag, and is capable of reporting a status of the power remaining in the battery to the microcontroller.

In yet another embodiment, a piezo vibration damper is incorporated into the system to convert mechanical motion and vibration into electrical energy. If the piezo vibration damper is mounted internally to the grip and/or club shaft then the piezo vibration damper has the effect of dampening vibrations from striking the ball. The electrical energy is stored in a capacitor and/or a battery. Typically a piezo device is composed of a material having piezo-electric properties and incorporated on a flexible polymer substrate. In one embodiment, the piezo device is designed to fit into the section of the club comprising the grip and/or comprising the internal section of the club shaft. The piezo device is configured to be electrically connected to a circuit that captures and stores the electrical energy derived from the mechanical and vibration motions of the club shaft.

Preferably, in one embodiment, the tag includes a small format miniaturized circuit that is waterproof and ruggedized mounted to the end of the club grip or internal to the upper portion of the club shaft.

Figure 37:
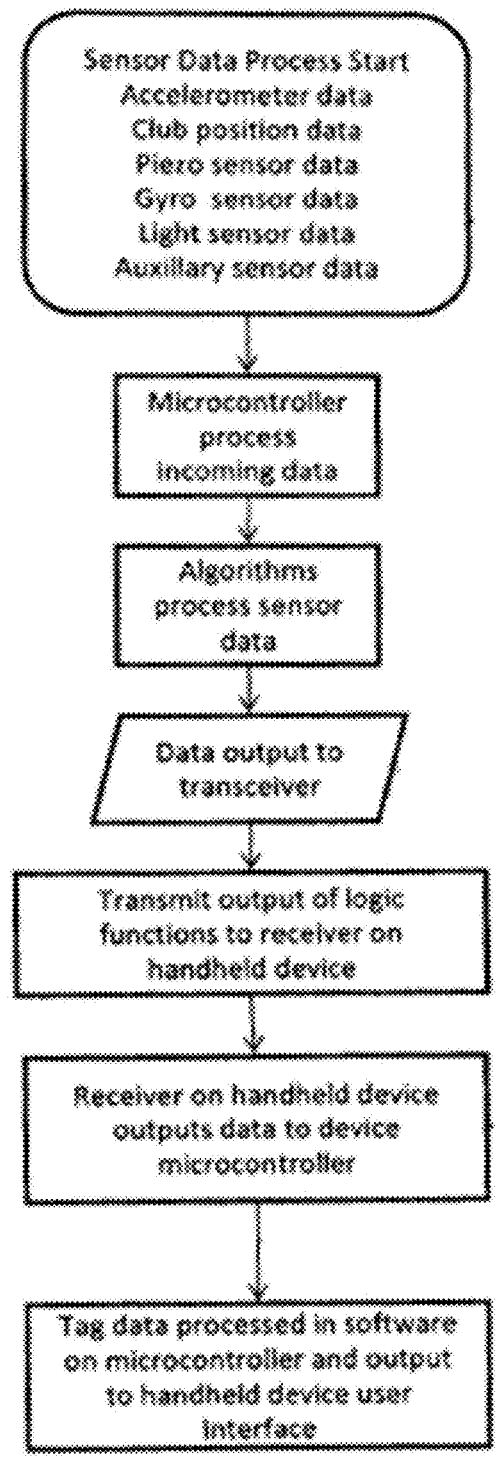
FIG. 37 is a flow chart illustrating detecting and processing a golf swing using a golf tag according to one embodiment of the present invention.

FIG. 37 is a flow chart outlining an overall process of detecting and processing motion dynamics of a club using a tag.

The process starts by collecting club dynamic motion data from one or more of the accelerometer, position sensor, piezo sensor, gyro sensor, light sensor, and any other sensors included in the tag. The process of initializing an operation of the sensors will be described in greater detail below.

The process further includes the microcontroller of the tag receiving and processing the data received by the plurality of sensors. In one exemplary embodiment, the microcontroller uses filters and algorithms to remove extraneous noise and other events that could contribute to false indications of a ball strike event. For example, and not limitation, the microcontroller is configured to compare the sensor data to a set of preliminary threshold values to eliminate erroneous detections. This process is discussed in more detail with reference to FIGS. 38A-C.

In another embodiment, the microcontroller is configured to process the data received from the plurality of sensors, output the processed data to the transceiver, which then transmits a signal to the transceiver of the location-aware device indicating that a ball strike event has been detected. In another exemplary embodiment, the microcontroller is configured to control the transceiver output including motion dynamic data output from the sensors to the location-aware device. The microcontroller at the location-aware device then processes the received data to detect whether a ball strike event has occurred. The motion dynamic data includes raw data outputted by the sensors of the tag. In another embodiment, the motion dynamic data is a processed form of sensor data that is processed by the microcontroller before being output to the location-aware device. Once the transceiver of the location-aware device receives data from the tag, the tag data is outputted to the microcontroller of the location-aware device for further processing. Regardless of the nature of the data output by the tag, the microcontroller is configured to append additional data to the tag.

This additional data that is appended by the microcontroller includes, in one embodiment, unique identification corresponding to the tag. The unique identification data includes a club type (e.g., 5-iron, driver, club manufacturer, shaft length, weight, etc.). The location-aware device is configured to transmit the unique identification data to a memory location on the tag or the unique identification data is inserted to a memory location on the tag at manufacturer. The unique identification data enables the tag to be associated with a specific club at the location-aware device. In one embodiment, each tag is configured to synchronize data to the location-aware device that identifies a relationship between the tag identification data and a club to which each tag is attached. The tag is configured to transmit the data to the location-aware device. In another embodiment, the data transmitted to the location-aware device includes a status of the battery of the tag.

Upon receiving the data from the tag, the microcontroller of the location-aware device is configured to process the received data. For example, and not limitation, the microcontroller is configured to associate a ball strike indication with position data to record an identification of the club used to hit the ball at the current location of the location-aware device. The association of data is outputted to the graphical user interface of the location-aware device to indicate that a stroke has been taken with a specific club at the current location of the location-aware device. Advantageously, this enables a shot to be automatically stored in the location-aware device without any user intervention. This simplifies a process of tracking a score and other statistics related to the round of golf using the location-aware device. As discussed above, other data associated with the transmission from the tag to the location-aware device includes a club ID, motion dynamics and/or additional sensor data. The data is maintained in the location-aware device to track a player's round and is operable to be uploaded to a website or other data repository for analysis.

In one exemplary embodiment, the tag transmits the raw sensor data directly to the location-aware device. The microcontroller of the location-aware device is configured to process the raw sensor data and compare it to data patterns stored in memory (e.g. flash memory or RAM memory). The microcontroller is configured to determine whether a ball strike and/or other club dynamics should be further processed or displayed based on the comparison from the processed raw sensor data and the data patterns stored in memory. The transceiver of the tag is configured to receive signals from the location-aware device in order to "poll" and/or request information such as battery status from the tag on demand. This enables a club inventory system to be implemented by the location-aware device where the receiver tracks the status of the tag and is able to process the dynamic state of the club. This process is discussed in more detail below with reference to FIGS. 48A-48B.

Figure 38A:
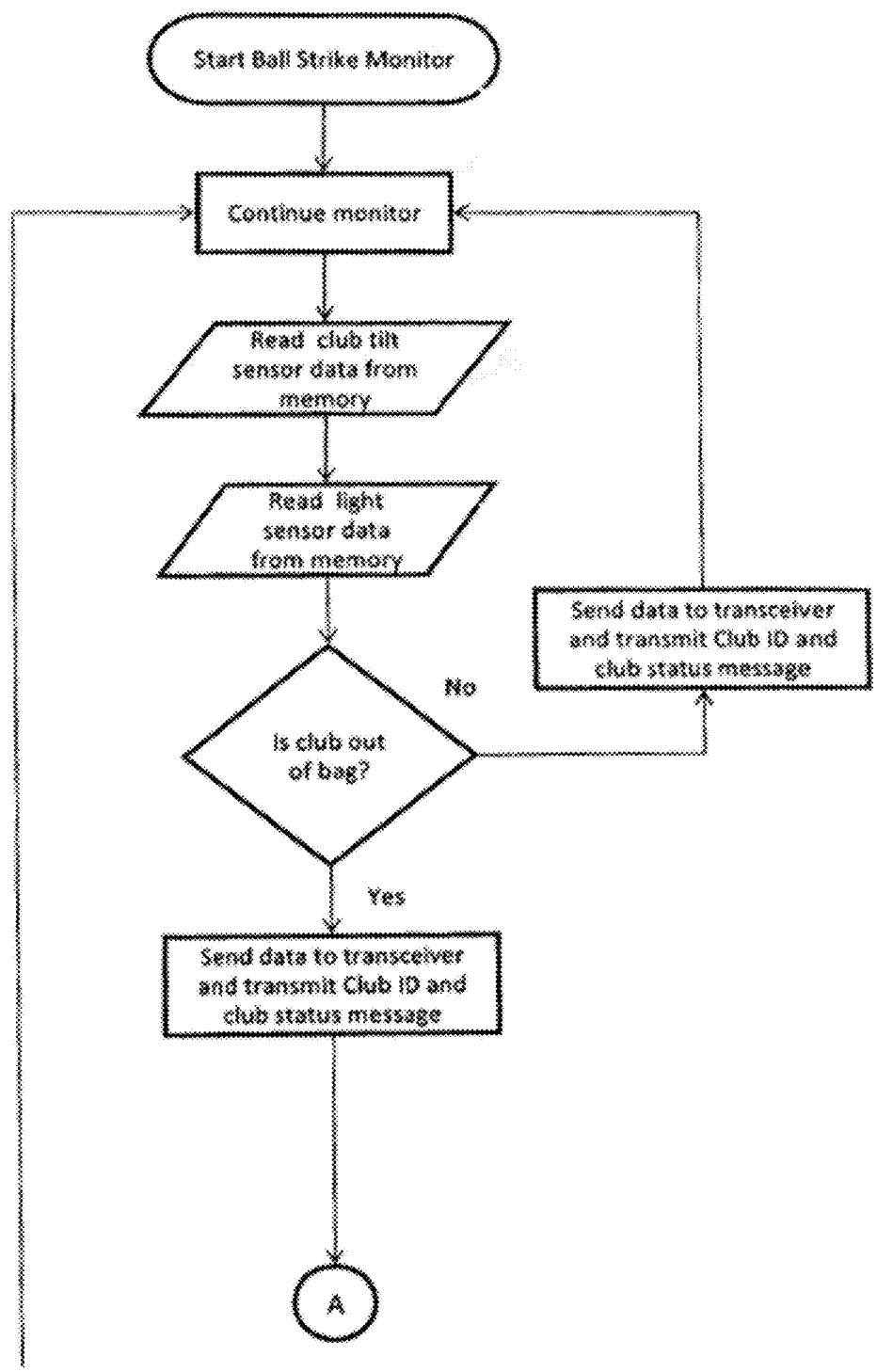
FIG. 38A is a flow chart illustrating the detection of a ball strike using a golf tag according to one embodiment of the present invention.
Figure 38B:
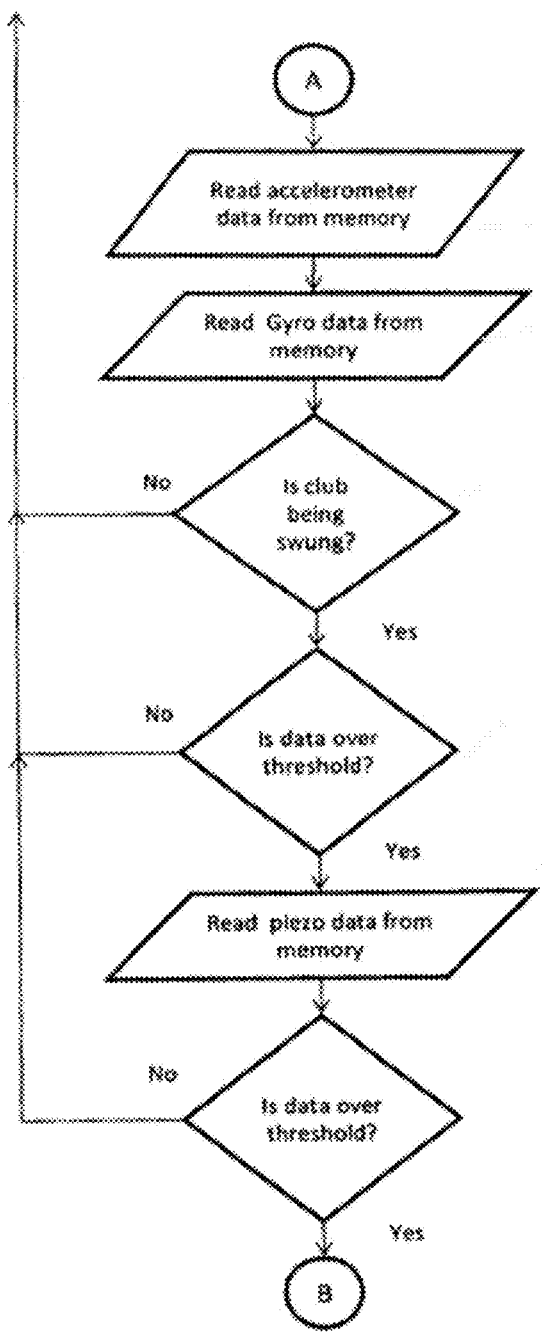
FIG. 38B is a flow chart illustrating the detection of a ball strike using a golf tag according to one embodiment of the present invention as shown in FIG. 38A.
Figure 38C:
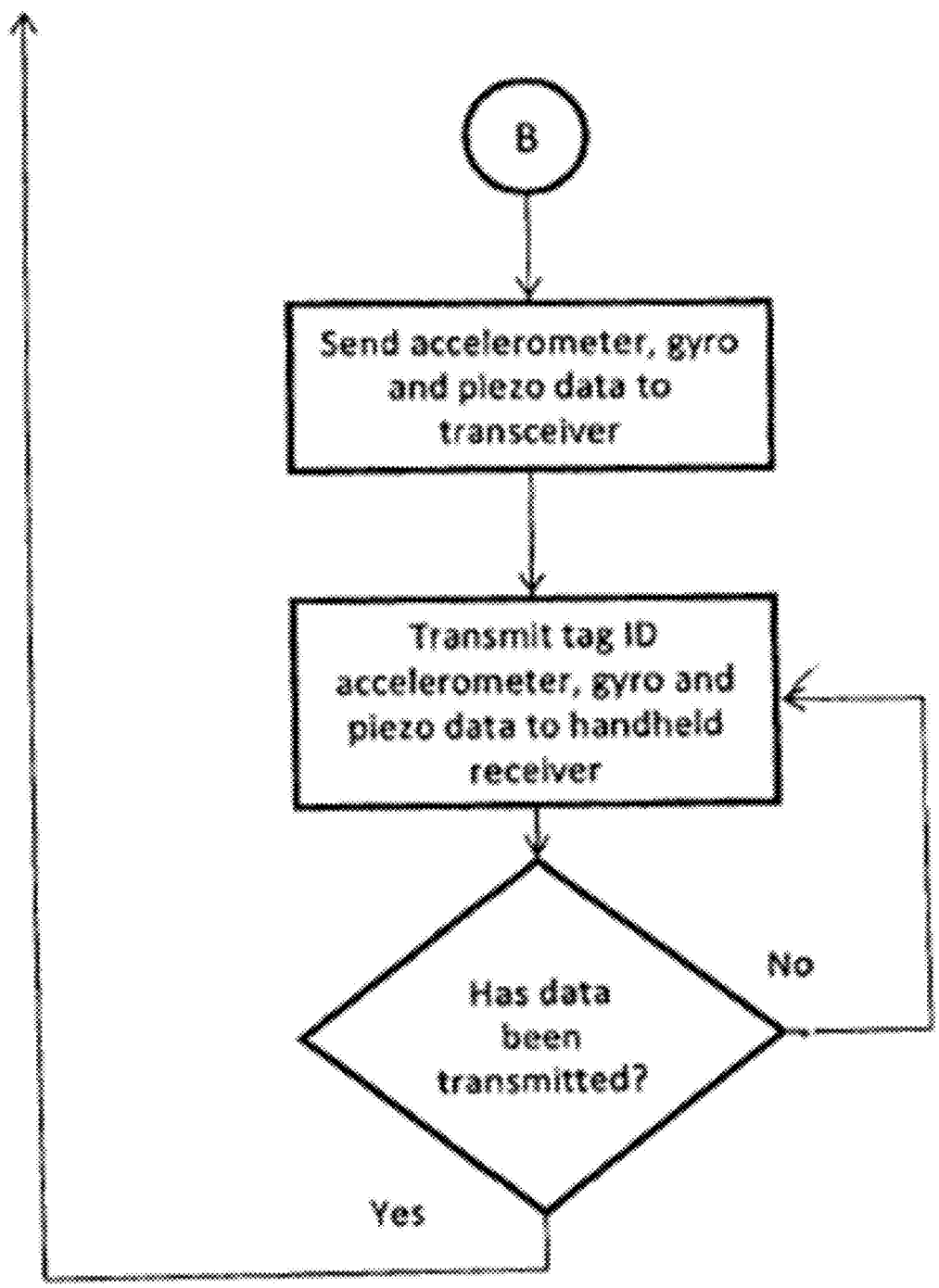
FIG. 38C is a flow chart illustrates the detection of a ball strike using a golf tag according to one embodiment of the present invention as shown in FIG. 38A.

FIGS. 38A-38C is a flow chart showing a more detailed flow of detecting a ball strike event using the various sensors located in the tag. The process includes the microcontroller of the tag monitoring a status of one or more sensors of the tag to determine if the club has been removed from the player's bag. It is important to know when a tag is "at rest" and when it is in an "active" state so that data is not unnecessarily (e.g. continuously) transmitted from the tag when the club is inactive. Such a determination also allows the microcontroller to conserve power of the tag battery by controlling the power management circuit to reduce or eliminate power supplied from the battery to the various components of the tag when the club is not being used. The "at rest" and "active" determination is made by the microcontroller of the tag reading sensor data received from the microcontroller, which is stored in memory.

These sensor outputs reflect the removal of a golf club from a golf bag, thus indicating that the club is about to be used for a shot. One example of sensor data used to trigger the microcontroller to begin a process of detecting a ball strike is club tilt data. The microcontroller reads the club tilt data stored in the memory and determines that the club has gone from an inverted state to an upright state. Various sensor outputs, either individually or in combination, are processed by the microcontroller in order to make a determination that the club is "active". Examples of these sensor outputs include outputs of the position sensor, the accelerometer and/or the gyro sensor.

Figure 39:
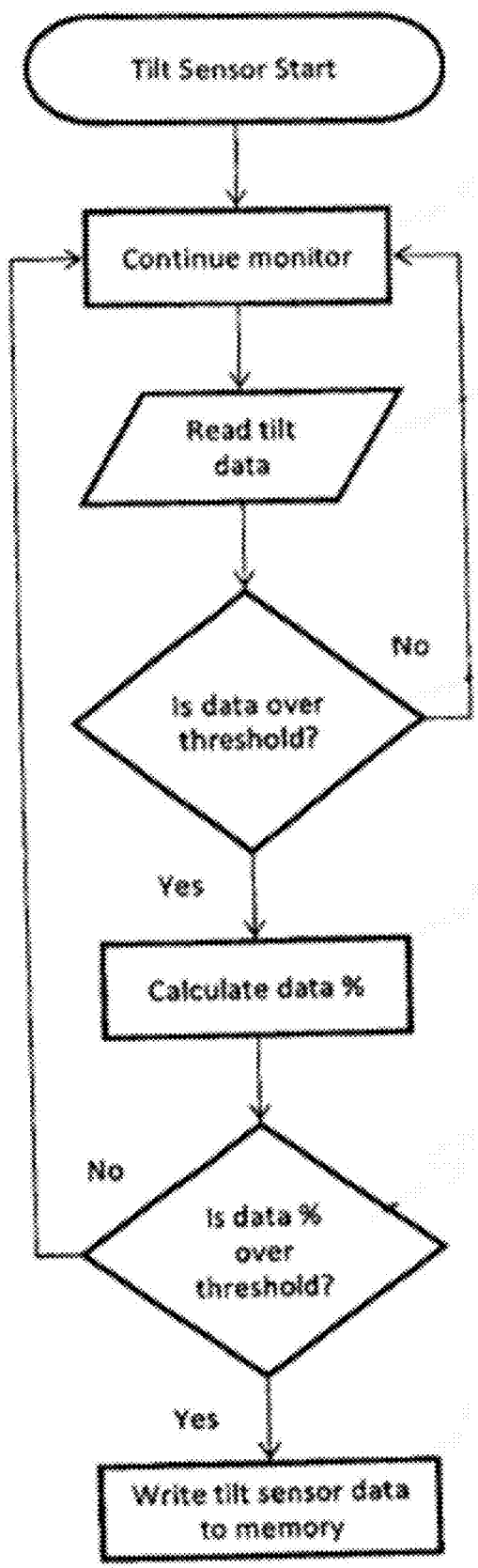
FIG. 39 illustrates a process of acquiring and analyzing tilt sensor data according to one embodiment of the present invention.

An exemplary process flow of acquiring and analyzing the tilt sensor data is described in the flow chart shown in FIG. 39. As noted above, any one or a plurality of data from the position sensor, the accelerometer and/or the gyro sensor are monitored by the microcontroller to determine if the club is in an active state. The microprocessor reads the tilt data (e.g., the output of the one or more sensors used to detect tilt) and determines whether the output exceeds an initial threshold value, which is stored in the memory. When the output does not exceed a threshold value (e.g. the club is not sufficiently tilted), the microprocessor continues to monitor the tilt data. When it is determined that the tilt data exceeds the threshold value, the microprocessor then calculates a percentage value of the tilt data with respect to a maximum value of the tilt data and determines whether this percentage is greater than a threshold value.

When the percentage does not exceed a threshold percentage (e.g. the club is not sufficiently tilted), the microprocessor continues to monitor the tilt data. When it is determined that the calculated percentage exceeds the threshold percentage, the microprocessor writes the percentage to the memory.

Referring again to FIG. 38A, the microprocessor determines whether the club is "active" or out of the bag by monitoring the tilt data stored in the memory. As described above, when the microprocessor determines that the calculated percentage exceeds the threshold percentage, the microprocessor writes the percentage to the memory. Similarly, the process is used to determine that the club has been returned to the bag after it has been in an active state. In the case that the club has been active and has been returned to the bag, the tag sends an indication to the location-aware device that the club has been returned to the bag. In the case that this process serves as a determination that the club has been removed from the bag, it acts as a trigger for the tag to wake up, or to start actively processing outputs from other sensors of the tag. The detection of a change to an active state also results in the microcontroller of tag to control the transceiver of the tag to send an indication to the location-aware device that the club is in an active state or has been removed from the bag. This transmitted information indicates both that the club is now in an active state, and includes a unique ID corresponding to the tag. As discussed above, this unique ID specifically identifies the club, or some other type of ID that is specific to the tag and has previously been correlated with an identification of the club to which it is attached at the location-aware device. The location-aware device is configured to display an indication to a user that a specific club has been selected for a shot.

Another option for detecting an "at rest" or "active" state of the club is to detect data from a light sensor included in the tag. The microcontroller reads the light data stored in the memory and determines that the club has gone from a dark state (e.g. in a golf bag) to a light state (e.g., out of golf bag) when the level of light detected by a light sensor included in the tag exceeds a predetermined threshold.

Figure 40:
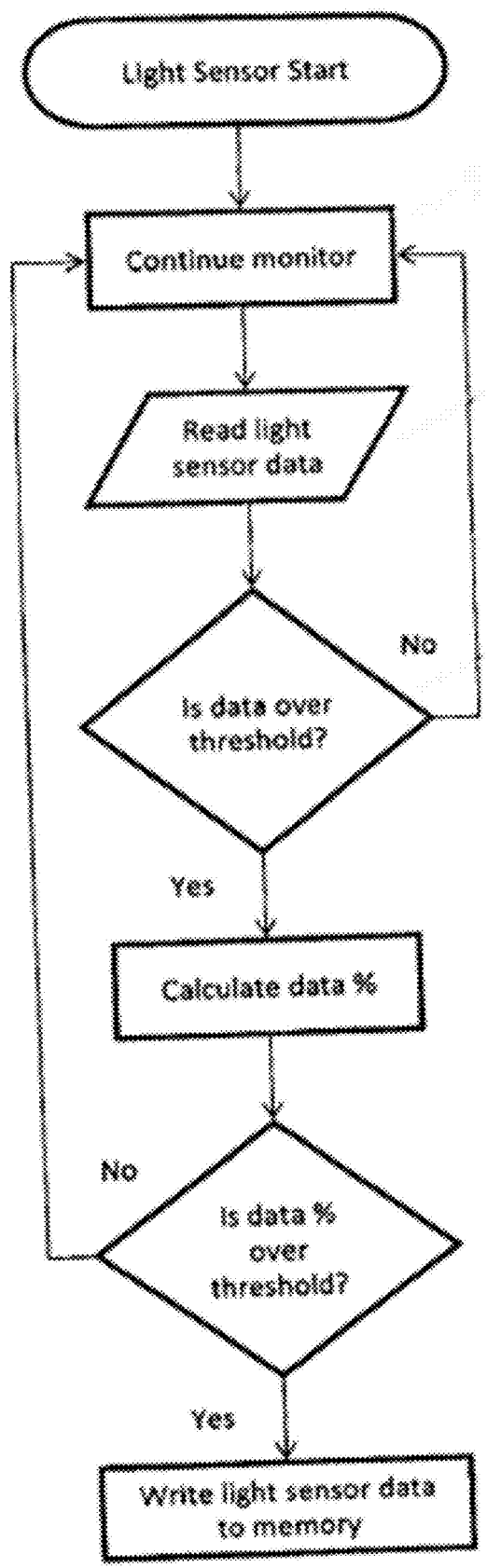
FIG. 40 illustrates a process of acquiring and analyzing light sensor data according to one embodiment of the present invention.

An exemplary process flow of acquiring and analyzing the light sensor data is described in the flow chart shown in FIG. 40. The microprocessor reads the light data (e.g., the output of a light sensor included in, or attached to, the tag) and determines whether the output of the light sensor exceeds an initial threshold value, which is stored in the memory. When the output does not exceed a threshold value (e.g. the club is still in a dark state), the microprocessor continues to monitor the light data. When it is determined that the light data exceeds the threshold value, the microprocessor calculates a percentage value of the light data with respect to a maximum value of the light data and determines whether this percentage is greater than a threshold percentage.

Referring again to FIG. 38A, the microprocessor determines whether the club is "active" or out of the bag by monitoring the light data stored in the memory. As described above, when the microprocessor determines that the calculated percentage exceeds the threshold percentage, the microprocessor writes the percentage to the memory.

This process serves as a determination that the club has been removed from the bag, and acts as a trigger for the tag to wake up, or to start actively processing outputs from other sensors of the tag. The detection of a change to an active state also results in the microcontroller of the tag to control the transceiver of the tag to send an indication to the location-aware device that the club is in an active state or has been removed from the bag. This transmitted information indicates both that the club is now in an active state, and includes a unique ID corresponding to the tag. As discussed above, this unique ID includes specifically identify the club, or some other type of ID that is specific to the tag and has previously been correlated with an identification of the club to which it is attached at the location-aware device. The location-aware device then displays an indication to a user that a specific club has been selected for a shot.

The processes described above of determining if a club is in an "at rest" and "active" state are operable to be used together or individually. For example, the tag is configured to transition from the "at rest" state to the "active" state by monitoring only the detected light value or the detected tilt of the club. On the other hand, in another embodiment, the microprocessor of the tag is configured to monitor both attributes and determine to transition the tag into active mode only after both of the sensed tilt data and light data exceed the threshold value.

Further, as discussed above in each individual example, the detection of a change to an active state also result in the microcontroller of tag to control the transceiver of the tag to send an indication to the location-aware device that the club is in an active state or has been removed from the bag. This transmitted information indicates both that the club is now in an active state, and includes a unique ID corresponding to the tag. As discussed above, this unique ID specifically identifies the club, or it some other type of ID that is specific to the tag and has previously been correlated with an identification of the club to which it is attached at the location-aware device. The location-aware device is operable to display an indication and/or alert that a specific club has been selected for a shot.

In one embodiment, once the tag is determined to have transitioned into the active state, the microcontroller of the tag reads accelerometer data from memory to determine if a ball strike event has occurred.

Figure 41:
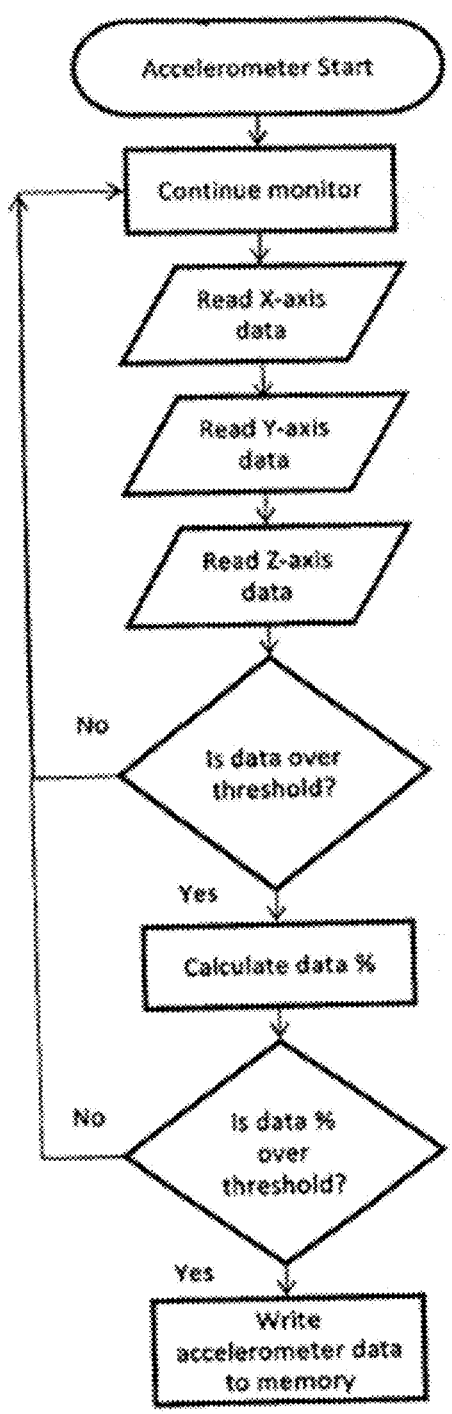
FIG. 41 illustrates a process of acquiring and analyzing accelerometer data according to one embodiment of the present invention.

An exemplary process flow of acquiring and storing the accelerometer data is described in the flow chart shown in FIG. 41. The microprocessor reads X-axis, Y-axis, and Z-axis data output from the accelerometer. The microprocessor then analyzes the data output from the accelerometer, and determines if the data exceeds a threshold that indicates a club swing or club swing and ball strike. When the output does not exceed a threshold value (e.g. the data is insufficient to indicate that a swing has been taken), the microprocessor continues to monitor the accelerometer data. When it is determined that the accelerometer data exceeds the threshold value, the microprocessor calculates a percentage value of the accelerometer data with respect to a maximum value of the accelerometer data and determines whether this percentage is greater than a threshold percentage. When the percentage does not exceed a threshold percentage, the microprocessor continues to monitor the accelerometer data. When it is determined that the calculated percentage exceeds the threshold percentage, the microprocessor transmits the percentage to the memory.

Referring back to FIG. 38B, in one embodiment, once the accelerometer data is read by the microprocessor, then the gyro sensor data is read. The process of acquiring and storing the data output from the gyro sensor will be described with reference to FIG. 42.

Figure 42:
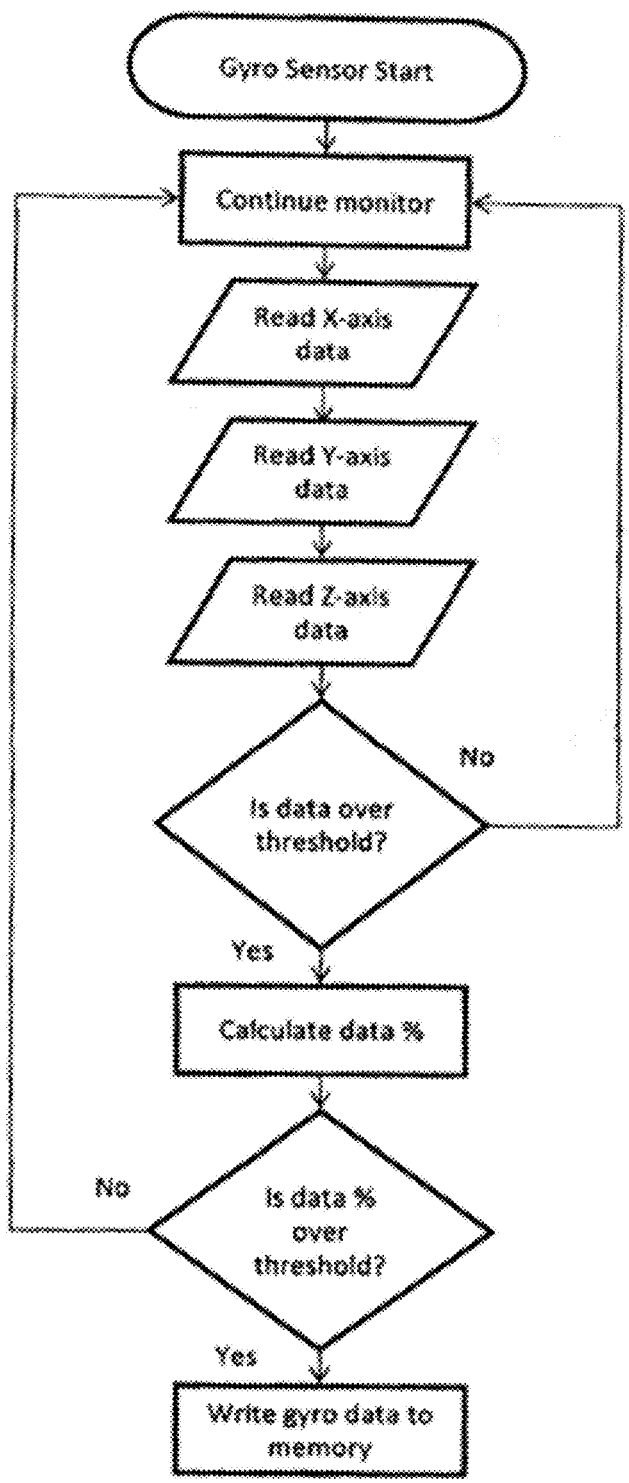
FIG. 42 illustrates a process of acquiring and analyzing gyro sensor data according to one embodiment of the present invention.

As shown in FIG. 42, the microprocessor reads X-axis, Y-axis and Z-axis data output from the gyro sensor. The microprocessor then analyzes the data output from the gyro sensor, and determines if the data exceeds a threshold that indicates a club swing or club swing and ball strike. When the output does not exceed a threshold value (e.g. the data is insufficient to indicate that a swing has been taken), the microprocessor continues to monitor the gyro sensor data. When it is determined that the data output from the gyro sensor exceeds the threshold value, the microprocessor calculates a percentage value of the gyro sensor data with respect to a maximum value of the gyro sensor data and determines whether this percentage is greater than a threshold percentage. When the percentage does not exceed a threshold percentage, the microprocessor continues to monitor the gyro sensor data. When it is determined that the calculated percentage exceeds the threshold percentage, the microprocessor writes the percentage to the memory.

As noted above, the processes described in FIGS. 41 and 42 indicate how the microcontroller calculates a percentage of an output of each of the accelerometer and gyro sensors relative to a golf swing and stores this data in memory. Referring back to FIG. 38B, once this data is stored, the microprocessor reads the data from the memory and to determine whether the golf club is being swung. Similarly to how the tilt and light data are used to determine if the club has been removed from the bag, the accelerometer and gyro sensor data are then used to determine if the club is being swung by the player. If the microprocessor determines that the club is not being swung because percentage data corresponding to one or both of the accelerometer and the gyro is not stored, then the process returns to the beginning and the microprocessor continues to determine whether the club is in an active or rest state. If percentage data corresponding to both the accelerometer output and the gyro sensor are stored in memory, the microcontroller determines whether the stored data exceeds a threshold value. If the stored data does not exceed the threshold, the process returns to the beginning and the microprocessor continues to determine whether the club is in an active or rest state. If both of the stored accelerometer percentage and gyro percentage exceed a predetermined threshold value, the microcontroller then reads a stored percentage corresponding to an output of the piezo sensor.

In the overall flow of detecting the shot, the piezo data is used to detect the impact of a ball on the face of the club to which the tag is attached. Thus, building on the sensor outputs define above, the flow first determines whether the club is in an active or rest state by monitoring data indicating a tilt of the club and/or light data. The process then looks to the accelerometer and gyro sensor data to determine if the club is actually being swung. If the club is active and has been swung, the microprocessor then looks to the output of the piezo sensor to determine if the active and swinging club has made contact with a ball. If so, it is likely that the club has been used to strike a ball.

Figure 43:
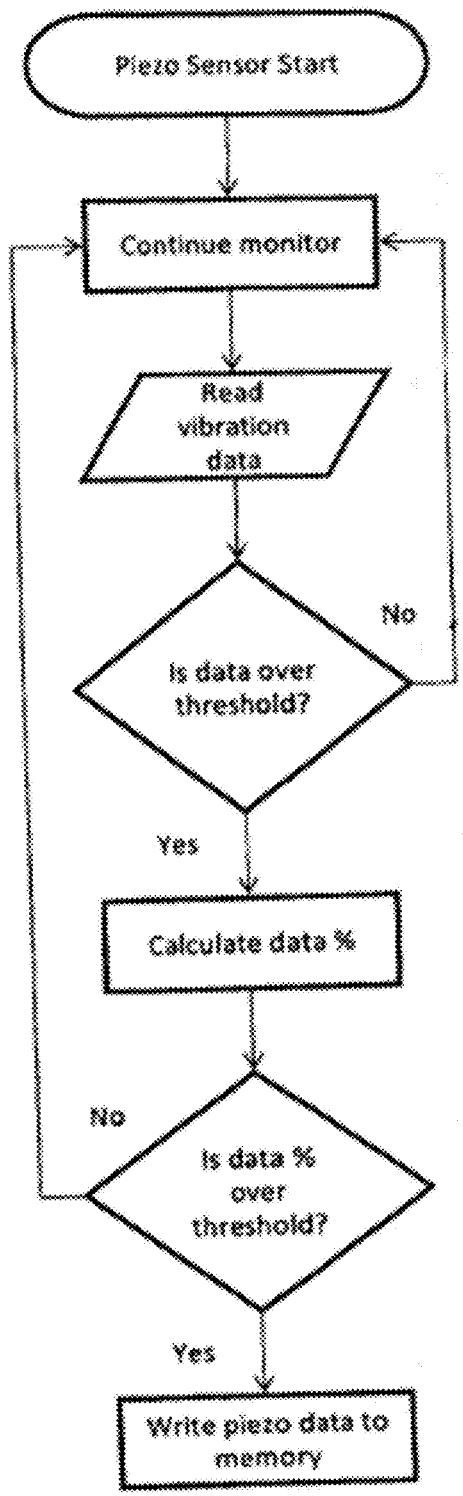
FIG. 43 illustrates a process of acquiring and analyzing piezo sensor data according to one embodiment of the present invention.

An exemplary process flow of acquiring and storing the piezo sensor data is described in the flow chart shown in FIG. 43. The microprocessor reads vibration or shock data output from the piezo sensor. The microprocessor then analyzes the data output from the piezo sensor, and determines if the data exceeds a threshold that indicates a ball strike. When the output does not exceed a threshold value (e.g. the data is insufficient to indicate that the club has impacted a ball), the microprocessor continues to monitor the piezo sensor data. When it is determined that the accelerometer data exceeds the threshold value, the microprocessor calculates a percentage value of the piezo data with respect to a maximum percentage and determines whether this percentage is greater than a threshold percentage. When the percentage does not exceed a threshold percentage, the microprocessor continues to monitor the piezo sensor data. When it is determined that the calculated percentage exceeds the threshold percentage, the microprocessor writes the percentage to the memory. Referring back to FIG. 38B, the microprocessor then determines whether the stored percentage corresponding to the piezo sensor data is greater than a threshold value.

When this value does not exceed the threshold value, the process continues monitoring the tilt and/or light data to determine whether the club has again transitioned into an active state. When it is determined that the stored piezo sensor data percentage exceeds the threshold, the microcontroller then sends the stored percentages related to the piezo sensor data, the gyro sensor data and the accelerometer to the transceiver, which then transmits this data to the location-aware device. In one embodiment, the transmitted data also includes other data such as the identification information corresponding to the tag or club, as discussed above. Once it is determined that the data has been transmitted from the tag to the location-aware device, the process returns to and the microcontroller again starts waiting for a determination that the club has entered an active state.

Figure 44:
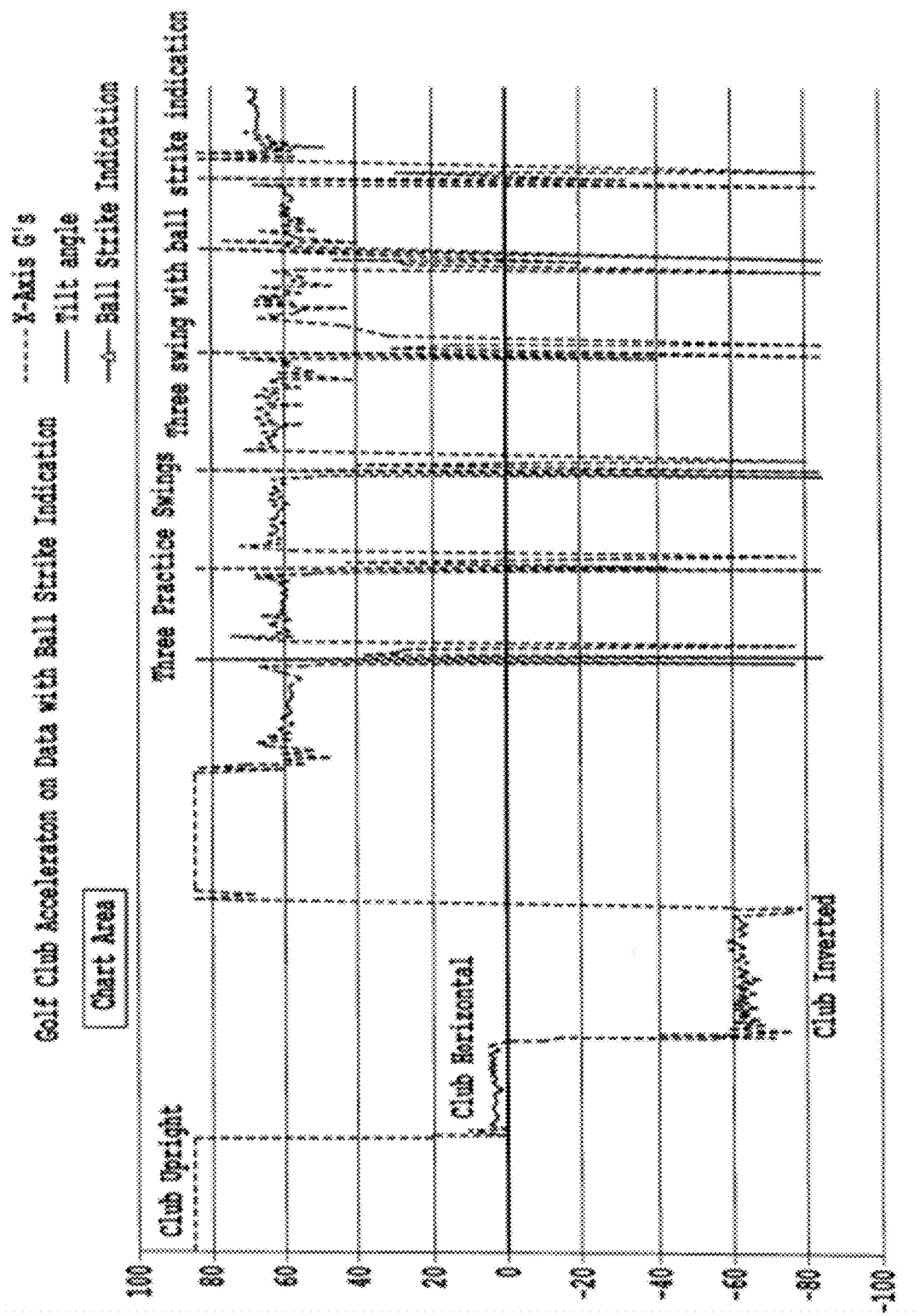
FIG. 44 is a graphical representation of sensor data output according to one embodiment of the present invention.
Figure 45:
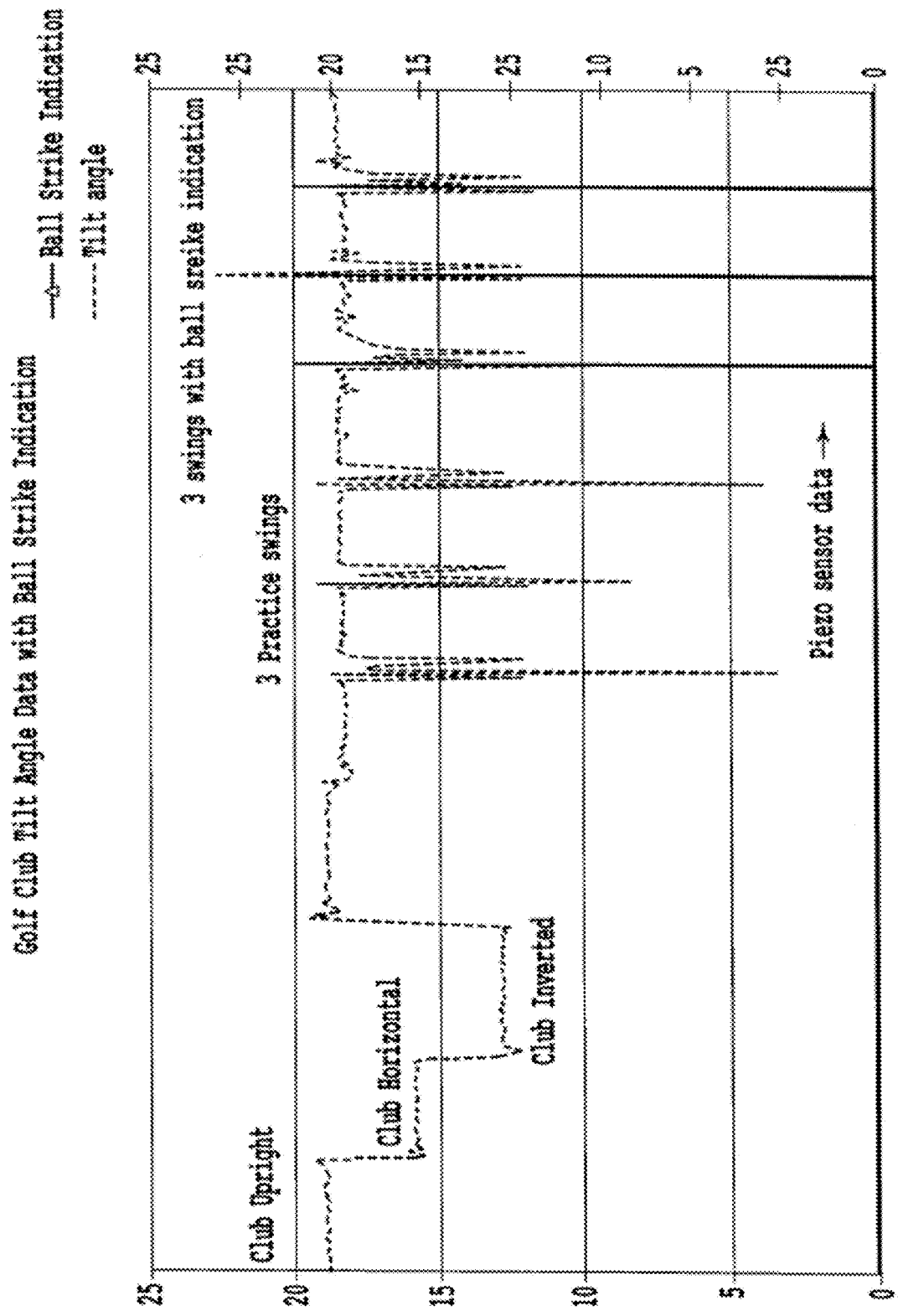
FIG. 45 is a graphical representation of sensor data according to one embodiment of the present invention.
Figure 46:
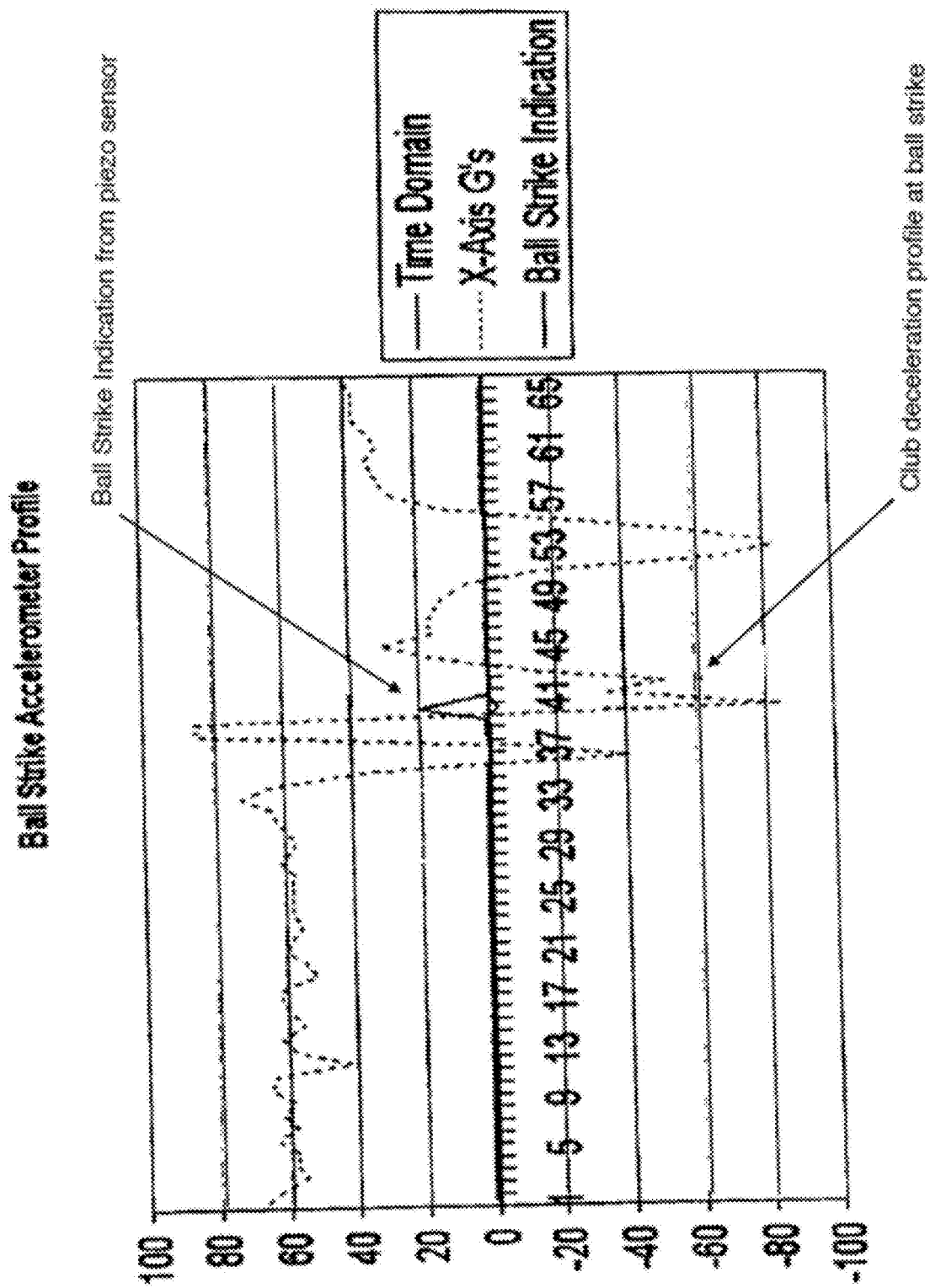
FIG. 46 is a graphical representation of sensor data according to one embodiment of the present invention.

FIGS. 44-46 describe exemplary sensor outputs, and the relationship between these outputs and the detection of a shot.

FIG. 44 shows club position as determined by accelerometer X-Axis orientation based on static acceleration (i.e. relationship to gravity when not in motion). Upright club position is determined by approximately 1 G, horizontal by O G's, and inverted by approximately—1 G These scaling factors are adjustable and can be refined with further calibration. Also shown are three practice swings indicated by X-axis dynamic acceleration followed by three swings showing x-axis dynamic acceleration accompanied by a voltage indication from the piezo sensor. The piezo sensor determines a ball strike independently from the accelerometer and outputs a O voltage if sensor activity is below the piezo sensor's sensing threshold and it outputs a slight voltage in proportion to the vibration it senses. A microcontroller reads the voltage output from the piezo sensor which can be either analog or digital depending on sensor and circuitry and outputs a logic O or logic 1 depending on the voltage thresholds. The accelerometer data and piezo sensor data are transmitted to the location-aware device when they exceed a predetermined threshold as determined by the microcontroller of the tag. As discussed below, the location-aware device determines if a ball strike indication was sent in the same time frame that club acceleration took place and thus validates a ball strike indication. As discussed above, if the microcontroller of the tag determines that there is data output from the accelerometer that exceeds the preliminary threshold data stored at the tag, but the piezo data does not exceed this threshold, then depending on configuration parameters, either no sensor data is transmitted to the location-aware device or the data is transmitted with the intent to provide adaptive feedback to the system to refine processing of data for further events. Once the sensor data has satisfied the initial threshold values at the tag, then the data is transmitted to the location-aware device to allow for a more refined detection as to whether a ball strike even should be registered, as discussed above.

FIG. 45 shows the relationship of club tilt angle to a ball strike. The club position data, as indicated by the position data or the gyro data, provides a clear indication of a ball strike at a particular time. As shown in the figure, there is a high likelihood of a ball strike when the club is quickly inverted, horizontal, then upright with a piezo output during the upright portion of this sequence.

Additionally, FIG. 45 also shows how the tag can process tilt information to determine when a club has been removed from the bag. During play, a club stored in the player's bag is typically stored in an inverted (e.g., stored in upright golf bag) or horizontal state (e.g., stored in a bag lying flat). However, when the club is help upright, or when the club transitions between, upright, horizontal and inverted during a shortened time period, there is a high likelihood that this club is now active and is about to be used for a shot.

FIG. 46 shows the relationship of club acceleration to a ball strike indication. It is possible to capture the deceleration due to the club striking the ball. The club acceleration and deceleration profiles are processed numerically to form data patterns. The data patterns are used to indicate and/or verify and/or augment other data inputs for a ball strike. An additional benefit of this is to profile a golfer's swing pattern with his own clubs to upload for further analysis.

Figure 47:
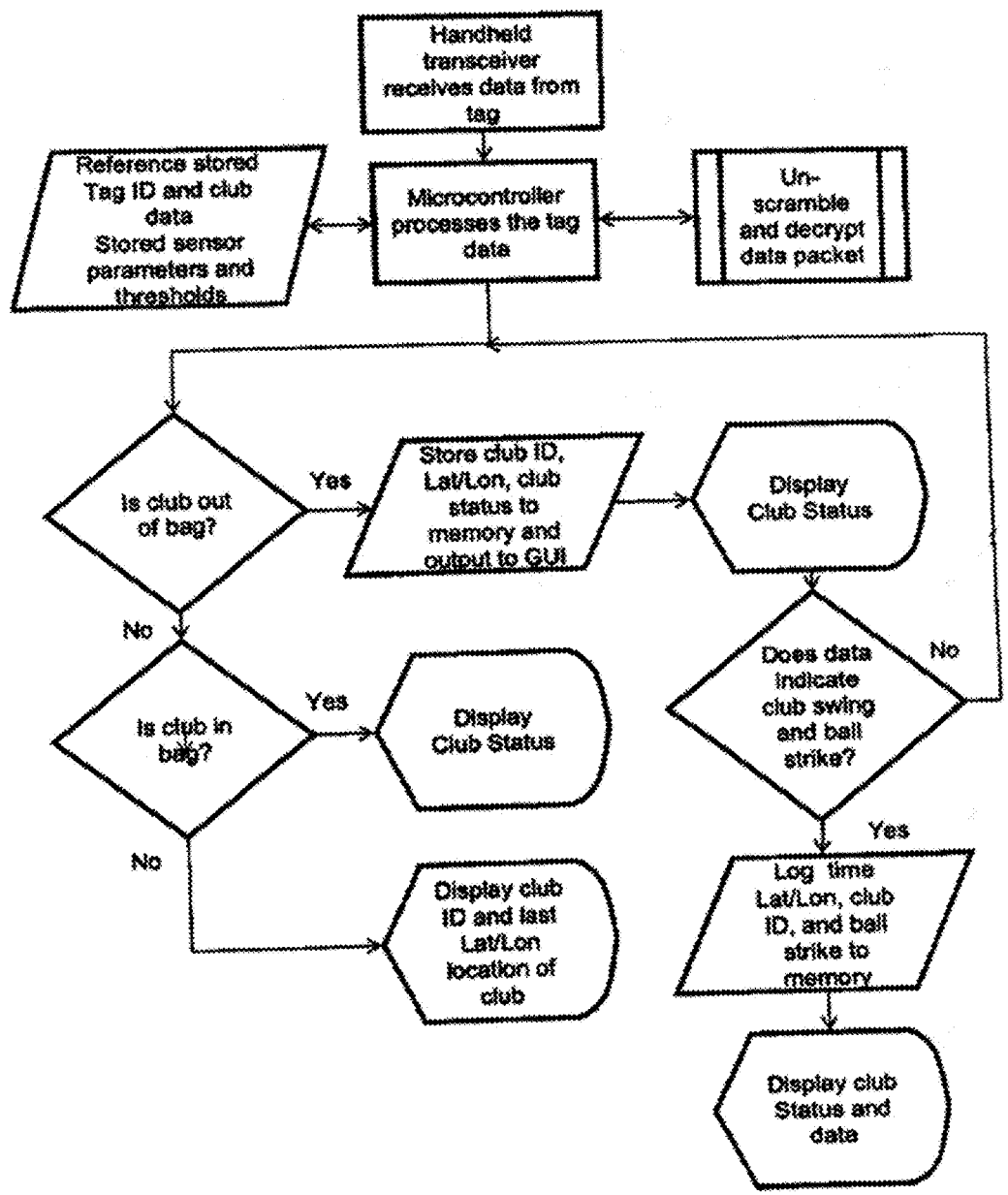
FIG. 47 illustrates a process of data processing and communication between a remote device and a golf tag according to one embodiment of the present invention.

FIG. 47 shows an exemplary process flow of the location-aware device upon receiving data from the tag. The transceiver of the location-aware device receives the identification information and sensor data from the tag. Upon receiving a transmission from the tag, the microcontroller of the location-aware device processes the received tag data. This process includes demodulating, unscrambling and/or decrypting the packet data received from the tag.

The location-aware device then references stored tag ID and club ID information based on ID information received from the tag. As described above, the ID information received from the tag includes specific club identification data (e.g. 5-iron, driver, etc.) or ID information unique to the tag that has been pre-registered in the location-aware device as corresponding to a particular club. This allows the club to which the tag is attached to be identified by the location-aware device for subsequent processing.

The location-aware device also references stored sensor parameters and thresholds to determine what subsequent steps should be performed based on the received data.

As discussed above, one transmission from the tag indicates that the club is not in an active state and that the club has been removed from the player's golf bag. The location-aware device determines that the club has been removed from the player's bag based on the data transmitted from the tag. As discussed above, once the tilt and/or light sensor data indicates that the club is active, the tag transmits an "Out of Bag" message to the location aware-device. Upon receiving this message, the location-aware device is configured to store the identification of the club in association with a current location of the location-aware device, and output a message to the player via the GUI of the location-aware device that a specific club or clubs have been removed from the player's bag. The location-aware device then analyzes the data received from the tag to determine if the sensor data received from the tag indicates that there has been a ball strike.

Some examples of processing the received sensor data are described in greater detail below. The microcontroller of the location-aware device analyzes the received sensor data to determine whether a ball strike event has occurred. Below are specific examples of how the data is processed by the location-aware device to determine whether a ball strike event has occurred. Once the location-aware device determines that a ball strike even has occurred, the location-aware device stores a current location of the ball strike and an identity of the club used for the ball strike event. This information is displayed to a user of the location-aware device as an indication that a stroke has been taken. The GUI is further configured to display information identifying the location of the stroke and update a user's current score for a round of golf based on the detected stroke.

The location-aware device is further operable to receive an indication from the tag that the club has been returned to the bag. This signal is transmitted from the tag based on a determination that the light sensor has transitioned from a light state to a dark state, or that the club is stored in an inverted position for a predetermined time period after having entered an active state. Obviously a combination of these sensor outputs could be used by the tag to determine that the club has been returned to the bag.

Upon determining that the signal received from the tag indicates that the club has been returned to the bag, the location-aware device displays that the club has been returned to the bag.

The location-aware device, however, is also able to determine if a club has been lost on the course by determining that the club has not been returned to the bag after receiving an indication that the club is in an active state from the transmitter. For example, the location-aware device determines that the device has moved a predetermined distance without receiving an indication that the club has been returned to the bag after being in an active state. Alternatively, the location-aware device determines that a club indicated as being in an active state has not been returned to the bag after a predetermined period of time from receiving the indication that the club was active. Upon either determination, the location-aware device initiates a lost club indication and display a message to the player indicating the position of the course corresponding to the last time the club was activated. The player can then identify where the club was left behind, and retrieve the club.

There are several ways the probability of a ball strike can be described. Ideally this is configured to match the golfer or golf clubs used once a profile is established. The probability will be a real number in the range of 0 to 1. As the probability of a ball strike event approaches 100% the greater the possibility the system is detecting a ball strike.

Several examples follow of ways to implement probability to determine a ball strike event based on the fusion of the sensor data. One or multiples of sensors can be included in the implementation. Typically, the more data provided in the system the more accurate the probability will be.

The data below indicates exemplary threshold indications of a ball strike based on the different algorithms if the ball strike % threshold is 75%. The ball strike % threshold is configurable and adaptive as the system "learned" the dynamics and sensor indications of a ball strike. The system is configured to receive verification via user input that a golf swing produced a ball strike or did not produce a ball strike. This data is recorded into memory to help refine and optimize the sensor algorithms over time.

Terms: P=Probability BSE=Ball Strike Event C=Club Position Sensor Data A=Accelerometer Sensor Data P=Piezo Sensor Data G=Gyro Sensor Data Wf=Weighting factor (0 ton)

The first example described below, describes an embodiment in which the microcontroller of the location-aware device processes club position sensor data, accelerometer sensor data, piezo sensor data and gyro sensor data to determine if a ball strike event has occurred. The probability of a ball strike event P(BSE) in this instance can be determined as (P)BSE=(C (% Degrees Up, Down, Horizontal)/Threshold)*(A/A Data Samples)+(P/P Data Samples)+(G/G Data/Samples)/3. Tables 1-4 show exemplary P(BSE) calculations based on this relationship.

TABLE 1

| | P(BSE) = 100% | | | |
|---|---|---|---|---|
| Sensors | Club Position | Accelerometer | Piezo | Gyro |
| Sensor Data | 100 Deg +/− % | 60 | 60 | 60 |
| Sample Rate | 100 Threshold | 60 | 60 | 60 |
| Sensor Data % | 100% | 100% | 100% | 100% |

TABLE 2

| | P(BSE) = 87% | | | |
|---|---|---|---|---|
| Sensors | Club Position | Accelerometer | Piezo | Gyro |
| Sensor Data | 75 Deg +/- % | 40 | 40 | 40 |
| Sample Rate | 100 Threshold | 60 | 60 | 60 |
| Sensor Data % | 75% | 67% | 67% | 67% |

TABLE 3

| | P(BSE) = 61% | | | |
|---|---|---|---|---|
| Sensors | Club Position | Accelerometer | Piezo | Gyro |
| Sensor Data | 85 Deg +/- % | 40 | 50 | 40 |
| Sample Rate | 100 Threshold | 60 | 60 | 60 |
| Sensor Data % | 75% | 67% | 83% | 67% |

TABLE 4

| | P(BSE) = 40% | | | |
|---|---|---|---|---|
| Sensors | Club Position | Accelerometer | Piezo | Gyro |
| Sensor Data | 75 Deg +/- % | 40 | 40 | 40 |
| Sample Rate | 100 Threshold | 60 | 60 | 60 |
| Sensor Data % | 75% | 67% | 67% | 67% |

The second example described below, the probability of a ball strike event P(BSE) in can be determined as (P)BSE=(C (% Degrees Up, Down, Horizontal)/Threshold)+[(A/A Data Samples)+(P/P Data Samples)+(G/G Data Samples))/4. Tables 5-8 show exemplary P(BSE) calculations based on this relationship.

TABLE 5

| | P(BSE) = 100% | | | |
|---|---|---|---|---|
| Sensors | Club Position | Accelerometer | Piezo | Gyro |
| Sensor Data | 100 Deg +/- % | 60 | 60 | 60 |
| Sample Rate | 100 Threshold | 60 | 60 | 60 |
| Sensor Data % | 100% | 100% | 100% | 100% |

TABLE 6

| | P(BSE) = 93% | | | |
|---|---|---|---|---|
| Sensors | Club Position | Accelerometer | Piezo | Gyro |
| Sensor Data | 95 Deg +/- % | 55 | 55 | 55 |
| Sample Rate | 100 Threshold | 60 | 60 | 60 |
| Sensor Data % | 95% | 92% | 92% | 92% |

TABLE 7

| | P(BSE) = 75% | | | |
|---|---|---|---|---|
| Sensors | Club Position | Accelerometer | Piezo | Gyro |
| Sensor Data | 85 Deg +/- % | 40 | 50 | 40 |
| Sample Rate | 100 Threshold | 60 | 60 | 60 |
| Sensor Data % | 85% | 67% | 83% | 67% |

TABLE 8

| | P(BSE) = 69% | | | |
|---|---|---|---|---|
| Sensors | Club Position | Accelerometer | Piezo | Gyro |
| Sensor Data | 85 Deg +/- % | 40 | 40 | 40 |
| Sample Rate | 100 Threshold | 60 | 60 | 60 |
| Sensor Data % | 75% | 67% | 67% | 67% |

The third example described below, the probability of a ball strike event P(BSE) in can be determined as (P)BSE=(C (% Deg Up, Down, Horizontal)/Threshold)*(A/A Data Samples)*(P/P Data Samples)*(G/G Data Samples). Tables 9-12 show exemplary P(BSE) calculations based on this relationship.

TABLE 9

| | P(BSE) = 100% | | | |
|---|---|---|---|---|
| Sensors | Club Position | Accelerometer | Piezo | Gyro |
| Sensor Data | 100 Deg +/- % | 60 | 60 | 60 |
| Sample Rate | 100 Threshold | 60 | 60 | 60 |
| Sensor Data % | 100% | 100% | 100% | 100% |

TABLE 10

| | P(BSE) = 73% | | | |
|---|---|---|---|---|
| Sensors | Club Position | Accelerometer | Piezo | Gyro |
| Sensor Data | 95 Deg +/- % | 55 | 55 | 55 |
| Sample Rate | 100 Threshold | 60 | 60 | 60 |
| Sensor Data % | 95% | 92% | 92% | 92% |

TABLE 11

| | P(BSE) = 31% Sensors | | | |
|---|---|---|---|---|
| Sensors | Club Position | Accelerometer | Piezo | Gyro |
| Sensor Data | 85 Deg +/- % | 40 | 50 | 40 |
| Sample Rate | 100 Threshold | 60 | 60 | 60 |
| Sensor Data % | 85% | 67% | 83% | 67% |

TABLE 12

| | P(BSE) = 22% | | | |
|---|---|---|---|---|
| Sensors | Club Position | Accelerometer | Piezo | Gyro |
| Sensor Data | 75 Deg +/- % | 40 | 40 | 40 |
| Sample Rate | 100 Threshold | 60 | 60 | 60 |
| Sensor Data % | 75% | 67% | 67% | 67% |

In the fourth example described below, the probability can be further refined by including weighting factors into the algorithm. The weighting factors can be individually described for each set of sensor data. The probability of a ball strike event P(BSE) in can be determined as (P)BSE=(C (% Deg Up, Down, Horizontal)/Threshold*C Wf)*[(A/A Data Samples*A Wf)+(P/P Data Samples*P Wf)+(G/G Data Samples*G Wf)]/3. Tables 13-16 show exemplary P(BSE) calculations based on this relationship.

TABLE 13

P(BSE) = 100%

| Sensors | Club Position | Accelerometer | Piezo | Gyro |
|---|---|---|---|---|
| Sensor Data | 100 Deg +/− % | 60 | 60 | 60 |
| Sample Rate | 100 Threshold | 60 | 60 | 60 |
| Sensor Data % | 100% | 100% | 100% | 100% |
| Weighting Factor | 1.00 | 1.00 | 1.00 | 1.00 |

TABLE 14

P(BSE) = 94%

| Sensors | Club Position | Accelerometer | Piezo | Gyro |
|---|---|---|---|---|
| Sensor Data | 95 Deg +/− % | 55 | 55 | 55 |
| Sample Rate | 100 Threshold | 60 | 60 | 60 |
| Sensor Data % | 95% | 92% | 92% | 92% |
| Weighting Factor | 1.00 | 1.00 | 1.25 | 1.25 |

TABLE 15

P(BSE) = 66%

| Sensors | Club Position | Accelerometer | Piezo | Gyro |
|---|---|---|---|---|
| Sensor Data | 85 Deg +/− % | 40 | 50 | 40 |
| Sample Rate | 100 Threshold | 60 | 60 | 60 |
| Sensor Data % | 85% | 67% | 83% | 67% |
| Weighting Factor | 1.00 | 1.00 | 1.25 | 1.25 |

TABLE 16

P(BSE) = 54%

| Sensors | Club Position | Accelerometer | Piezo | Gyro |
|---|---|---|---|---|
| Sensor Data | 75 Deg +/− % | 40 | 40 | 40 |
| Sample Rate | 100 Threshold | 60 | 60 | 60 |
| Sensor Data % | 75% | 67% | 67% | 67% |
| Weighting Factor | 1.00 | 1.00 | 1.25 | 1.25 |

In the fifth example described below, the probability can be further refined by including weighting factors into the average. The probability of a ball strike event P(BSE) in can be determined as (P)BSE=(C (% Deg Up, Down, Horizontal)/Threshold*C Wf)*[(A/A Data Samples*A Wf)+(P/P Data Samples*P Wf)+(G/G Data 5 Samples*G Wf)]/Avg*Wf. Tables 17-20 show exemplary P(BSE) calculations based on this relationship.

TABLE 17

P(BSE) = 100% - Weighting Factor = 1

| Sensors | Club Position | Accelerometer | Piezo | Gyro |
|---|---|---|---|---|
| Sensor Data | 100 Deg +/− % | 60 | 60 | 60 |
| Sample Rate | 100 Threshold | 60 | 60 | 60 |
| Sensor Data % | 100% | 100% | 100% | 100% |

TABLE 18

P(BSE) = 99% - Weighting Factor = 1.05

| Sensors | Club Position | Accelerometer | Piezo | Gyro |
|---|---|---|---|---|
| Sensor Data | 95 Deg +/− % | 55 | 55 | 55 |
| Sample Rate | 100 Threshold | 60 | 60 | 60 |
| Sensor Data % | 95% | 92% | 92% | 92% |

TABLE 19

P(BSE) = 69% - Weighting Factor = 1.05

| Sensors | Club Position | Accelerometer | Piezo | Gyro |
|---|---|---|---|---|
| Sensor Data | 85 Deg +/− % | 40 | 50 | 40 |
| Sample Rate | 100 Threshold | 60 | 60 | 60 |
| Sensor Data % | 85% | 67% | 83% | 67% |

TABLE 20

P(BSE) = 57% - Weighting Factor = 1.05

| Sensors | Club Position | Accelerometer | Piezo | Gyro |
|---|---|---|---|---|
| Sensor Data | 75 Deg +/− % | 40 | 40 | 40 |
| Sample Rate | 100 Threshold | 60 | 60 | 60 |
| Sensor Data % | 75% | 67% | 67% | 67% |

Described below are specific examples of P(BSE) calculations for ball strike and/or swing conditions in a real playing environment. These calculations are based on the first example of calculating the P(BSE) using (P)BSE=(C (% Degrees Up, Down, Horizontal)/Threshold)*(A/A Data Samples)+(P/P Data Samples)+(G/G Data/Samples)/3.

Table 21 shows an exemplary ideal ball strike. In this example, the club is being swung by a player and making full contact with the ball first. Ideally, all the sensor outputs should match the maximum sensor data indicating a full swing with ball impact.

TABLE 21

Ideal Ball Strike P(BSE) = 100%

| Sensors | Club Position | Accelerometer | Piezo | Gyro |
|---|---|---|---|---|
| Sensor Data | 100% | 100% | 100% | 100% |

The Table 22 shows an exemplary good ball strike. In this example, a ball strike event has occurred, but it is possible that the player did not take a full swing with the club (i.e., the club did not go completely vertical) or the player hit the ground before hitting the ball with the face of the club.

TABLE 22

Good Ball Strike P(BSE) = 96%

| Sensors | Club Position | Accelerometer | Piezo | Gyro |
|---|---|---|---|---|
| Sensor Data | 100% | 95% | 95% | 95% |

Table 23 shows the data that indicates a practice swing. In this situation, since the face of the club does not make contact with the ball, the club position, accelerometer, and gyro sensor indicate a club swing event, but the piezo data is at 0% indicating the club never made contact with the ball. The tag is configured to detect the above mentioned event, thereby preventing the piezo data from being stored at the tag, thus preventing the tag from transmitting any data to the location-aware device. Otherwise stated, since the piezo data is at 0%, the output of the piezo data does not exceed the threshold percentage set by the tag, and thereby not result in an output of data from the tag to the location-aware device.

TABLE 23

| Practice Swing P(BSE) = 73% | | | | |
|---|---|---|---|---|
| Sensors | Club Position | Accelerometer | Piezo | Gyro |
| Sensor Data | 100% | 95% | 0% | 95% |

Table 24 illustrates the sensor data in the case of a partial practice swing. This situation is similar to the example of the full practice swing in that the piezo data is at 0%. However, in this example, the acceleration data and the gyro sensor are also lower.

TABLE 24

| Partial Practice Swing P(BSE) = 65% | | | | |
|---|---|---|---|---|
| Sensors | Club Position | Accelerometer | Piezo | Gyro |
| Sensor Data | 100% | 80% | 0% | 80% |

Table 25 reflects the sensor data when the club makes contact with the ground prior to making contact with the ball during a full swing event. Obviously in this scenario a ball strike should be registered. When the club makes contact with the ground prior to striking the ball, all of the sensor outputs are reduced from that of an ideal shot, but all exceed 80%, for example, thus providing a high probability that a ball strike event has occurred.

TABLE 25

| Full Swing with Club Hitting Ground Then Ball P(BSE) = 89% | | | | |
|---|---|---|---|---|
| Sensors | Club Position | Accelerometer | Piezo | Gyro |
| Sensor Data | 95% | 80% | 90% | 90% |

Table 26 shows an example of the sensor outputs during a sand shot, in which the sand is impacted prior to making contact with the ball. In this example, the club position, accelerometer and gyro sensors all reflect a full swing, but the piezo sensor data is reduced due to the club impacting the sand before the ball. In this case, a 5 balls strike event should be registered.

TABLE 26

| Sand Shot P(BSE) = 78% | | | | |
|---|---|---|---|---|
| Sensors | Club Position | Accelerometer | Piezo | Gyro |
| Sensor Data | 95% | 67% | 90% | 90% |

Table 27 shows the sensor data when taking a chip shot or making a partial swing at the ball. Obviously, in this scenario, the accelerometer data will be impacted, but the club position, gyro and piezo data accounts for the deficiency of the accelerometer output. In this scenario, a ball strike event should be registered.

TABLE 27

| Pitch Shot P(BSE) = 76% | | | | |
|---|---|---|---|---|
| Sensors | Club Position | Accelerometer | Piezo | Gyro |
| Sensor Data | 95% | 60% | 90% | 90% |

Figure 50:
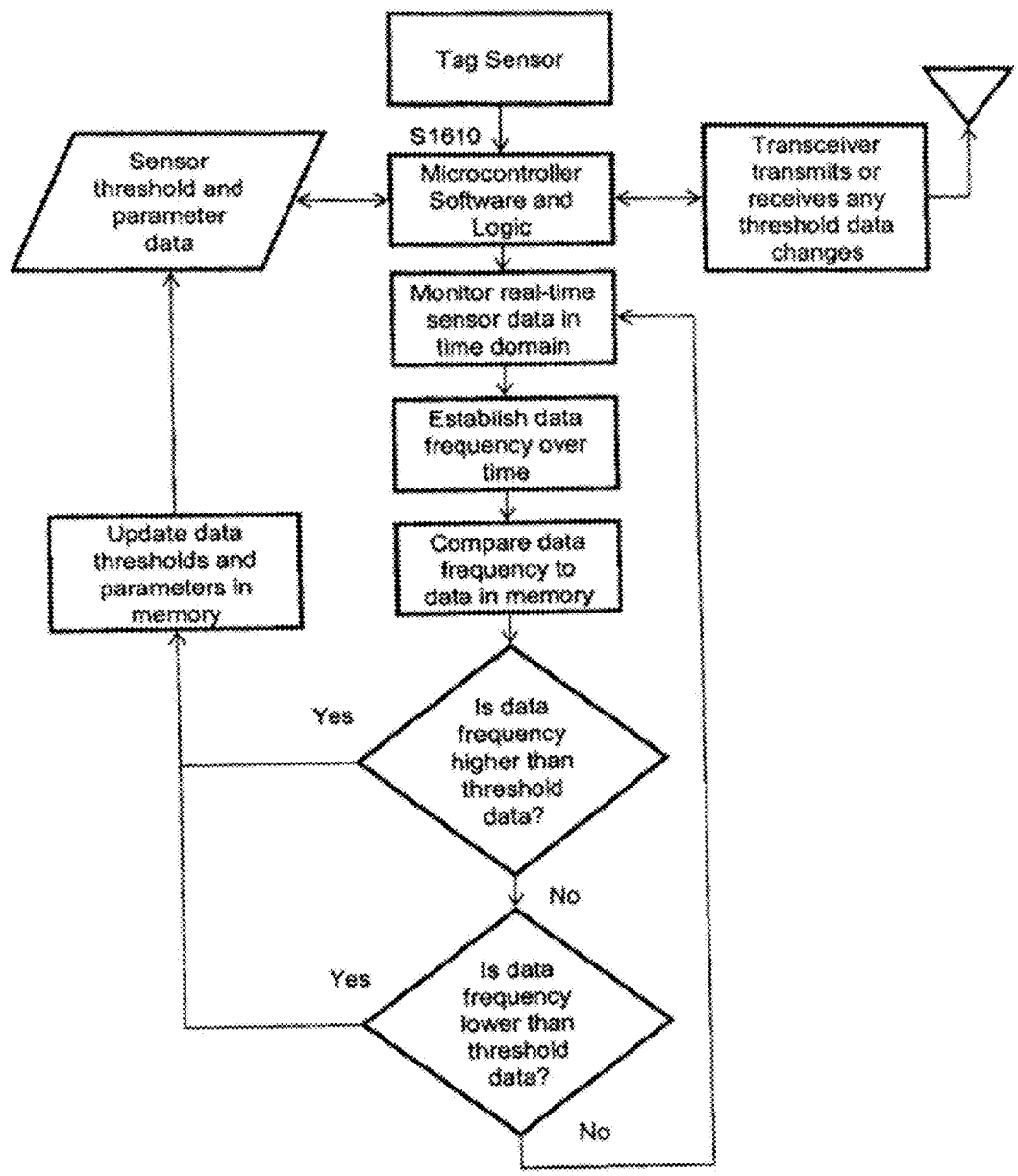
FIG. 50 illustrates an adaptive data collection and analysis process including a golf tag according to one embodiment of the present invention.

As discussed above, the thresholds included in the tags and location-aware device are configured to as to better detect a ball strike event. FIG. 50 describes the adaptive process pertaining to tags.

An advantage of having the ability to have configurable sensor thresholds, parameters and weighting factors in memory on both the tag and handheld systems is that it allows for refinement of the sensor data to the characteristics of different clubs and swing patterns. For example, a tag on a driver can have a different sensor processing profile compared to a golf club iron, sand wedge or putter. Each can be configured differently to accommodate the dynamics and characteristics of each club. Likewise, different swing patterns can be accommodated so as to accommodate the difference in the swing profile of a driver compared to a putter. Furthermore, the sensor processing profiles on the tags and location-aware device can be adaptive through active feedback from a user indicating that a shot resulted or did not result in a ball strike or conditions in which the club is or is not in the bag. In one embodiment, this feedback is transmitted to the tag(s) via the transceiver on the handheld device. Additionally, the tags could be self-adaptive in that the tags could sense sensor noise in the system and adjust their thresholds accordingly or inversely if the sensor input is too strong it could be adjusted down to a more appropriate level.

The sensor thresholds and parameters on the tags primarily act as filters to minimize sensor "noise" from adversely migrating into the sensor data. The tag sensor thresholds and parameters secondarily then act as "tuning" mechanisms to optimize the performance of the sensor with the respective club and thirdly to allow for adaptive tag sensor system optimizations as described above. This is accomplished by the microcontroller software and logic monitoring the real-time sensor data in the time domain when the tag sensor is in an active state. The data is processed by using Fast Fourier Transforms (FFT) or other techniques to establish levels of data frequency over time. This data is then compared to the sensor threshold and parameter data in memory and processed in a logic function to determine if the frequency of the data is higher than the threshold data in memory. If it is it adjusts the data thresholds and parameters and updates them into the memory. If the frequency of data is not higher after the comparison then a logic function determines that it is lower. If it is lower, then the threshold data is modified and updated into memory. If the adaptive process determines no threshold changes are needed, then the system continues monitoring the sensor data when the tag sensor is in an active state. The tag transceiver process transmits any adaptive threshold changes in memory to the location-aware device's receiver for monitoring in the location-aware device. The transceiver can also receive threshold and parameter data sent to the tag by the handheld for updating into the tag memory.

Figure 51:
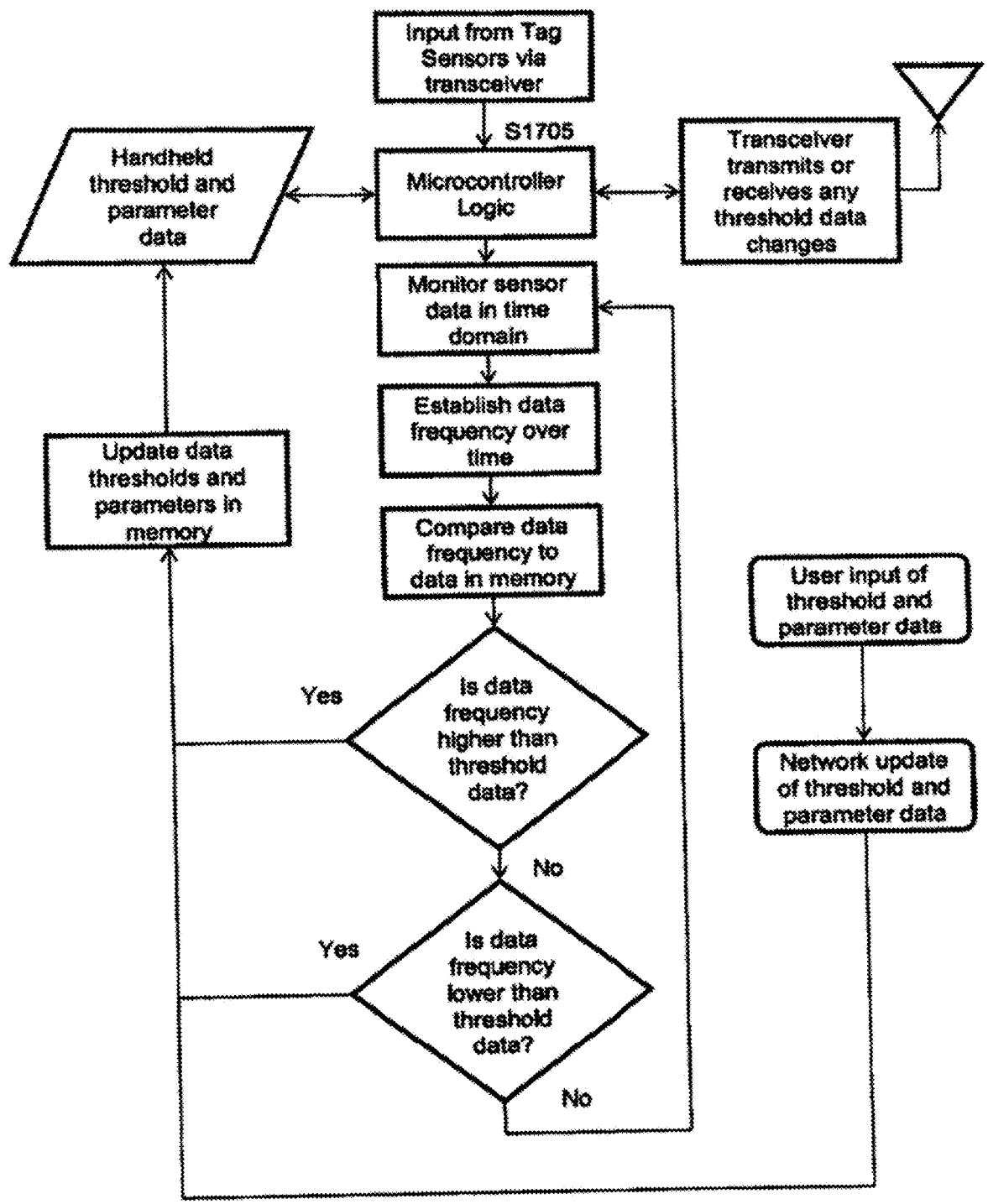
FIG. 51 illustrates an adaptive data collection and analysis process according to one embodiment of the present invention.

As described in FIG. 51, the sensor monitoring thresholds and parameters on the location-aware device allow the location-aware device to make determinations based on the patterns of the incoming tag sensor data as to whether a certain pattern of data was produced by the golf club striking a golf ball. As on the tags, the location-aware device specific thresholds and parameters can be modified in the handheld memory to optimize the data for certain club dynamics that are experienced for example by different golf club types, shafts, materials and manufacturers of clubs, etc. This is accomplished by monitoring the sensor data frequency over time and establishing a data frequency profile and then comparing the data frequency profile to the data thresholds and parameter profiles in the location-aware device memory. The data is processed through logic functions and to determine if the data indicates the thresholds and parameters for determining a club swing and ball strike need to be updated in memory.

It can likewise be adaptive in that they stem is operable to receive information from a golfer that an incoming sensor data pattern was or was not a golf shot resulting in a ball strike. Furthermore, it can be adaptive by receiving network updates either via a PC or web function to update the threshold and parameter data in memory. Over time, the process of analyzing the sensor data patterns can help determine what is "noise" in the incoming data and what is valid data and continually update the thresholds and parameters in memory as necessary. On both the tags and the location-aware device there are a set of default thresholds and parameters that the systems could always be reset to in the event of erroneous or corrupted threshold and parameter data in memory.

As described above, the location-aware device is capable of "polling" the tags to determine a status of the tags. This process is used to determine the status of the battery of each of the tags or is used to determine whether a tag, more specifically a club corresponding to the tag, is not within a communication distance of the location-aware device. If the tag is not reachable, it provides an alternative way of determining that the club was left behind on the course.

Figure 48A:
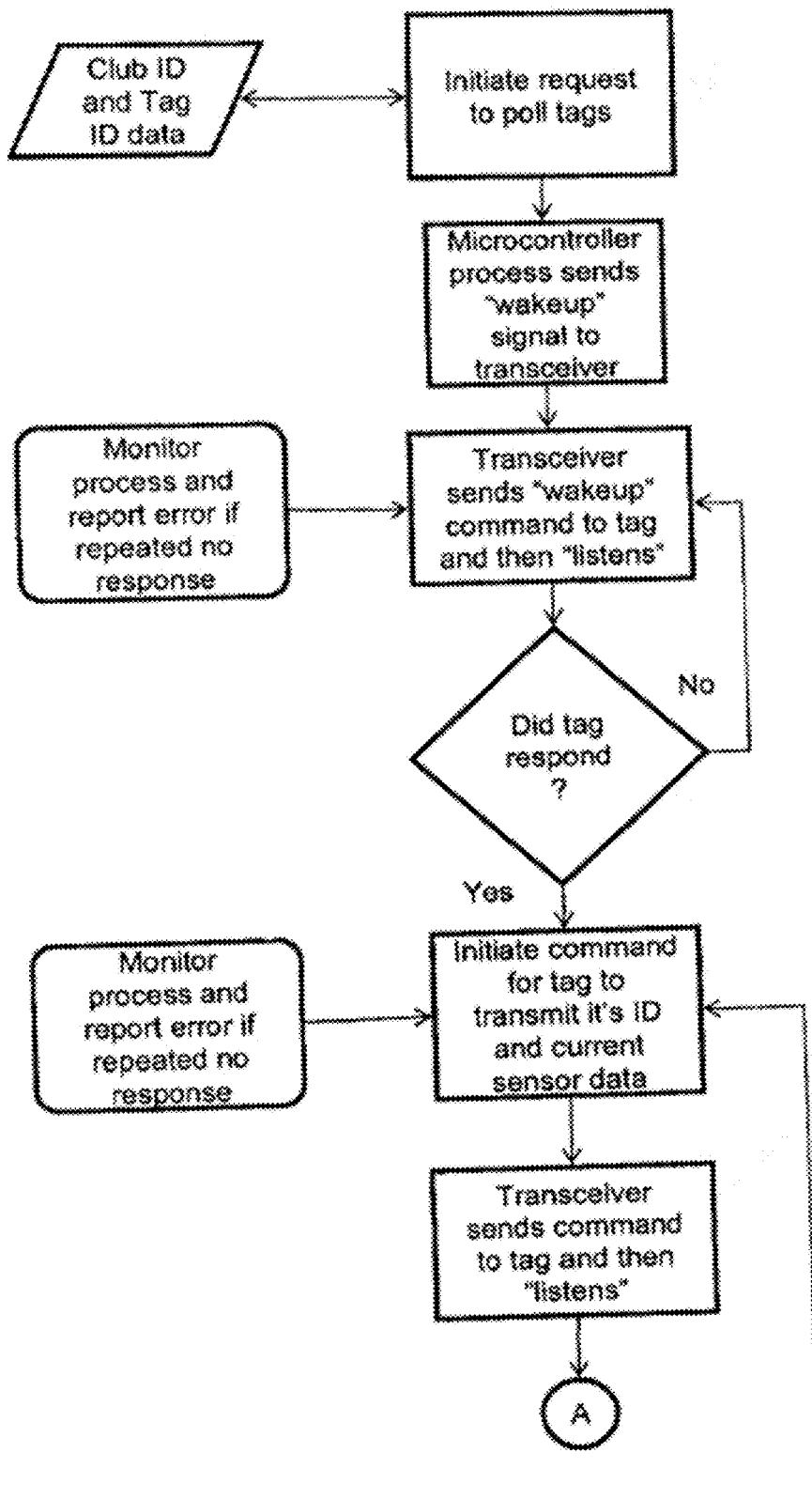
FIG. 48A illustrates a process of communication between a remote device and a golf tag according to one embodiment of the present invention.
Figure 48B:
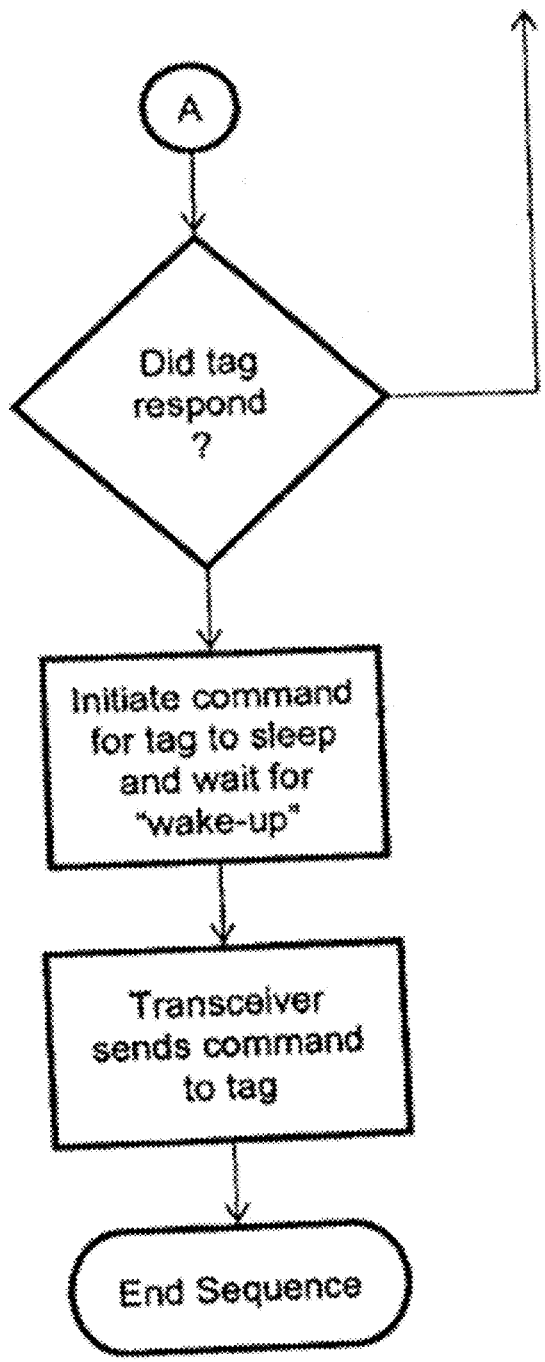
FIG. 48B illustrates a process of communication between a remote device and a golf tag according to one embodiment of the present invention.

FIGS. 48A-48B shows an exemplary embodiment of the process of actively retrieving (e.g., "polling") information from the tags by the location-aware device. Initially, the location-aware device initiates a request to poll information from the tags, by identifying the tags associated with the location-aware device. The process of polling information from the tags is operable to be initiated at a predetermined period of time during the operation of the location-aware device, or is configured be triggered by the failure of the tag to indicate that the club has been rendered at rest (i.e., returned to the player's bag) by sending an indication that the club has been returned to the bag. This is yet another configuration by which the location-aware device indicates that a club has been left behind by a player by determining that the location-aware device is no longer able to communicate with the tag.

Once the location-aware device determines to initiate a polling request to the tags, the microcontroller sends a "wake-up" signal to the transceiver, which transmits the signal to each of the plurality of tags. The microcontroller of the location-aware device then monitors to determine if the tags have transmitted a response to the wake-up message. If one or a plurality of the tags has not responded, the location-aware device then transmits another wake-up command to the tags. As discussed above, if one or more of the plurality of tags have not responded, the location-aware device displays a message to the player via the GUI of the location-aware device. The displayed message indicates that the tag is unresponsive, thus informing the user that either the battery of the tag is dead, or that the club has been lost or left behind.

Upon receiving a response from the tag, the location-aware device transmits a command to the tags requesting that the tags transmit its ID and current sensor data. The location-aware device monitors this subsequent request for information to determine if the tag is unresponsive after the initial request. Upon receiving the initial response to the wake-up command and transmitting the request for the tag ID and sensor data, the location-aware device waits for a response, and determines if the tag responds. If the tag has not yet responded, the location-aware device again transmits the request for the tags transmit their ID and current sensor data.

After receiving and processing the data from the tag, the location-aware device initiates a command for the tag to enter, or reenter a sleep state, and transmits this command to the tag. Optionally the tag can automatically go back into a "sleep" state.

Described below is a modification of the exemplary embodiment of the invention. In this modification, the accelerometer aboard the tag is capable of sensing all the data necessary to detect a ball strike.

Figure 49A:
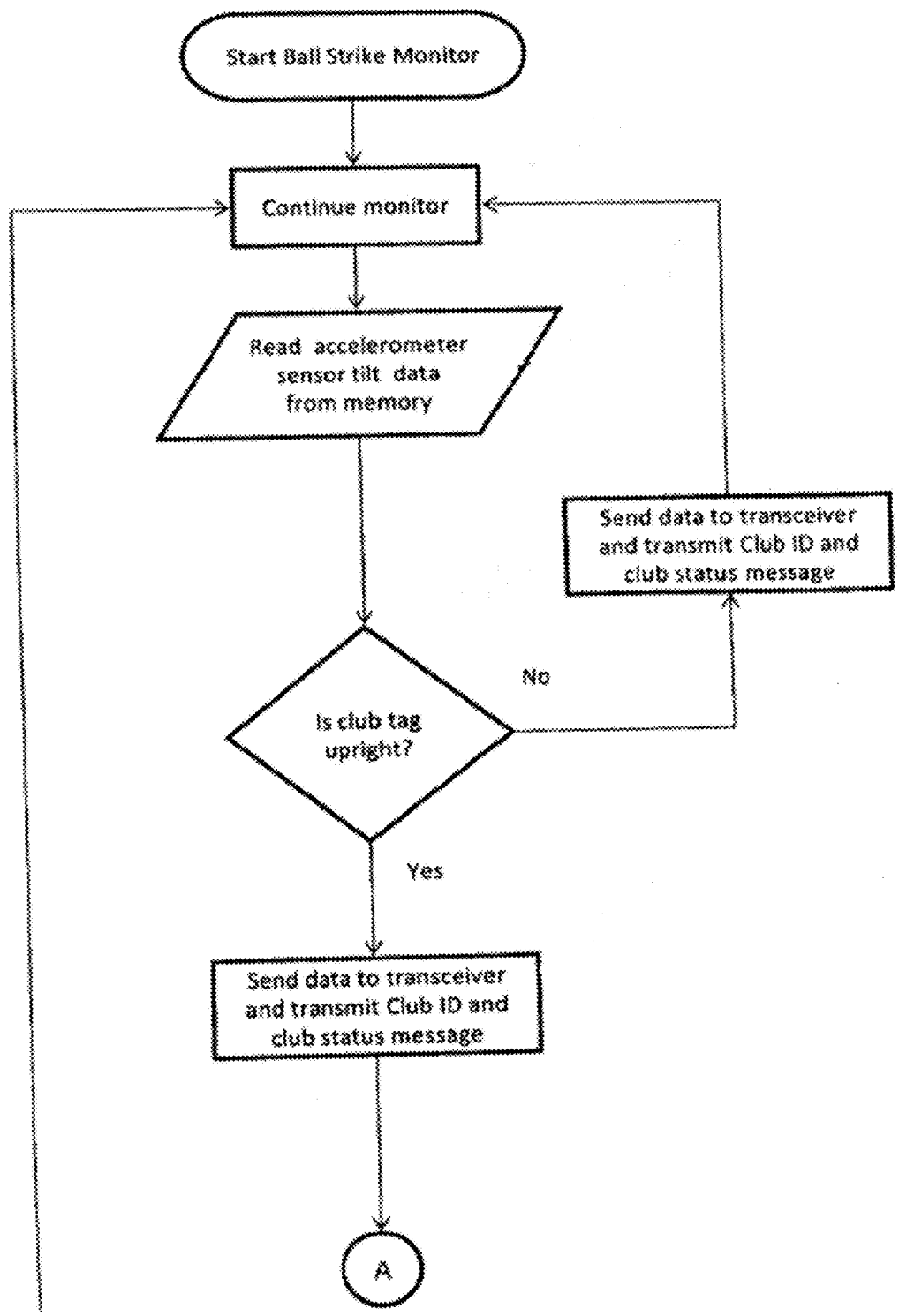
FIG. 49A illustrates a process of detecting a ball strike event using a golf tag with an accelerometer according to one embodiment of the present invention.
Figure 49B:
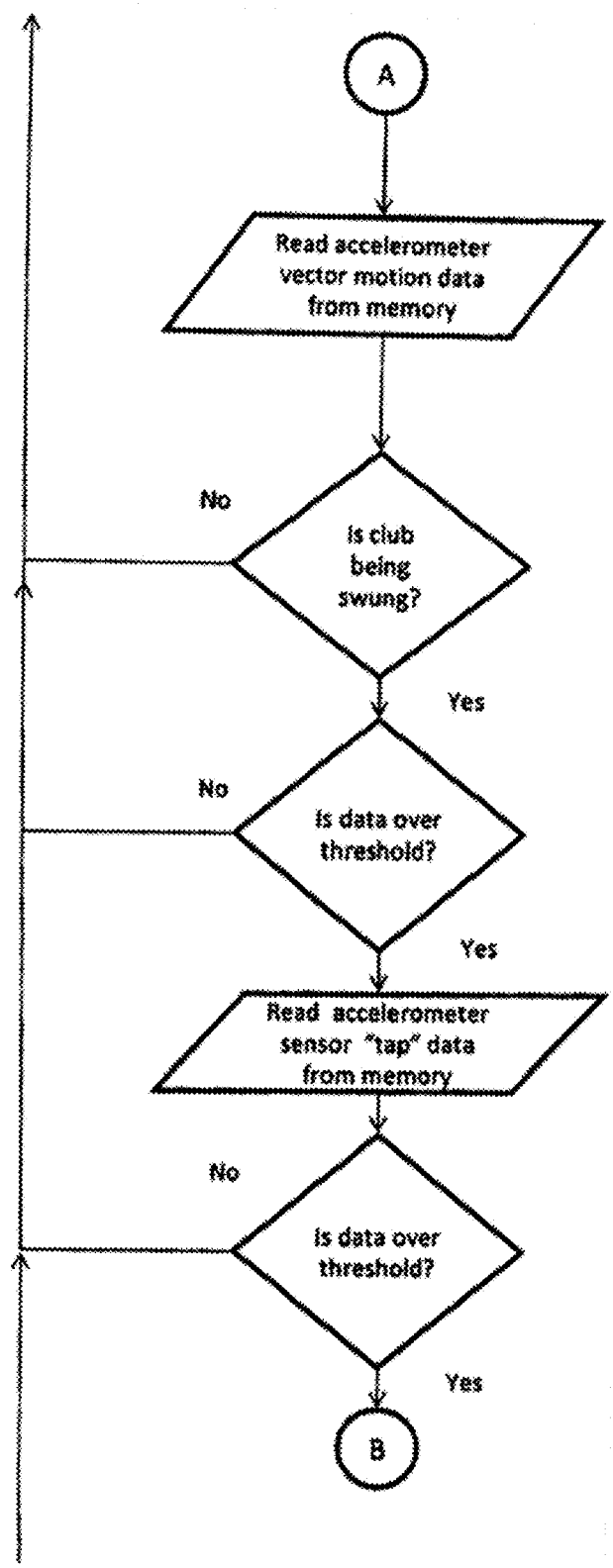
FIG. 49B illustrates a process of detecting a ball strike event using a golf tag with an accelerometer according to one embodiment as illustrated FIG. 50A.
Figure 49C:
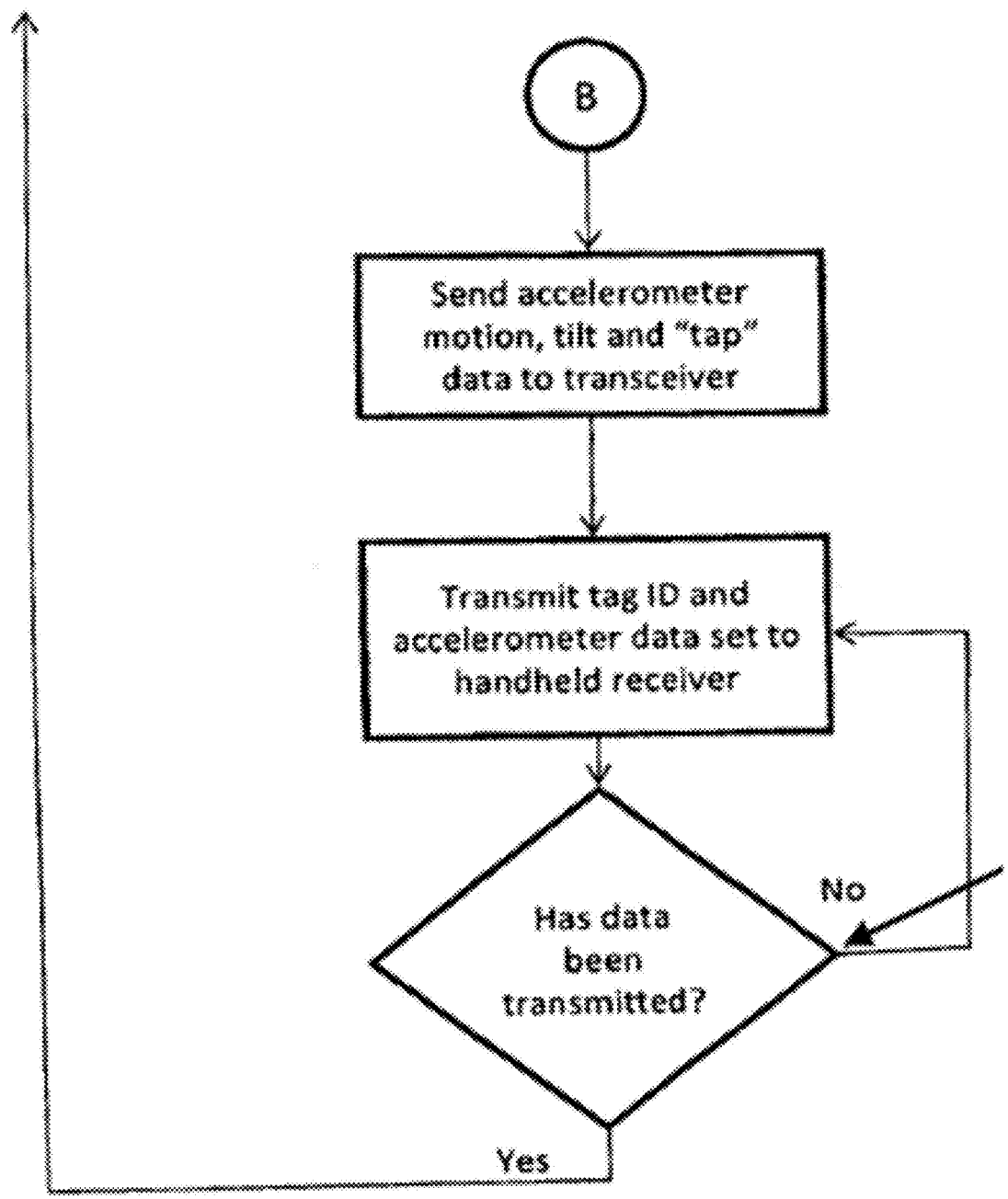
FIG. 49C illustrates a process of detecting a ball strike event using a golf tag with an accelerometer according to one embodiment as illustrated in FIG. 50C.

FIGS. 49A-49C disclose an exemplary embodiment of a process of detecting a ball strike event using a tag implementing only an accelerometer.

The microcontroller of the tag monitors a status of the tilt data provided by the accelerometer to determine if the club has been removed from the player's bag by determining if the club has been turned upright. If the club is not upright, the tag continues monitoring the tilt data to determine if the club has been removed from the bag and should be placed in an active state.

If the club is upright and determined to be in an active state, the microcontroller of tag controls the transceiver of the tag to send an indication to the location-aware device that the club is in an active state or has been removed from the bag. This transmitted information indicates both that the club is now in an active state, and includes a unique ID corresponding to the tag. As discussed above, this unique ID specifically identifies the club, or is some other type of ID that is specific to the tag and has previously been correlated with an identification of the club to which it is attached at the location-aware device. The location-aware device is configured to then display an indication to a user that a specific club has been selected for a shot.

Once the tag is determined to have transitioned into the active state, the microcontroller of the club reads accelerometer data from memory to determine if the club is being swung. If the club is not being swung based on the accelerometer data, the tag continues to monitor the status of the club. If the club is being swung, the microprocessor determines if the accelerometer data output exceeds a threshold value. If the data is determined not to exceed the threshold value, the tag continues to monitor the status of the club. If the output of the accelerometer exceeds the threshold value, the microcontroller reads the accelerometer tap data stored in memory and determines if this data exceeds a predetermined threshold. If the data is determined not to exceed the threshold value, the tag continues to monitor the status of the club. If the tap data exceeds the predetermined threshold, the microcontroller provides the accelerometer motion, tilt and tap data to the transceiver of the tag, which transmits the data along with tag ID information to the location-aware device. The tag then determines if the data has not been transmitted. If the data has not yet been transmitted, the process returns to and transmits the data. If the data has been transmitted, the process starts monitoring the status of the club. The location-aware device then processes the accelerometer motion, tilt and tap data, as discussed above with reference to FIG. 47, to determine if a ball strike event has occurred.

The present invention, therefore, is directed to a process of automatically detecting that a ball strike event has occurred based on sensor data detected by one or a plurality of sensors included in a tag attached to a golf club. The sensor data is initially processed by the tag to determine whether the sensor data indicates that the club has been removed from the bag. Once this determination is made, the sensor data is then initially processed by the tag to determine if the outputs of the sensor data indicate that a ball strike event has taken place. If the outputs of the sensors exceed these preliminary threshold values, the data is then passed onto the location-aware device for further processing to determine if a golf shot should be registered.

Various other advantages are realized by this tag configuration. For example, the configuration allows for the location-aware device to not only detect that a club has been lost, but also displays a location of this lost club to the user.

It should also be noted that the tag system in conjunction with a location-aware device is the preferred implementation of this invention because of the benefits of associating location information with the data, however a handheld, golf cart or golf bag mounted device that has no "location awareness" (i.e. no GPS, inertial systems or other location functions) can still utilize certain features of this system such as the club reminder function of notifying a golfer if he has not returned a club to the golf bag and automated scoring and statistics functions and tag polling functions for club bag inventory. There are many functions that are useful even though it does not include the shot latitudes/longitudes or geo-location data. The golfer could still use this system to automatically enter club used and shot data for automated scoring purposes and logging of data. The system is configured receive user input to approximate a golfer's shot location and distance manually on a GUI or via a data analysis function on a PC or web-based system.

When a ball is struck by a golf club there is a brief acoustic and air pressure wave generated that conducts up the golf shaft. This pressure wave can be utilized by the tag sensors to determine the existence and amplitude of a ball strike. The system is configured to combine the pressure data with other sensor data such as from the accelerometer and/or gyro data to indicate a ball strike with a high degree of probability.

In yet another embodiment, the present invention includes machine learning hardware and algorithms on the tag to adaptively improve the probability and determination of a golf club swing and ball strike. This could be accomplished with and/or without feedback from the user by the algorithm constantly "learning" and adapting to sensing a ball strike from the input of the plurality of sensors on the tag.

In another embodiment, the present invention includes a tag coupled to a golf club and software operable to provide golf performance analysis. The tag includes at least one sensor operable to capture motion data, position data, speed data, acceleration data, and other data related to a golf swing. The tag is in network communication with at least one remote device (e.g. a mobile device or a computing device). In one embodiment, the tag includes a processor configured to analyze the sensor data. The tag is configured to generate an alert when the processor detects that a golf ball has been struck. For example, and not limitation, the alert includes an audio cue and/or a visual cue. In another embodiment, the visual cue includes the golf tag changing color. In yet another embodiment, the tag is configured to send the sensor data to at least one remote device. The at least one remote device includes software operable to analyze the sensor data. The at least one remote device is further operable for network communication with at least one remote server. The at least one remote server is operable to provide golf course data and historical golf performance data to the at least one remote device. The at least one remote device is operable to generate a recommended target area based on the position data of the tag and the historical golf performance data. For example, and not limitation, the at least one remote device is configured to determine the position of a golfer (e.g. a starting position) in relation to a golf hole based on the position data and the golf course data. The at least one remote device is operable to create a recommended target area based on a distance between the starting position and a golf hole. Advantageously, the system is configured to include elevation data when analyzing the sensor data. The at least one remote device is configured to display a recommended club type based on the distance between the starting position and the golf hole.

In yet another embodiment, the at least one remote device is configured to determine the quality of a golf stroke based on at least one sensor attached to a tag coupled to a golf club. The at least one sensor is operable to capture motion data, position data, speed data, acceleration data, angle data, angular velocity data, and other similar data for a golf swing. The golf analysis system is configured to calculate a predicted resting position of a golf ball after the golf ball has been struck based on the analyzed sensor data. Advantageously, the golf analysis system is configured to receive environment data (e.g. wind data, precipitation data, humidity data) and to automatically modify a recommended target area and/or the estimated resting position based on the environment data.

For further description about motion capture sensors, see U.S. Pat. Nos. 10,706,273 and 10,159,885, which are incorporated herein by reference in their entirety.

In one embodiment, the tag is operable to attached to the top of a golf club. In another embodiment, the tag is configured to attach to a shaft of a golf club. For example, and not limitation, the golf tag is configured to wrap around the golf shaft. Alternatively, the golf tag is configured to attach to head of a golf club. In one embodiment, the tag includes a unique identifier. The golf analysis system is configured to use the unique identifier to correlate the tag and a particular golf club (e.g. a 3 wood).

In another embodiment, the tag is attached to the head of a golf club. The tag is configured to capture club head data during a golf swing. The club head data includes the speed of a golf swing, the angle of a golf swing, the angle of the club face when the golf ball is impacted, the force applied to the golf ball, when contact was made with the ground, how much contact was made with the ground, and the duration of time that contact was made with the ground. The golf system is further configured to determine if a golf club made contact with the ground too early, too late, too much or too little based on the tag sensor data. In another embodiment, the golfing system is configured to determine whether a person is swinging from the inside to the outside or from the inside to the outside via club head data captured during the golf swing. Generally, this results in an off-target golf shot. Advantageously, the golf system is configured to determine the predicted flight path and landing distance of the golf ball based on the tag data. Furthermore, the system is configured to send an alert to at least one remote device when the system detects based on the tag data that the golfer sliced or hooked the golf ball, thereby, helping the golfer identify where the ball traveled. The system is also configured to determine via the golf head tag data whether a swing was too shallow, too deep, a club face was open when it made contact with the ball, and/or a club face was closed when it made contact with the ball. The system is further operable to display a golfer's swing path and a corresponding flight path via the at least one remote device.

In one embodiment, the golfing system includes a wearable device. The wearable device includes, but is not limited to, a watch, glasses, a headset, a hat, a shirt, sock, shoes, pants, and/or shorts. In one embodiment, the watch includes an APPLE WATCH®. The wearable device is in network communication with the tag and the at least one remote device. The wearable device is operable to transmit swing data and location data to the at least one remote device. The at least one wearable device is further operable to receive user inputs related to the golf swing. For example, and not limitation, the wearable device is operable to receive user input identifying the club used, whether to add a penalty stroke, which hole the golfer is on, and other similar inputs used during a golf round. Additionally, the present invention includes a "break" mode. The break mode indicates to the wearable device and the at least one remote device that play is stopped (e.g. stopping at the clubhouse between the front nine and the back nine), so the wearable device and the at least one remote device reduce power consumption. Advantageously, this preserves the battery levels of the at least one remote device and the wearable device.

For further description relating to wearable devices, see US Patent Publication No. 2019/0051136, which is herein incorporated by reference in its entirety. For further description about a remote device for golfing, see US Patent Publication No. 2017/0274255 and U.S. Pat. No. 8,556,752, which are incorporated herein by reference in their entirety. In yet another embodiment, the present invention includes a betting platform. For example, and not limitation, the present invention is operable to send a prompt to at least one user interface (e.g. graphical user interface (GUI)) via at least one remote device for a bet relating to a golf hole, golf swing, golf course, and/or golf round. For example, and not limitation, the system is operable to provide a prompt to bet on whether a golfer will hit the fairway off of their tee shot. The system is further configured to receive user input for how much money to wager. For example, and not limitation, the GUI includes at least one slider, wherein the slider is configured to slide in one direction to increase the amount of money wagered and to slide in the opposite direction to decrease the amount wagered. The system is further operable to prompt users to bet on a golfer's swing speed, the angle of a golf stroke, the flight path of a golf ball, the height of a golf ball flight path, how close the golf ball will land to a target (e.g. the green), whether the golf ball will go over a hazard, and other similar statistics or situations that arise during a golf round. Advantageously, the betting system is operable to adapt to a golfer's handicap. For example, and not limitation, if a pair of golfers bet on who will win the hole, the system is operable to adjust the odds based on a person's handicap and subtract strokes as needed based on a golfer's handicap. Advantageously, the present system is operable to apply different handicaps for different holes depending on the hole type. For example, and not limitation, the golf hole type includes a par 3, a par 4, a par 5, a water hazard, a penal design hole, a heroic design hole, a detour design hole, a lay-up hole, an open design, a redan design, a dogleg left, a dogleg right, and other similar golf hole designs. The system is operable to determine that a golfer generally shoots two over par on a par 3 and give the golfer a 2 handicap on par 3s. Therefore, when the golfer is competing against a scratch golfer, the system is operable to account for the extra two strokes on par 3s when considering the final scores. The system is further configured to determine a golfer's handicap based on the golfer's previous golf rounds. For example, and not limitation, a first golfer has a 6 handicap so the first golfer is expected to shoot 6 over par on average whereas a second golfer has a 10 handicap so the second golfer is expected to shoot 10 over par on average. The system is configured to compare the final score with the handicaps to calculate the difference from the handicap to a golfer's final score. Then, the system is further operable to determine which golfer played better in relation to the golfer's handicap to determine a winner.

For further description about golf betting, see U.S. Pat. No. 5,507,485, which is incorporated herein by reference in its entirety.

In yet another embodiment, the present invention is operable for augmented reality and/or virtual reality applications. The tag is configured to couple to a golf club and is network communication with a virtual reality device and/or system. For example, and not limitation, the virtual reality system includes a headset that is configured to receive virtual reality data from at least one remote device and/or server. The virtual reality data includes audio data, visual data, and audiovisual data. The virtual reality data further includes golf course data. The virtual reality system is operable display a golf course and other virtual reality data to a user. Advantageously, this enables a user to virtually play a golf course without leaving their house. Additionally, the virtual reality system is configured to simulate private golf courses that are not playable by the general public. The virtual reality system is configured to simulate golf swings and shots based on a user's swing in a real world environment. In one embodiment, the virtual reality system is configured to estimate the speed, distance, flight path, and spin of a golf ball based on a user's golf swing. The virtual reality system is further operable to receive historical golf data from at least one server. The historical golf data includes at least one previous golf round for a user. The system is configured to display and simulate the round. Advantageously, a golfer can watch a virtual version (e.g. avatar) of themselves replay the round.

In yet another embodiment, an augmented reality system includes augmented reality glasses. The augmented reality glasses are configured to be used on a golf course to provide real-time analysis on a golfer's swing, shot, and golf round. For example, and not limitation, the augmented reality glasses are configured to generate an alert based on the tag data received from a golf tag on a golf club head or any other location on a golf club about the quality of a golfer's swing. Additionally, the augmented reality glasses are configured to provide at least one indicator of the direction of the flight path of the golf ball based on the tag data and/or a projected target location for the golf ball based on a golf swing. In another embodiment, the augmented reality glasses are configured to display a desired target for a golf shot and/or display past locations where a user has hit a golf ball on the course from the same starting point.

In another embodiment, the virtual or augmented reality system includes haptic feedback. The at least one remote device is configured to generate feedback via the golf tag based on a golfer's swing. For example, and not limitation, if a golfer makes a poor swing, the at least one remote device is configured to activate an actuator or piezo haptic sensor in the tag. The actuator is operable to provide vibrational feedback to the user to indicate the poor swing. In one embodiment, the virtual reality system is configured to receive user input relating to haptic feedback settings. For example, and not limitations, the virtual or augmented reality system is configured to receive input relating to the height of a golfer's swing. The virtual or augmented reality system is operable to vibrate if a user swings too high and/or over rotates their body. Advantageously, this provide real-time feedback for a user's swing.

In another embodiment, the present invention includes a social media platform. The at least one remote device is configured to transmit the tag data, including a golfing event, a golfing location, and/or a golfing video to a social media platform (e.g. FACEBOOK®, TWITTER®). For example, and not limitation, the present invention is configured to recognize when an individual hits an ideal golf strike and provide an alert to the social media platform. Alternatively, the present invention is configured to generate a report based on a golf round to a social media platform. In another embodiment, the present invention includes a golfer's social media platform configured for individuals to search for local golf courses. The system is operable to receive user feedback for golf courses. In one embodiment, the feedback includes at least one rating and/or at least one comment. Advantageously, the present invention is further operable for golfers to find courses and playing partners by tee time. For example, and not limitation, if a group of three golfers needs a fourth golfer, the system is operable to receive a request for a fourth golfer and sent an alert to other golfers that a fourth is needed. The system is further operable to receive and track a golfer's handicap. Therefore, the system is configured to post a golfer's handicap and/or a group's average handicap when prompting for another golfer. In another embodiment, the golf system is configured to generate an alert when a course is having a discount on its tee times.

The present invention is operable to utilize a plurality of learning techniques including, but not limited to, machine learning (ML), artificial intelligence (AI), deep learning (DL), neural networks (NNs), artificial neural networks (ANNs), support vector machines (SVMs), Markov decision process (MDP), and/or natural language processing (NLP). The present invention is operable to use any of the aforementioned learning techniques alone or in combination.

Further, the present invention is operable to utilize predictive analytics techniques including, but not limited to, machine learning (ML), artificial intelligence (AI), neural networks (NNs) (e.g., long short term memory (LSTM) neural networks), deep learning, historical data, and/or data mining to make future predictions and/or models. The present invention is preferably operable to recommend and/or perform actions based on historical data, external data sources, ML, AI, NNs, and/or other learning techniques. The present invention is operable to utilize predictive modeling and/or optimization algorithms including, but not limited to, heuristic algorithms, particle swarm optimization, genetic algorithms, technical analysis descriptors, combinatorial algorithms, quantum optimization algorithms, iterative methods, deep learning techniques, and/or feature selection techniques.

In yet another embodiment, the present invention is configured to work with blockchain technology and data encryption technology. Advantageously, data encryption is configured to protect a golfer's data, thereby keeping a golfer's data secure and providing the opportunity to create personalized in-app experiences. For example, and not limitation, the system is configured for public key cryptography and/or private key cryptography. In one embodiment, the system is configured to receive a golfer's medical record, including injuries or physical limitations. The golfing system is configured to adapt its recommendations based on the medical record. For example, and not limitation, if a golfer has an injured back, then the system is configured to recommend a softer swing or less rotation. In another embodiment, the golfing system is configured to send golfing videos to multiple remote devices without sending identifying information. The system is operable to receive feedback from other users and display the feedback with the transmitted video without providing identification information from the video creator or from any users that provided feedback.

In one embodiment, the present invention is operable to store data on a blockchain. The system is configured to receive user input via at least one remote device and/or at least one wearable device relating to a golfer and a golfer's score. The system is operable to provide incentives for providing information. For example, and not limitation, the system is configured to provide a code for a free round of golf for every five golf rounds recorded in the golfing system. In another embodiment, the golfing system includes a blockchain platform. The blockchain platform is configured to support non-fungible tokens (NFTs). The system is operable to capture and receive highlights of a golfer's score, round, swing and other highlights that occur during a golf round. The system is further configured to tokenize various highlights of a golfer and support buying and selling transactions for the golf highlights NFTs.

In yet another embodiment, the present invention is configured capturing and transmitting training and golf lessons via blockchain technology. The system is configured to receive training content from trainers, athletes, influencers and other widely known members of the golfing industry. The golf system is further configured to transfer the training content to individual golfers via the blockchain. The golfing system is configured to receive user input for a lesson and/or a training plan and to display the selected lesson and/or training plan via a GUI on a remote device, For further detail on tokenization of digital media, see US Patent Publication No. 2021/0166203, which is incorporated herein by reference in its entirety.

In a preferred embodiment, the platform is operable to store data on a distributed ledger, e.g., a blockchain. Distributed ledger technology refers to an infrastructure of replicated, shared, and synchronized digital data that is decentralized and distributed across a plurality of machines, or nodes. The node machines include but are not limited to a mobile device, a computer, a server, and/or any combination thereof. Data is replicated and synchronized across the plurality of nodes such that each node has a complete copy of the data ledger. The replication and synchronization of data across a distributed set of devices provides increased transparency over traditional data storage systems as multiple devices have access to the same set of records and/or database. Additionally, the use of distributed ledgers eliminates third-party and/or administrative authorities in that all of the nodes in the system are operable to receive, validate, and store additional data, thus creating a truly decentralized system. Eliminating the third party saves time and cost. A decentralized database is also more secure than traditional databases, which are stored on a single device and/or server, because it is more difficult to attack and/or irreparably tamper with the data as the decentralized data is replicated and spread out over both physical and digital space to segregated and independent nodes.

Figure 52:
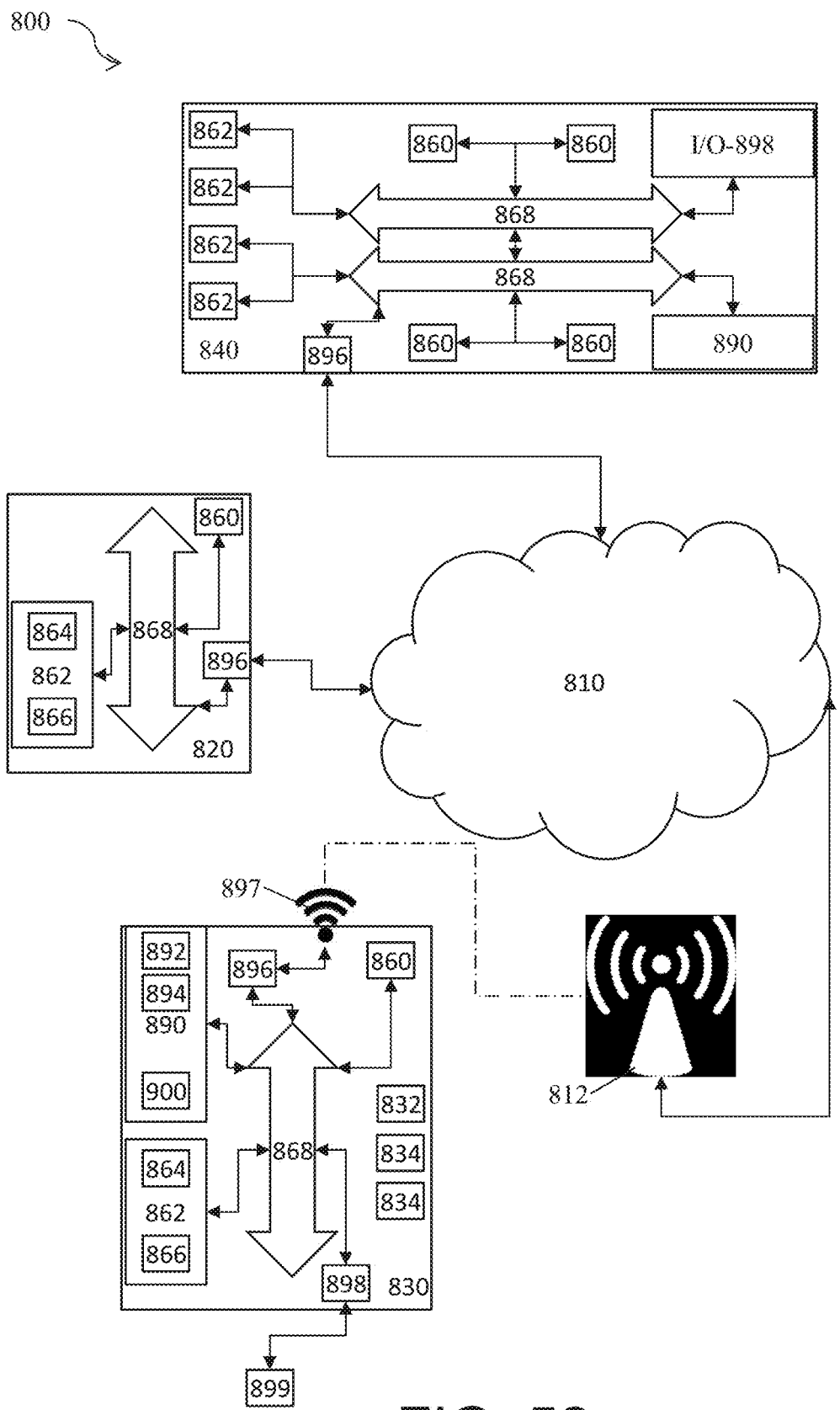
FIG. 52 is a schematic diagram illustrating a computer system for the present invention.

FIG. 52 is a schematic diagram of an embodiment of the invention illustrating a computer system, generally described as 800, having a network 810 and a plurality of computing devices 820, 830, 840. In one embodiment of the invention, the computer system 800 includes a cloud-based network 810 for distributed communication via the network's wireless communication antenna 812 and processing by a plurality of mobile computing devices 830, 840. In another embodiment of the invention, the computer system 800 is a virtualized computing system capable of executing any or all aspects of software and/or application components presented herein on the computing devices 820, 830, 840. In certain aspects, the computer system 800 is implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of digital devices 820 and mobile devices 830, 840 such as a server, blade server, mainframe, mobile phone, a personal digital assistant (PDA), a smart phone, a desktop computer, a netbook computer, a tablet computer, a workstation, a laptop, GPS-enabled device and other similar computing devices. The components shown here, their connections and relationships, and their functions, are meant to be exemplary only, and are not meant to limit implementations of the invention described and/or claimed in this document.

In one embodiment, the mobile device 830 includes components such as a processor 860, a system memory 862 having a random access memory (RAM) 864 and a read-only memory (ROM) 866, and a system bus 868 that couples the memory 862 to the processor 860. In another embodiment, the computing device 830 additionally includes components such as a storage device 890 for storing the operating system 892 and one or more application programs 894, a network interface unit 896, and/or an input/output controller 898. Each of the components are coupled to each other through at least one bus 868. Further, the mobile device 830 includes a graphical user interface or display 832 and various input mechanisms 834. The input/output controller 898 receives and process input from, or provide output to, a number of other devices 899, including, but not limited to, alphanumeric input devices, mice, electronic styluses, display units, docking stations, charging stations, touch screens, signal generation devices (e.g., speakers) or printers.

By way of example, and not limitation, the processor 860 includes a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown in FIG. 52, a computing device 840 includes multiple processors 860 and/or multiple buses 868, as appropriate, along with multiple memories 862 of multiple types (e.g., a combination of a DSP and a microprocessor, a plurality of microprocessors, one or more microprocessors in conjunction with a DSP core).

Also, in another embodiment, multiple computing devices are connected, with each device providing portions of the necessary operations (e.g., a server bank, a group of blade servers, or a multi-processor system). Alternatively, some steps or methods are performed by circuitry that is specific to a given function.

According to various embodiments, the computer system 800 operates in a networked environment using logical connections to local and/or remote computing devices 820, 830, 840, 850 through a network 810. A computing device 830 is connected to a network 810 through a network interface unit 896 connected to the bus 868. Computing devices communicate communication media through wired networks, direct-wired connections or wirelessly such as acoustic, RF or infrared through a wireless communication antenna 897 in communication with the network's wireless communication antenna 812 and the network interface unit 896, which include digital signal processing circuitry when necessary. The network interface unit 896 provides for communications under various modes or protocols.

In one or more exemplary aspects, the instructions are implemented in hardware, software, firmware, or any combinations thereof. A computer readable medium provides volatile or non-volatile storage for one or more sets of instructions, such as operating systems, data structures, program modules, applications or other data embodying any one or more of the methodologies or functions described herein. The computer readable medium includes the memory 862, the processor 860, and/or the storage device 890 and are a single medium or multiple media (e.g., a centralized or distributed computer system) that store the one or more sets of instructions 900. Non-transitory computer readable media includes all computer readable media, with the sole exception being a transitory, propagating signal per se. The instructions 900 are transmitted or received over the network 810 via the network interface unit 896 as communication media, which includes a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory or other solid state memory technology, disks or discs (e.g., digital versatile disks (DVD), HD-DVD, BLU-RAY, compact disc (CD), CD-ROM, floppy disc) or other optical storage, magnetic cassettes, magnetic tape, magnetic disk storage or other magnetic storage devices, or any other medium that can be used to store the computer readable instructions and which can be accessed by the computer system 800.

It is also contemplated that the computer system 800 does not include all of the components shown in FIG. 52, includes other components that are not explicitly shown in FIG. 52, or utilizes an architecture completely different than that shown in FIG. 52. The various illustrative logical blocks, modules, elements, circuits, and algorithms described in connection with the embodiments disclosed herein are implemented as electronic hardware, computer software or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

Certain modifications and improvements will occur to those skilled in the art upon a reading of the foregoing description. By way of example, automatic conversion between English units of measure (such as feet, yards) to metric equivalents may be included for user convenience. The above mentioned examples are provided to serve the purpose of clarifying the aspects of the invention and it will be apparent to one skilled in the art that they do not serve to limit the scope of the invention. All modifications and improvements have been deleted herein for the sake of conciseness and readability but are properly within the scope of the present invention and the following claims.

The invention claimed is:

1. A method for golf analysis, comprising:
   at least one server with at least one database storing information and providing the information over a network to an application;
   determining a starting position based on a first location of a tag coupled to a golf club;
   storing the starting position;
   determining a type of golf club based on the tag coupled to the golf club;
   defining a recommended target area for a next golf shot based on historical performance data for the type of golf club and the starting position;
   receiving wind data, precipitation data, and humidity data;
   automatically modifying the recommended target area based on the wind data, the precipitation data, the humidity data, and/or the starting position, wherein the starting position further includes lie data;
   receiving a resting ball location based on a second location of the tag coupled to the golf club, wherein the second location is the landing position of the next golf shot; and
   calculating whether the resting ball location is within the recommended target area.

2. The method of claim 1, further comprising receiving at least one target area modification, wherein the at least one target area modification is received from a mobile device.

3. The method of claim 2, wherein the at least one target area modification includes a change in length, width, shape, perimeter, area, and/or elevation of the recommended target area.

4. The method of claim 1, further comprising determining a three-dimensional distance from the resting ball location to the recommended target area, wherein the three-dimensional distance includes a left distance or a right distance, a forward distance or a backward distance, and elevation.

5. The method of claim 1, further comprising determining a distance between the recommended target area and the starting position, wherein the distance between the starting position and the recommended target area includes a difference in elevation.

* * * * *